United States Patent
Li et al.

(10) Patent No.: US 10,415,081 B2
(45) Date of Patent: Sep. 17, 2019

(54) MULTIPLEXED ANALYSIS OF POLYMORPHIC LOCI BY CONCURRENT INTERROGATION AND ENZYME-MEDIATED DETECTION

(71) Applicant: BioArray Solutions, Ltd., Warren, NJ (US)

(72) Inventors: Alice Xiang Li, Ithaca, NY (US); Ghazala Hashmi, Lomdel, NJ (US); Michael Seul, Fanwood, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 0 days.

(21) Appl. No.: 15/228,377

(22) Filed: Aug. 4, 2016

(65) Prior Publication Data

US 2016/0340723 A1    Nov. 24, 2016

Related U.S. Application Data

(60) Continuation of application No. 13/345,175, filed on Jan. 6, 2012, now abandoned, which is a division of
(Continued)

(51) Int. Cl.
  *C12Q 1/68* (2018.01)
  *C12Q 1/6827* (2018.01)
  (Continued)

(52) U.S. Cl.
  CPC ........ *C12Q 1/6827* (2013.01); *C12Q 1/6837* (2013.01); *C12Q 1/6858* (2013.01);
  (Continued)

(58) Field of Classification Search
  None
  See application file for complete search history.

(56) References Cited

U.S. PATENT DOCUMENTS

| 3,329,638 A | 7/1967 | Blyth |
| 3,574,614 A | 4/1971 | Carreira |
| (Continued) |

FOREIGN PATENT DOCUMENTS

| CA | 1248873 | 1/1989 |
| DE | 4035714 | 5/1992 |
| (Continued) |

OTHER PUBLICATIONS

Beaudet et al. (Homogeneous Assays for Single-Nucleotide Polymorphism Typing Using AlphaScreen, Genome Res. Apr. 2001;11(4):600-8, Apr. 15, 2001).*
(Continued)

*Primary Examiner* — Aaron A Priest
(74) *Attorney, Agent, or Firm* — Mintz, Levin, Cohn, Ferris, Glovsky and Popeo, P.C.

(57) ABSTRACT

The invention provides methods and processes for the identification of polymorphisms at one ore more designated sites, without interference from non-designated sites located within proximity of such designated sites. Probes are provided capable of interrogation of such designated sites in order to determine the composition of each such designated site. By the methods of this invention, one ore more mutations within the CFTR gene and the HLA gene complex can be identified.

13 Claims, 25 Drawing Sheets

Specification includes a Sequence Listing.

Related U.S. Application Data application No. 11/438,741, filed on May 22, 2006, now abandoned, which is a division of application No. 10/271,602, filed on Oct. 15, 2002, now abandoned.

(60) Provisional application No. 60/364,416, filed on Mar. 14, 2002, provisional application No. 60/329,620, filed on Oct. 15, 2001, provisional application No. 60/329,428, filed on Oct. 15, 2001, provisional application No. 60/329,427, filed on Oct. 15, 2001, provisional application No. 60/329,619, filed on Oct. 15, 2001.

(51) Int. Cl.
    *C12Q 1/6837*      (2018.01)
    *C12Q 1/6858*      (2018.01)
    *C12Q 1/6883*      (2018.01)

(52) U.S. Cl.
    CPC ..... *C12Q 1/6883* (2013.01); *C12Q 2600/156* (2013.01); *C12Q 2600/16* (2013.01)

(56) References Cited

U.S. PATENT DOCUMENTS

| | | |
|---|---|---|
| 3,790,492 A | 2/1974 | Fulwyler |
| 3,957,741 A | 5/1976 | Rembaum et al. |
| 3,982,182 A | 9/1976 | Hogg |
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Bömer |
| 4,717,655 A * | 1/1988 | Fulwyler ............... C12Q 1/04 435/34 |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A | 11/1995 | Shah et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |

(56) References Cited

U.S. PATENT DOCUMENTS

| | | |
|---|---|---|
| 5,496,699 A | 3/1996 | Sorenson |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | VanNess et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Wiley |
| 5,643,765 A | 7/1997 | Wiley |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,679 A | 10/1997 | Fuller |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,722,470 A | 3/1998 | Kedar et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,744,299 A | 4/1998 | Henrickson et al. |
| 5,744,305 A | 4/1998 | Fodor et al. |
| 5,747,349 A | 5/1998 | Van Den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |
| 5,770,358 A | 6/1998 | Dower et al. |
| 5,770,367 A | 6/1998 | Southern et al. |
| 5,770,455 A | 6/1998 | Cargill et al. |
| 5,770,721 A | 6/1998 | Ershov et al. |
| 5,773,222 A | 6/1998 | Scott |
| 5,776,711 A | 7/1998 | Vyas et al. |
| 5,779,976 A | 7/1998 | Leland et al. |
| 5,780,233 A * | 7/1998 | Guo .............. C12Q 1/6827 435/6.1 |
| 5,786,219 A | 7/1998 | Zhang et al. |
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,855,753 A | 1/1999 | Trau et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A | 9/1999 | Nikiforoy et al. |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |
| 5,988,432 A | 11/1999 | Sun |
| 5,989,835 A | 11/1999 | Dunlay et al. |
| 5,993,935 A | 11/1999 | Rasmussen et al. |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,018,350 A | 1/2000 | Lee et al. |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,033,547 A | 3/2000 | Trau et al. |
| 6,043,354 A | 3/2000 | Hillebrand et al. |
| 6,048,690 A | 4/2000 | Heller |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |

(56) References Cited

U.S. PATENT DOCUMENTS

| | | |
|---|---|---|
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | Feazel et al. |
| 6,103,379 A | 8/2000 | Margel et al. |
| 6,106,685 A | 8/2000 | McBride et al. |
| 6,114,123 A | 9/2000 | Murray et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,133,436 A | 10/2000 | Koster et al. |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,150,105 A | 11/2000 | Dahlhauser |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 5/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1* | 6/2001 | Seul .................. B01J 19/0046 204/400 |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,766 B1 | 9/2001 | Nolan et al. |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,489,159 B1 | 12/2002 | Chenchik et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauver et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,709,816 B1* | 3/2004 | Huang ............... C12Q 1/6827 435/174 |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 | 6/2005 | Ravkin et al. |
| 6,942,968 B1 | 9/2005 | Dickinson et al. |
| 6,955,751 B1 | 10/2005 | Seul |

(56) References Cited

U.S. PATENT DOCUMENTS

| | | |
|---|---|---|
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,732,575 B2 | 6/2010 | Wang et al. |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |
| 2001/0034614 A1 | 10/2001 | Fletcher-Haynes et al. |
| 2001/0044531 A1 | 11/2001 | McGall et al. |
| 2001/0046602 A1 | 11/2001 | Chandler et al. |
| 2001/0046673 A1* | 11/2001 | French ............... C12Q 1/6827 435/6.11 |
| 2001/0049095 A1 | 12/2001 | Webster |
| 2002/0006634 A1 | 1/2002 | Han et al. |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082549 A1 | 5/2003 | Liu |
| 2003/0082587 A1 | 5/2003 | Seul et al. |
| 2003/0087228 A1 | 5/2003 | Bamdad et al. |
| 2003/0104372 A1* | 6/2003 | Ahmadian ........... C12Q 1/6858 435/6.11 |
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2007/0264641 A1 | 11/2007 | Li et al. |
| 2008/0020374 A1 | 1/2008 | Greene et al. |
| 2008/0123089 A1 | 5/2008 | Seul et al. |
| 2008/0138800 A1 | 6/2008 | Li et al. |
| 2008/0167195 A1 | 7/2008 | Li et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |
| 2012/0214681 A1 | 8/2012 | Li et al. |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 1394270 | 3/2004 |
| EP | 1564306 | 2/2005 |
| JP | 62265567 | 11/1987 |
| JP | 03-236777 | 10/1991 |
| WO | WO-8911101 | 5/1989 |
| WO | WO-9109141 | 6/1991 |
| WO | WO-9119023 | 12/1991 |
| WO | WO-9210092 | 6/1992 |
| WO | WO-9325563 | 6/1992 |
| WO | WO-9302360 | 2/1993 |
| WO | WO-93/06121 | 4/1993 |
| WO | WO-93/25563 | 4/1993 |
| WO | WO-9306121 | 4/1993 |
| WO | WO-9324517 | 12/1993 |

(56) References Cited

FOREIGN PATENT DOCUMENTS

| | | |
|---|---|---|
| WO | WO-94000810 | 1/1994 |
| WO | WO-9428028 | 9/1994 |
| WO | WO-95/09248 | 10/1994 |
| WO | WO-9509248 | 4/1995 |
| WO | WO-9512608 | 5/1995 |
| WO | WO-9512808 | 5/1995 |
| WO | WO-9600148 | 1/1996 |
| WO | WO-9602558 | 2/1996 |
| WO | WO-9603212 | 2/1996 |
| WO | WO-9604547 | 2/1996 |
| WO | WO-9607917 | 3/1996 |
| WO | WO-9630392 | 10/1996 |
| WO | WO-9641011 | 12/1996 |
| WO | WO-9714028 | 4/1997 |
| WO | WO-9722720 | 6/1997 |
| WO | WO-9739151 | 10/1997 |
| WO | WO-9740383 | 10/1997 |
| WO | WO-9740385 | 10/1997 |
| WO | WO-9745559 | 12/1997 |
| WO | WO-9802752 | 1/1998 |
| WO | WO-9804950 | 2/1998 |
| WO | WO-9806007 | 2/1998 |
| WO | WO-9820153 | 5/1998 |
| WO | WO-9821593 | 5/1998 |
| WO | WO-9838334 | 9/1998 |
| WO | WO-9840726 | 9/1998 |
| WO | WO-9853093 | 11/1998 |
| WO | WO-9853093 A1 * 11/1998 .......... B01J 19/0046 |
| WO | WO-9909217 | 2/1999 |
| WO | WO-9918434 | 4/1999 |
| WO | WO-9919515 | 4/1999 |
| WO | WO-9922030 | 5/1999 |
| WO | WO-9924822 | 5/1999 |
| WO | WO-9935499 | 7/1999 |
| WO | WO-9936564 | 7/1999 |
| WO | WO-9941273 | 8/1999 |
| WO | WO-9951773 | 10/1999 |
| WO | WO-9960170 | 11/1999 |
| WO | WO-9967641 | 12/1999 |
| WO | WO-0003004 | 1/2000 |
| WO | WO-0004372 | 1/2000 |
| WO | WO-0007019 | 2/2000 |
| WO | WO-0013004 | 3/2000 |
| WO | WO-0020593 | 4/2000 |
| WO | WO-0022172 | 4/2000 |
| WO | WO-0026920 | 5/2000 |
| WO | WO-0031356 | 6/2000 |
| WO | WO-0039587 | 7/2000 |
| WO | WO-0046602 | 8/2000 |
| WO | WO-0047766 A1 * 8/2000 ........... C12Q 1/6858 |
| WO | WO-0051058 | 8/2000 |
| WO | WO-00/63437 | 10/2000 |
| WO | WO-0062048 | 10/2000 |
| WO | WO-0073777 | 12/2000 |
| WO | WO-0075373 | 12/2000 |
| WO | WO-0101184 | 1/2001 |
| WO | WO-0120179 | 3/2001 |
| WO | WO-0136679 | 5/2001 |
| WO | WO-0154813 | 8/2001 |
| WO | WO-0156216 | 8/2001 |
| WO | WO-0184150 | 11/2001 |
| WO | WO-0188535 | 11/2001 |
| WO | WO-0194947 | 12/2001 |
| WO | WO-0198765 | 12/2001 |
| WO | WO-0212888 | 2/2002 |
| WO | WO-0214864 | 2/2002 |
| WO | WO-0231182 | 4/2002 |
| WO | WO-0233084 | 4/2002 |
| WO | WO-0235441 | 5/2002 |
| WO | WO-0237209 | 5/2002 |
| WO | WO-02057496 | 7/2002 |
| WO | WO-02058379 | 7/2002 |
| WO | WO-02061121 | 8/2002 |
| WO | WO-02079490 | 10/2002 |
| WO | WO-02084285 | 10/2002 |
| WO | WO-02096979 | 12/2002 |
| WO | WO-03020968 | 3/2003 |
| WO | WO-03025011 | 3/2003 |
| WO | WO-03034029 | 4/2003 |
| WO | WO-03058196 | 7/2003 |
| WO | WO-03079401 | 9/2003 |
| WO | WO-0392546 | 11/2003 |
| WO | WO-04035426 | 4/2004 |
| WO | WO-05000236 | 1/2005 |
| WO | WO-05042763 | 5/2005 |
| WO | WO-05045059 | 5/2005 |
| WO | WO-05095650 | 10/2005 |
| WO | WO-0840257 | 4/2008 |
| WO | WO-0988893 | 7/2009 |
| WO | WO-1025002 | 3/2010 |
| WO | WO-1026038 | 3/2010 |
| WO | WO-1098765 | 9/2010 |
| WO | WO-10143678 | 12/2010 |

OTHER PUBLICATIONS

Fulton et al. (Advanced multiplexed analysis with the FlowMetrix system, Clin Chem. Sep. 1997;43(9):1749-56).*

Armstrong et al., "Suspension arrays for high throughput, multi-plexed single nucleotide polymorphism genotyping" Cytometry. vol. 40:102-108 (2000).

Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).

B. -Y. Ha et al., "Counterion-Mediated Attraction between Two Like-Charged Rods," Physical Review Letters, Aug. 18, 1997, vol. 79, No. 7, pp. 1289-1292.

A. Hatch, et al., "Diffusion Immunoassay in Polyacrylamide Hydrogels". Micro Total Analysis Systems, pp. 571-572 (2001).

Aho et al., "Efficient String Matching: An Aid to Bibliographic Search". Communications of the ACM, vol. 18, No. 6, pp. 333-340 (Jun. 1975).

Albergo et al., "Solvent effects on the thermodynamics of double-helix formation in (dG-sC) 3". Biochemistry, vol. 20, No. 6: 1413-1418 (1981).

Albrecht et al, "Probing the role of multicellular organization in three-dimensional microenvironments". Nature Methods, vol. 3, No. 5, pp. 369-375 (May 2006).

Albrecht et al., "Photo and electropatterning of hydrogel-encapsulated living cell arrays", Lab on a Chip, vol. 5, Issue 1, pp. 111-118 (2004).

Al-Soud, W. A., "Purification and Characterization of PCR-Inhibitory Components in Blood Cells". Journal of Clinical Microbiology, vol. 39, No. 2, pp. 485-493 (Feb. 2001).

Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).

Ambruso, D. R., et al., "Experience with donors matched for minor blood group antigens in patients with sickle cell anemia who are receiving chronic transfusion therapy", Transfusion, vol. 27, No. 1, 1987, pp. 94-98.

Zhang, Y., et al., "Reproducible and inexpensive probe preparation for oligonucleotide arrays". Nucleic Acids Research, vol. 29, No. 13, pp. E66-E6 (Jul. 1, 2001).

Arenko, et al., "Protein microchips: Use for immunoassay and enzymatic reactions". Analytical Biochemistry, vol. 278, pp. 123-131 (2000).

Assie et al., Correlation between low/high affinity ratios for 5-HT Receptors and Intrinsic Activity, European Journal of Pharmacology, vol. 386, pp. 97-103 (1999).

Bakewell et al., "Characterization of the dielectrophoretic movement of DNA in micro-fabricated structures", Institute of Physics Conference Series (1999) Electrostatics (1999).

Balass et al. "Recovery of high-affinity phage from a Nitrostretavidin matrix in phage-display technology". Analytical Biochemistry. vol. 243: 264-269 (1996).

(56) References Cited

OTHER PUBLICATIONS

Baldwin, et al., "Phosphorylation of gastrin-17 by epidermal growth factor-stimulated tyrosine kinase". Nature, vol. 44, pp. 2403-2404 (1998).
Bandeira-Melo, C., et al., "EliCell: A gel-phase dual antibody capture and detection assay to measure cytokine release from eosinophils". Journal of Immunological Methods, vol. 244, pp. 105-115 (2000).
Bao, Y. P., et al., "Detection of Protein Analytes via Nanoparticle-Based Bio Bar Code Technology". Anal. Chem., vol. 78, pp. 2055-2059 (2006).
Barany, Francis, "Genetic Disease Detection and DNA Amplification using Cloned Thermostable Ligase". Proceedings of the National Academy of Sciences of the United States of America, vol. 88, pp. 189-193 (Jan. 1991).
Barnard et al. "A fibre-optic chemical sensor with descrete sensing sites". Nature, vol. 353:338-340 (1991).
Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).
Battersby et al., "Toward Larger Chemical Libraries: Encoding with Fluorescent Colloids in Combinatorial Chemistry". J. Amer Chem Soc, vol. 122, pp. 2138-2139 (2000).
Baumgarth N. et al., A practical approach to multicolor flow cytometry for immunophenotyping, J. Immunological Methods, 2000, pp. 77-97, vol. 243.
Bavykin, S.G., et al., "Portable system for microbial sample preparation and oligonucleotide microarray analysis". Appl. Environmental Microbiol. 67(2), 922-928 (2001).
Beatty et al. "Probability of Finding HLA-mismatched Related or Unrelated Marrow or Cord Blood Donors", Human Immunology, 2001, vol. 61, pp. 834-840.
Beebe et al., "Functional Hydrogel structures for autonomous flow control inside microfluidic channels". Nature, vol. 404, No. 6778, pp. 588-590 (Apr. 6, 2000).
Beiboer, S. W., et al., "Rapid genotyping of blood group antigens by multiplex polymerase chain reaction and DNA microarray hybridization" 45 Transfusion 667-679 (2005).
Bennett, P. R., et al., "Prenatal Determination of Fetal RhD Type by DNA Amplification". The New England Journal of Medicine, vol. 329, No. 9, pp. 607-610 (Aug. 26, 1993).
Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).
Bessetti, J., "An introduction to PCT Inhibitors". Profiles in DNA-PCR Inhibition, pp. 9-10 (Mar. 2007).
Bickel, P. J., "Discussion of the Evaluation of Forensic DNA Evidence". Proc. Natl. Acad. Sci., vol. 94, p. 5497 (May 1997).
Zhang, X., et al., "Strand invasion by mixed base PNAs and a PNA-peptide chimera". Nucleic Acids Research, vol. 28, No. 17, pp. 3332-3338 (2000).
Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.
Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).
Boyd et al., "Tosyl Chloride activation of a rayon/polyester cloth for protein immobilization", Biotechnology Techniques, Apr. 1993, vol. 7, 4:277-282.
Braga et al., "Hydrophobic Polymer Modification with Ionic Reagents: Polysterene Staining with Water-Soluble Dyes". Langmuir, vol. 19, No. 18, pp. 7580-7586 (2003).

Breslauer, K.J. et al., "Predicting DNA duplex stability from the base sequence". PNAS USA, vol. 83, pp. 3746-3750 (1986).
Brick, et al., "Formation of Colloidal Dispersions of Organic Materials in Aqueous Media by Solvent Shifting". Langmuir, vol. 19, No. 16, pp. 6367-6380 (Jan. 31, 2003).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". BioTechniques, vol. 27, pp. 528-536 (Sep. 1999).
Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Campian et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonnucleotide probes (SSOP)", Rev Immunogenetics 1:177-208 (1999).
Cao et al., "Nanoparticles with Raman Spectroscopic Fingerprints for DNA and RNA Detection" , Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso. "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).
Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. The Bipohysics of DNA Hybridization with Immobilized Oligonucleotide Probes. Biophysical Journal 69: pp. 2243-2255 (1995).
Chang, et al., "New Approach to Produce monosized Polymer Microcapsules by the Solute Co-diffusion Method". Langmuir, vol. 17, No. 18, pp. 5435-5439 (2001).
Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonucleoase and *Escheria coli* exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).
Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).

(56) References Cited

OTHER PUBLICATIONS

Chen, YX, et al., "Deletion of arginine codon 229 in the Rhce gene alters e and f but not c antigen expression". vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).
Cherepinsky, Vera, "On mathematical aspects of genomic analysis", Ph.D. Thesis, published Mar. 2004.
Cheung, V. G., et al., "Making and Reading Microarrays". vol. 21, pp. 15-19 (Jan. 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, p. est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quanum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/percond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).
Cruse et al., "Illustrated Dictionary of Immunology". Boca Raton: CRC Press, p. 512 (2003).
Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a smallI dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).
Decher, G., "Fuzzy Nanoassemblies: Towared Layered Polymeric Multicomposites". Science, vol. 277, pp. 1232-1237 (Aug. 29, 1997).
Denomme, G. A., et al., "High throughput multiplex single-nucloetide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.
Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.

Duggan, David J., et al., "Expression profiling using cDNA microarrays". Nature Genetics Supplement, vol. 21, pp. 10-14 (Jan. 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibility Determination. I. Description of the Algorithm. Human Immunology, vol. 63, pp. 339-352 (2002).
Dziennik, S. R., et al., "Nondiffusive mechanisms enhance protein uptake rates in ion exchange particles". PNAS, vol. 100, No. 2, pp. 420-425 (2003).
Easteal, S. "DNA Fingerprinting by PCR Amplification of HLA Genes". DNA and Criminal Justice; Human Genetics Group, John Curtin School of Medical Research, pp. 121-127 (1991).
Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligonucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al., "Rapid Development of Nucleic Acid Diagnostics", Proceedings of the IEEE 90 (11): 1708-1720 (Nov. 2002).
Fluorescent Microspheres (Tech. Note #19). Bangs Laboratories (1997).
Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).
Fowke, Keith R., et al. "Genetic analysis of human DNA recovered from minute amounts of serum or plasma". Journal of Immunological Methods, vol. 80, pp. 45-51 (1995).
Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).
Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790 (Sep. 18, 1998).

(56) References Cited

OTHER PUBLICATIONS

Gates, et al., "Photonic Crystals that can be Addressed with an External Magnetic Field". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).
Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giersig et al. Formation of ordered two-dimensional gold colloid lattices by electrophoretic deposition. J. Phys. Chem., vol. 97: 6334-6336 (Apr. 29, 1993).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al., "New types of silica-fortified magnetic nanoparticles as tools for molecular biology applications". Journal of Magnetism and Magnetic Materials, vol. 94, pp. 8-15 (1999).
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.
Gullberg, M., et al., "Cytokine detection by antibody-based proximity ligation". PNAS, vol. 101, No. 22, pp. 8420-8424 (Jun. 2004).
Guo, Zhen et al. "Oligonucleotide arrays for high-throughput SNPs detection in the MHC class I genes: HLA-B as a model system". Genome Research; vol. 12, No. 3, pp. 447-457 (Mar. 2002).
Guo, Zhen, "Direct fluorescence analysis of genetic polymorphisms . . . oligonucleotide arrays on glass supports". Nucleic Acids Research, Jul. 1994, Oxford Univ Press, pp. 5456-5465.
Gupta et al. ("Hydrogels: from controlled release to pH-responsive drug delivery" Drug Discov Today. May 15, 2002;7(10):569-79.
Gustafsdottir, S. M., "In vitro analysis of DNA—protein interactions by proximity ligation". PNAS, vol. 104, No. 9, pp. 3067-3072 (Feb. 2007).
Haab et al. Single Molecule Fluorescence Burst Detection of DNA Fragments Separated by Capillary Electrophoresis. Analytical Chemistry, vol. 67 (No. 18) : 3253-3256 (1995).
Hacis et al., "Resequencing and mutational analysis using oligonucleotide microarrays", Nature America; 21 : 42-47 (1999).
Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).
Hashimi et al., "A Flexible Array format for large-scale, rapid blood group DNA typing". Transfusion, Published Online Apr. 6, 2004, vol. 45, Issue 5, pp. 680-688 (May 2005).
Hashmi, G., et al, "Determination of 24 minor red blood cell antigens for more than 2000 blood donors by high-throughput DNA analysis". Transfusion, vol. 47, No. 4, pp. 736-747 (Apr. 2007).
Zaer, Farid, et al., "Antibody Screening by Enzyme-Linked Immunosorbent Assay Using Pooled Soluble HLA in Renal Transplant Candidates". Transplantation, vol. 63, No. 1, pp. 48-51 (Jan. 15, 1997).
Heinrich, et al., "Interleukin-6-type Cytokine Signaling through the gp 130/Jak/STAT pathway". Biochem J, vol. 334, pp. 297-314 (1998).
Helgesen, et al., "Aggregation of magnetic microspheres: experiements and simulations". Physical Review Letters, vol. 61, No. 15, pp. 1736-1739 (1998).
Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).
Hermanson, G. T., "Nucleic Acid and Oligonucleotide Modification and Conjugation". Bioconjugate Techniques, Academic Press, Chapter 17, pp. 639-671 (Jan. 15, 1996).
Yershov et al., "DNA analysis and diagnostics on oligonulceotide microchips". Proceedings of the National Academy of Sciences of the United States of America, vol. 93, No. 10, pp. 4913-4918 (May 14, 1996).
Hiller, J., et al., "Reversibly erasable nanoporous anti-reflection coatings from polyelectrolyte multilayers". Nature Materials, vol. 1, pp. 59-63 (Sep. 2002).
Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).
Hizume, et al., "Tandem repeat DNA localizing on the proximal DAPI bands of chromosomes in Larix, pinaceae". Genome, vol. 45, pp. 777-783 (2002).
Holtz, J., et al., "Intelligent Polymerized Crystalline Colloidal Array: Novel Sensor Materials", Analytical Chemistry, vol. 70, No. 4, pp. 780-791 (1998).
Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).
Huff et al., "Technical Milestone: Development of the Logical Observation Identifier Names and Codes (LOINC) Vocabulary". JAIMA, vol. 5, pp. 276-292 (1998).
Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).
Ide et al., "Synthesis and damage specificity of a novel probe for the detection of abasic sites in DNA". Biochemistry. vol. 32: 8276-8283 (1993).
Ito, Y., et al., "Patterned Immobilization of Thermoresponsive Polymer", Langmuir, vol. 13, pp. 2756-2759 (1997).
Iwayama, et al., "Optically Tunable Gelled Photonic Crystal Covering Almost the Entire Visible Light Wavelength Region", Langmuir (2002).
Jackman, R. J., et al., "Using Elastomeric Membranes as Dry Resists and for Dry Lift-Off", Langmuir, vol. 15, pp. 2973-2984 (1999).
Jeon, N. L., et al., "Patterned polymer growth on silicon surfaces using microcontact printing and surface-initiated polymerization", Applied Physics Letters, vol. 75, No. 26, pp. 4201-4203 (1999).
John C. Guatelli et al., "Isothermal, in vitro amplification of nucleic acids by a multienzyme reaction modeled after retroviral replication," Proc. Nat'l Academy of Science USA, vol. 87: pp. 1874-1878 (1990).
Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).

(56) References Cited

OTHER PUBLICATIONS

Jones et al., "Constraint, Optimization, and Hierarchy: Reviewing Stereoscopic Correspondence of Complex Features". Computer Vision and Image Understanding, vol. 65, No. 1, pp. 57-78 (1997).
Jones et al., "Dielectrophoretic liquid actuation and nanodroplet formation", Journal of Applied Physics, vol. 89, No. 2, pp. 1441-1448 (Jan. 15, 2001).
Kakabakos et al. "Immobilization of Immunoglobulins onto Surface-treated and Untreated Polystyrene Beads for Radioimmunoassays" Clin. Chem. 36 (1990), 492-496.
Kalinina, O., et al., "A core-shell Approach to Producing 3D Polymer Nanocomposites", Macromolecules, vol. 32, pp. 4122-4129 (1999).
Kamholz, et al., "Optical measurement of transverse molecular diffusion in a microchannel". Biophysical Journal, vol. 80, pp. 1967-1972 (2001).
Kamm, R. C., et al. "Nucleic Acid Concentrations in Normal Human Plasma". Clinical Chemistry, vol. 18, pp. 519-522 (1972).
Kandimalla et al., "Cyclicons" as Hybridization-Based Fluorescent Primer-Probes: Bioorganic & Medicinal Chemistry 8 (2000) 1911 to 1916.
Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).
Klintschar, et al., "Genetic variation at the STR loci D12S391 and CSF1PO in four populations from Austria, Italy, Egypt and Yemen". Forensic Sci. Int. vol. 97:37-45 (1998).
Kim, E., et al., "Polymer microstructures formed by moulding in capillaries", Nature, vol. 376, pp. 581-584 (1995).
Knipper, et al., Accession No. AF221125.1.1 on Electronic Database at NCBI (Feb. 16, 2000).
Koch et al., "PNA-Peptide Chimerae". Tetrahedron Letters, vol. 36, pp. 6933-6936 (1995).
Koh, et al., "Molding of Hydrogel Microstructures to Create Multiphenotype Cell Microarrays". Analytical Chemistry (2003).
Koh, et al., "Poly(ethylene glycol) Hydrogel Microstructures Encapsulating Living Cells". Langmuir, vol. 18, pp. 2459-2462 (2002).
Kolch. "Meaningful Relationships: The Regulation of the Ras/Raf/MEK/ERK pathway by protein interactions". Biochem J, vol. 351, pp. 289-305 (2000).
Kotov, N., et al., "Layer-by-Layer Self-Assembly of Polyelectrolyte-Semiconductor Nanoparticle Composite Films". J. Phy Chem, vol. 99, pp. 13065-13069 (1995).
Krausa et al. "A Comprehensive PCR-ssP typing system for identification of HLA-A locus alleles", Tissue Antigens, 47 (3) : 237-244 (1996).
Krsko, P., et al., "Electron-Beam Surface Patterned Poly(ethylene glycol) Microhydrogels". Langmuir, vol. 19, pp. 5618-5625 (2003).
Krutzik P.O. et al., "Fluorescent cell barcoding in flow cytometry allows high-throughput drug screening and signal profiling". Nature Methods, vol. 3, No. 5, pp. 361-368 (2006).
Kubo et al., "A Novel Sensitive and specific assay for abasic sites, the most commonly produced DNA lesion". Biochemistry, vol. 13:3703-3708 (1992).
Kumacheva, E., et al., "Three-dimensional Arrays in Polymer Nanocompositites", Advanced Materials, vol. 11, No. 3, pp. 231-234 (1999).
Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).
Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).
Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).

LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).
Lagerholm et al., "Theory for Ligand Rebinding at Cell Membrane Surfaces," Biophysical Journal (1998), vol. 74, pp. 1215-1228.
Lamb, D. J., et al., "Modification of Natural and Artificial Polymer Colloids by Topology-Controlled Emulsion Polymerization". Biomacromolecules, vol. 2, No. 2, pp. 518-525 (2001).
Lander, E. S. "The New Genomics: Global Views of Biology". Sciences, vol. 274, No. 5287, pp. 536-539 (Oct. 25, 1996).
Lander, E. S., et al., "Array of Hope". Nature Genetics Supplement, Perspective, vol. 21, pp. 3-4, (Jan. 1999).
Latour, P., et al., "Polymorphic Short Tandem Repeats for Diagnosis of the Charot-Marie-Tooth IA Duplication". Clinical Chemistry, vol. 47, pp. 829-837 (2001).
Lau, F. Y., et al., "Provision of phenotype-matched blood units: no need for pre-transfusion antibody screening", Haematologica, vol. 86, No. 7, Jul. 2001, pp. 742-748.
Lee et al. "Quantitation of residual WBCs in filtered blood components by high-throughput, real time kinetic PCR", Blood Components, transfusion, vol. 42, pp. 87-93 (Jan. 2002).
Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).
Lee, H. J., et al., "Fabricating RNA Microarrays with RNA-DNA Surface Ligation Chemistry". Analytical Chemistry, vol. 77, No. 23, pp. 7832-7837 (Dec. 1, 2005).
Lee, S., et al., "Control of Core-Shell Latex Morphology". Polymer Latexes, ACS Symposium, American Chemical Society, pp. 234-253 (1992).
Lemieux: "High throughput single nucleotide polymorphism genotyping technology" Current Genomics. vol. 1:301-311 (2000).
Lhomme et al. "Abasic DNA structure, reactivity and recognition". Biopolymers. vol. 52 : 65-83 (1999).
Li, A., et al., "Multiplexed analysis of polymorphisms in the HLA gene complex using bead array chips". Tissue Anitigens, vol. 63, pp. 518-528 (2004).
Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).
Liang, L., et al., "Temperature-sensitive membranes prepared by UV photopolymerization of N-isopropryacrylamide on a surface of porous hydrophilic polypropylene membranes", Journal of Membrane Science, vol. 162, pp. 235-246 (1999).
Liebert, M. R., et al., "Dynamics of the holes in human erythrocyte membrane ghosts". J. Biological Chemistry, vol. 257, No. 19, pp. 11660-11666 (1982).
Lin et al. "Raman Studies of Bovine Serum Albumin" . Biopolymers 15:203-218 (1976).
Lindahl et al., "Rate of depuriniation of native deoxyribonucleic acid". Biochemistry. vol. 11, No. 19: 3610-1617 (1972).
Lindahl et al., "Rate of chain breakage at apurinic sites in double-stranded deoxyribonclueic acid" Biochemistry, vol. 11, No. 19:3618-3623 (1972).
Lipshutz, R. J., et al., "High Density Synthetic Oligonucleotide Arrays". vol. 21, pp. 20-24 (Jan. 1999).
Liu, et al., "Development of a Carbon Dioxide-Base Microencapsulation Technique for Aqueous and Ethanol-Based Lateses". Langmuir (2002).
Liu, V, et al, "Three-Dimensional Photopatterning of Hydrogels Containing Living Cell". Biomedical Microdevices, vol. 4, No. 4, pp. 257-266 (2002).
Lofas, et al., "Methods for site controlled coupling to carboxymethyldextran surfaces in surface plasmon resonance sensors". Biosensors & Bioelectronics, vol. 10, pp. 813-822 (1995).
Loomans, E., et al., "Assessment of the functional affinity constant of monoclonal antibodies using an improved enzyme-linked immunosorbent assay". Journal of Immunological Methods, vol. 184, pp. 207-217 (1995).

(56) References Cited

OTHER PUBLICATIONS

Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).

Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).

Luo et al., "Emulsion Copolymerization of Butyl Acrylate with Cationic Monomer Using Interfacial Redox Initiator System". Journal of Polymer Science, vol. 39, pp. 2696-2709 (2001).

Lvov, Y, et al., "Alernate Assembly of Ordered Multilayers of SiO2 and Other Nanoparticles and Polyions". Langmuir, vol. 13, pp. 6195-6203 (1997).

MacBeath et al., "Printing proteins as microarrays for high-throughput function determination". Science, vol. 289; pp. 1760-1763 (Sep. 8, 2000).

Maldonado-Rodriguez et al., "Hybridization of glass-tethered oligonucleotide probes to . . . ", Molecular Biotechnology, vol. 11, No. 1, pp. 1-12 (1999).

Marras et al., Multiplex detection of single-nucleotide variations using molecular beacons: Genetic Analysis: Biomolecular Engineering 14 (1999) 151-156.

Marsh, S. G. E., et al., The HLA Facts Book, "HLA Typing at the DNA Level", Academic Press, Chapter 6, pp. 37-39 (2000).

Martin, M., et al. "A Method for Using Serum or Plasma as a Source of DNA for HLA Typing". Human Immunology, vol. 33, pp. 108-113 (1992).

Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.

Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).

Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).

Matthews et al., "Biochemistry: A Short Course". New York: John Wiley & Sons, Inc, p. 25 (1997).

Maxam et al., "A new method for sequencing DNA," Proc. Natl. Acad. Sci. USA. vol. 74, No. 2, pp. 560-564, Feb. 1977.

McCloskey, et al., "Magnetic Cell Separation: Characterization of Magnetophoretic Mobility". Anal. Chem., vol. 75, pp. 6868-6874 (2003).

McCloskey, et al., "Magnetophoretic Mobilities Correlate to Antibody Binidng Capacities". Cytometry, vol. 40, pp. 307-315 (2000).

Mei et al. "Genome-wide Detection of Allelic Imbalance Using Human SNPs and High-Density DNA Arrays". Genome Research. vol. 10, pp. 1126-1137 (2000).

Michael, et al., "Randomly ordered addressable high-density optical ssensor arrays". Anal. Chem, vol. 70, pp. 1242-1248 (1999).

Micheletto et al., "A simple method for the production of a two-dimensional ordered array of small latex particles". Langmuir, vol. 11, pp. 3333-3336 (1995).

Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539-1545 (May 27, 1996).

Moore, et al., "The use of magnetite-doped polymeric microspheres in calibrating cell tracking velocimetry". J. Biochem. Biophys. Methods, vol. 44, pp. 115-130 (2000).

Morag et al. "Immobilized nitro-avidin and nitro-streptavidin as reusable affinity matrices for application in avidin-biotin technology". Analytical Biochemistry. vol. 243: 257-263 (1996).

Mori, et al., Computer program to predict liklihood of finding an HLA-matched donor: Methodology, validation, and application. Biology of Blood and Marrow Transplantation, vol. 2, pp. 134-144 (1996).

Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.

Muller et al., "Gene and Haplotype Frequencies for the Loci HLA-A, HLB-B, and HLA-DR Based on Over 13,000 German Blood Donors". Human Immunology, 2003, 64: 137-151.

Mullis et al. Specific Synthesis of DNA in Vitro via a Polymerase-Catalyzed Chain Reaction Methods in Enzymology, 1987; vol. 155, pp. 335-350.

Nagarajan et al., "Identifying Spots in Microarray Images", IEEE Transactions on Nanobioscience, vol. 1, No. 2, pp. 78-84 (Jun. 2002).

Nagayama et al., "Fabrication of two-dimensional colloidal arrays". Phase Transitions, vol. 45, 185-203 (1993).

Nam, J., et a., "Colorimetric Bio-Barcode Amplification Assay for Cytokines". Anal. Chem., vol. 77, pp. 6985-6988 (2005).

Nau et al., "A Command Processor for the Determination of Specificities fro Matrices of Reactions Between Blood Cells and Antisera". Computers and Biomedical Research, vol. 10, pp. 259-269 (1977).

Nazarenko et al. (2002) Multiplexed quantitiative PCR using self-quenched primers labeled with a single fluorophore. Nucleic Acids Research, 30 (9), e37.

Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).

Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).

Nygren, "Molecular Diagnostics of Infectious Diseases" Royal Institute of Technology Department of Biotechnology, Stockholm 2000, pp. 1-68.

Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.

Okubo, and Yamashita. "Thermodynamics for the preparation of micorn-sized, monodispersed highly monomer-'absorbed' polymer particles utilizing the dynamic swelling method." Colloids and Surfaces, 1999:153-159.

Okubo et al., "Preparation of micron-size monodisperse polymer particles by seeded polymerization utilizing the dynamic monomer swelling method". Colloid and Polymer Science, vol. 269, No. 3, pp. 222-226 (1991).

Olejnik et al., "Photocleavable biotin phosphoramidite for 5'-end-labeling, purification & phosphorylation of oligonucleotides", Nucleic Acids Research 1996, vol. 24, 2:361-366.

Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).

Olson et al. "A common langauge for physical mapping of the human genome". Science, vol. 245, pp. 1434-1435 (1989).

Otero, T. F., et al., "Electrochemically initiated acrylic acid/acrylamide copolymerization", J. Electroanal. Chem., vol. 256, pp. 433-439 (1998).

Otero, T. F., et al., "Electroinitiated polymerization of acrylamide in DMG: Attempts at an interfacial model", J. Electroanal. Chem., vol. 304, pp. 153-170 (1991).

Pastinen, et al., "A System for specific, high-throughput genotyping by allele-specific primer extension on microarrays". Genome Res., vol. 10, pp. 1031-1042 (2000).

(56) References Cited

OTHER PUBLICATIONS

Peter, C., et al., "Optical DNA-sensor chip for real-time detection of hybridization events". Fresenius J. Anal. Chem, vol. 371, pp. 120-127 (Jun. 2001); Published online Springer-Verlay 2001.
Wilson, M. R., et al., "A New Microsphere-based Immunofluorescence Assay for Antibodies to Membrane-associated Antigens". Journal of Immunological Methods, vol. 107, pp. 231-237 (1988).
Peterson, et al. "Fiber Optic pH probe for physiological use". Anal. Chem. vol. 52, 864-869 (1980).
Peterson, et al., "Fiber Optic Sensors for Biomedical Applications". Science, vol. 13; pp. 123-127 (1984).
Peytavi et al., "Correlation between microarray DNA hybridization efficiency and the position of short capture probe on the target nucleic acid". Biotechniques, vol. 39, No. 1, pp. 89-96 (2005).
Pooga, M., et al., "Cell-Penetrating constructs regulate galanin receptor levels and modify pain transmission in vivo" Nature Biotechnology, vol. 16, pp. 857-861 (1998).
Pope. "Fiber optic chemical microsensors employing optically active silica microspheres". SPIE, vol. 2388; pp. 245-256 (1995).
Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.
Pregibon et al, "Magnetically and Biologically Active Bead-Patterned Hydrogels". Langmuir, vol. 22, pp. 5122-5128 (2006).
Preza, "Phase Estimation using rotational diversity for differential interference contrast microscopy". Dissertation presented to the Washington University, Server Institute of Technology, Department of Electrical Engineering; St. Louis, MO (Aug. 1998).
Proudinikov et al., "Chemical methods of DNA and RNA fluorescent labeling". Nucleic Acids Research. vol. 24, No. 22: 4535-4542 (1996).
Proudnikov , D., et al., "Immobilization of DNA in Polyacrimide Gel for the Manufacture of DNA and DNA-Oligonucleotide Microchips", Analytical Biochemistry, vol. 259, pp. 34-41 (1998).
Quon, R., et al., "Measurement of the Deformation and Adhesion of Rough Solids in Contact". J. Phys. Chem., vol. 103, pp. 5320-5327 (1999).
Rabbany et al., "Assessment of hetrogeneity in antibody displacement reactions". Anal Chem, vol. 69, pp. 175-182 (1997).
Radtchecnko et al., "Core-shell structures formed by the solvent-controlled precipitation of luminescent ScTe nanocrystals on latex spheres". Advanced Materials, vol. 13, No. 22, pp. 1684-1687 (2001).
Radtkey et al., "Rapid, high-fidelity analysis of simple sequence repeats on an electronically active DNA microchip". Nucleic Acids Research, vol. 28, No. 7, p. e17 (2000).
Ramsay, G., "DNA Chips: State-of-the-Art". Nature Biotechnology, vol. 16, pp. 40-44 (Jan. 1998).
Reddy et al., "Determination of the Magnetic Susceptibility of Labeled Particles by Video Imaging". Chemical Engineering Science, vol. 51, No. 6, pp. 947-956 (1996).
Reid M.E., et al., "Novel Dombrock blood group genetic variants . . . ", Blood (ASH Annual Meeting Abstract) 2004, 104: Abstract 383.
Relogio, A. et al., "Optimization of oligonucleotide-based DNA microarrays", Nucl. Acids Res., vol. 30, e51, pp. 1-10 (2002).
Richardson et al., "The use of coated paramagnetic particles as a physical label in a magneto-immunassay". Biosensors & Bioelectronics, vol. 16, pp. 989-993 (2001).
Richardson, et al., "A novel measuring system for the determination of paramagnetic particle lables for use in magneto-immunoassays". Biosensors & Bioelectronics, vol. 16, pp. 1127-1132 (2001).
Richetti et al., "Two-dimensional aggregations and crystallization of a colloidal suspension of latex spjeres", J. Physique Letter. vol. 45, pp. L-1137 to L-1143 (1984).
Righetti, P. G., et al., "Electrophoresis gel media: the state of the art", J. Chromatogr B., Biomed Sci Appl, vol. 699, No. 1-2, pp. 63-75 (Oct. 10, 1997).

Roberts et al. "Patterned magnetic bar array for high-thoughput DNA detection" IEEE Transaction on Magnetics. vol. 40, No. 4: 3006-3008 (2004).
Rubina et al, "Hydrogel drop microchips with immobilized DNA: properties and methods for large-scale production". Analytical Biochemistry, vol. 325, pp. 92-106 (2004).
Rudzinski, et al., "pH-sensitive acrylic-based copolymeric hydrogels for the controlled release of a pesticide and a micronutrient". Journal of Applied Polymer Science, vol. 87, pp. 394-403 (2003).
Sacchetti, et al. "Efficiency of Two Different Nine-Loci Short Tandem Repeat Systems for DNA Typing Purposes". Clinical Chemistry, vol. 45, No. 2, pp. 178-183 (1999).
Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).
Sambrook et al., "Precipitation with Ethanol or Isopropanol", Concentrating Nucleic Aicds, Molecular Cloning vol. 3, pp. E3-E4 and E.10-E.15 (1989).
Sano, T, et al., "Immuno-PCR: Very Senisitive Antigen Detection by Means of Specific Antibody-DNA Conjugates". Science, vol. 258, pp. 120-122 (Oct. 2, 1992).
Santa Lucia, J. Jr., "A unified view of polymer, dumbbell, and oligonucleotide DNA nearest-neighbor thermodynamics". PNAS USA, vol. 95, pp. 1460-1465 (1998).
Schaid et al., "Score Tests for Association between traits and Haplotypes when Linkage Phase is Ambiguous", American Journal of Genetics. vol. 70, pp. 425-434 (2002).
Schena et al., "Quantitative Monitoring of Gene Expression Patterns with a Complementary DA Microarray". Science, vol. 270, pp. 467-470 (1995).
Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).
Schreiber, G. B., et al., "Increasing Blood Availability by changing Donation Patterns". Transfusion, vol. 43, pp. 591-597 (2003).
Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).
Schumaker, et al., "Mutation Detection by solid phase primer extension", Human Mutation 7:346-354 (1996).
Wilson et al., "A generalized method for magnetite nanoparticle steric stabilization utilizing block copolymers containing carboxylic acids". European Cells and Materials, vol. 2, Suppl 2, pp. 202-209 (2002).
Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5.
Scillian, James J., et al., "Early Detection of Antibodies Against rDNA-Produced HIV Proteins with a Flow Cytometric Assay". Clinical Chemistry, vol. 40, No. 3, pp. 420-425 (1994).
Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).
S. Dubiley et al., "Polymorphism Analysis and Gene Detection by minsequencing on an array of gel immobilized primers." Nucleic Acids Research, 1999;i-vi. vol. 27, No. 16.
S. Ebel et al. "Very Stable Mismatch Duplexes: Structural and Thermodynamic Studies on G-A Mismatches in DNA" Biochemistry 31:12083-86 (1992).
Seeman, P., et al., "Structure of Membrane Holes in Osmotic and Saponin Hemolysis"; The Journal of Cell Biology, vol. 56; pp. 519-527 (1973).
Sehgal et al. "A method for the high effieiency of water-soluble carbodiimide-mediated amidation". Analytical Biochemistry. vol. 218:87-91 (1994).
Seltsam, et al., Systematic analysis of the ABO gene diversity within exons 6 and 7 by PCR screening reveals new ABO alleles, Transfusion, vol. 43, pp. 428-439 (2003).

(56) References Cited

OTHER PUBLICATIONS

Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases". Science, vol. 267:476-483 (1995).
Seul et al., "Scale transformation of magnetic bubble arrays: coupling of topological disorder and polydispersity". Science, vol. 262: 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham, P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPs)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "Red: A Red-Cell Antibody Identification Expert Module". Journal of Medical Systems, vol. 9, No. 3, pp. 121-138 (1985).
Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review", Transfusion 43: 1126-1132 (2003).
Steemers, F.J. (2000) Screening unlabeled DNA targets with randomly ordered fiber-optic gene arrays. Nat. Biotechnol., 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).
Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).

Sukhishvilli, S.A. et al. "Adsorption of human serum albumin: Dependence on molecular architecture of the oppositely charged surface" J. Chem. Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucleotide Polymorphisms", Human Mutation 13:1-10 (1999).
Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genone-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al., "Mechanical instability of gels at the phase transition", Nature, vol. 325, pp. 796-798 (1987).
Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," Clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model for the effects of time and temperature onthe gelation time of BSA gels." Macromolecules. vol. 30:4845-4854 (1997).
Tokumasu F. et al., Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).
Trau et al., "Field-induced layering of colloidal crystal", Science, vol. 272; pp. 706-709 (1996).
Trang D.T.X. et al. "One step concentration of malarial parasite-infected red blood cells and removal of contaminating white blood cells", Malaria Journal (2004) pp. 1-7 from http://www.malariajournal.com/content/3/1/7.
Trau et al., "Nanoencapsulated microcrystalline particles for superamplified biochemical assays". Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).
Tyagi et al., Molecular Beacons: Probes that Flouresce upon Hybridization, Nature Biotechnology vol. 14, pp. 303-308 (1996).
Vainrub, A., et al., "Sensitive quantitative nucleic acid detection using oligonucleotide microarrays". Journal of the American Chemical Society, vol. 125, No. 26, pp. 7798-7799, (Jun. 2003).
Van Kempen, et al., "Mean and Variance of Ratio Estimators Used in Fluorescence Ratio Imaging". Cytometry, vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).

(56) References Cited

OTHER PUBLICATIONS

Vasiliskov, A. V., et al., "Fabrication of Microarray of Gel-Immobilized Compounds on a Chip by Copolymerization". BioTechniques, vol. 27, pp. 592-606 (Sep. 1999).
Vaynberg et al. "Structure and extent of absorbed gelatin on acrylic latex and polystyrene collodial particles". Journal of Colloid and Interface Science. vol. 205:131-140 (1998).
Vet, J.A.M. (1999) Multiplex detection of four pathogenic retroviruses using molecular beacon. Proc. Natl. Acad. Sci. USA, 96, 6394-6399.
Vilain. "CYPs, SNPs, and Molecular Diagnosis in the Postgenomic Era". Clinical Chemistry, vol. 44, pp. 2403-2404 (1998).
Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).
Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).
Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).
Weinfeld et al., "Selective hydrolysis by exo- and endonucleases of phosphodiester bonds adjacent to an apurinic site". Nucleic Acids Research, vol. 17, No. 10: 3735-3744 (1989).
Weissenbach et al. "A Second generation linkage map of the human genome". Nature, vol. 359, pp. 794-801 (1992).
Wen, et al., "Planar Magnetic Colloidal Crystals". Physical Review Letters, vol. 85, No. 25, pp. 5464-5467 (2000).
Wiedmann, M., et al., Ligase Chain Reaction (LCR)—Overview and Applications, PCR Methods and Applications, Genome Research, vol. 3, pp. s51-s64 (1994).
Yeang et. al. Molecular classification of multiple tumor types. Bioinformatics vol. 17 Suppl. 1, pp. s316-s322 (2001).
J.F. Chapman et al., Working Party of the BCSH: "Guidelines for compatibility procedures in blood transfusion laboratories", Transfusion Medicine, vol. 14, pp. 59-73 (2004).
Yamashita et al., "Thermodynamics for the preparation of micron-sized, monodispersed highly monomer absorbed polymer particles utilizing the dynamic selling method". Colloids and Surfaces, vol. 153, pp. 153-159 (1999).
Yao et al., "Molecular-beacon-based array for sensitive DNA analysis". Analytical Biochemistry, vol. 331, pp. 216-223 (2004).
Fukuda et al., "Noncontact manipulation of DNA molecule 1. Transportation of DNA molecule by dielectric force". Nippon Kikai Gakkai Ronbunshu, vol. 62: 2765-2772 (1996).
Friedli, Interaction of SWP with Bovine Serum Albumin (BSA) and Soluble Wheat Protein (SWP) (7 pages) downloaded http://www.friedli.com/research/PhD/chapter5a.html.
Hermanson, Greg T., "Zero Length Cross-Linkers"; Bioconjugate Techniques; Academic Press, pp. 170-176 (1996).
Hermanson, Greg T., "Bioconjugate Techniques", Bioconjugate Techniques; Academic Press, San Diego, 430-33, (1996).
Tobitani et al. "Heat-induced gelation of globular proteins 2. Effect of environmental factors on single-component and mixed-protein gels," Macromolecules; vol. 30: 4855-4862 (1997).
Wittemann et al., "Interaction of Proteins with Spherical Polyelectrolyte Brushes" (Polyer Institute, University of Karlsruhe, Karlsruhe, Germany) Poster Oct. 2001.
Pastinen et al., (Genome Res. Jul. 10, 2000 (7): 1031-42) teaches microarray-based allele-specific primer extension.
Fan et al., (Genome Res. Jun. 2000:10 (6):853-60).
Chen et al., (Genome Res. 20000 Apr:10 (4):549-57); teaches a method of multiplex single nucleotide polymorphism (SNP) detection.
Shumaker et al.,"Mutation Detection by Solid Phase Primer Extension", Human Mutation 7: 346-354 (1996).
Kennedy et al., Genetic diversity of HLA; New Technique in HLA Typing; HLA Class I DNA typing using sequence specific olignuceotide probes (SSOP).
Hacia, "Resequencing and Mutational Analysis Using Oligonucleotide Microarrays", Nature America; 21:42-47 (1999).
Pastinen et al., "Minisequencing: A specific Tool for DNA Analysis and Diagonstics on Oligonucleotide Arrays", Genome Research, Cold Spring Harbor Laboratory Press, 7:606-14 (1997).
A.C. Syvanen, "From Gels to Chip: "Minisequencing" Primer Extension for Analysis of Pont Mutations and Single Nucleotide Polymorphisms", Human Mutation, 13:1-10 (1999).
Cai et al., "Flow Cytometry-Based Minisequencing: A New Platform for High-Throughout Single-Nucleotide Polymorphism Scoring", Genomics 66:135-143 (2000).
M. Bunce et al., "Phototyping: Comprehensive DNA typing for HLA-A,B,C, DRB3, DRB4, DRB5 & DQB1 by PCR with 144 primer mixes utilizing sequence-specific primers (PCR-SS)", Tissue Antigens 46:355-367 (1995).
M. Bunce et al., "Comprehensive, serologically equivalent DNA typing for HLA-B by PCR using sequence specific primers (PCR-SSP)", Tissue Antigens 45:81-90 (1995).
Herman, J.G. et al. (Sep. 3, 1996). "Methylation-specific PCR: a novel PCR assay for methylation status of CpG islands," *PNAS USA* 93(18):9821-9826.
Bernardo, M.C. et al. (Mar. 1998). "Allele-specific HLA-B*15 typing by PCR-SSP and its application to four distinct ethnic populations," *Tissue Antigens* 51(3)293-300.
European Search Report for EP13189483.4 dated Mar. 25, 2014.
Beaudet, L. et al. (Apr. 2001). "Homogeneous assays for single-nucleotide polymorphism typing using AlphaScreen," *Genome Res* 11(4):600-608.
J.D. Bignon et al., "HLA DNA class II typing by PCR-SSOP:12th International Histocompatibility Workshop experience", Allele and Haplotype Societies.
L.J. Kennedy, et al. "HLA Class I DNA typing sequence specific oligonucleotide probes (SSOP)." Genetic diversity of HLA; New Technologies in HLA typing.
Okimoto, R. et al. (Jul. 1996). "Improved PCR amplification of multiple specific alleles (PAMSA) using internally mismatched primers," *Biotechniques* 21(1):20-2, 24, 26.
Okano, K. et al. (Dec. 1998). "Characteristics of selective polymerase chain reaction (PCR) using two-base anchored primers and improvement of its specificity," *Electrophoresis* 19(18):3071-3078.
Bernard, P.S. (Sep. 10, 1999). "Color multiplexing hybridization probes using the apolipoprotein E locus as a model system for genotyping," *Anal Biochem* 273(2):221-228.

\* cited by examiner

|  | | Primer1 | Primer2 | Primer3 | Primer4 |
|---|---|---|---|---|---|
| Combination 1 | Alele A | + |  | + |  |
|  | Alele B |  | + |  | + |
|  | Total | + | + | + | + |
| Combination 2 | Alele C | + | + |  |  |
|  | Alele D |  |  | + | + |
|  | Total | + | + | + | + |

Fig. 4

Class I B Exon3

SEQUENCE LISTING

<160> NUMBER OF SEQ ID NOS: 208

<210> SEQ ID NO 1
<211> LENGTH: 20
<212> TYPE: DNA
<213> ORGANISM: Homo sapiens

<400> SEQUENCE: 1
ttcttgtggc agcttaagtt                                                    20

<210> SEQ ID NO 2
<211> LENGTH: 20
<212> TYPE: DNA
<213> ORGANISM: Homo sapiens

<400> SEQUENCE: 2
ttcttggagt actctacgtc                                                    20

<210> SEQ ID NO 3
<211> LENGTH: 20
<212> TYPE: DNA
<213> ORGANISM: Homo sapiens

-continued

```
<400> SEQUENCE: 3
ttcttggagc aggttaaaca                                                  20

<210> SEQ ID NO 4
<211> LENGTH: 20
<212> TYPE: DNA
<213> ORGANISM: Homo sapiens

<400> SEQUENCE: 4
ttcttggagc aggttaaacc                                                  20

<210> SEQ ID NO 5
<211> LENGTH: 20
<212> TYPE: DNA
<213> ORGANISM: Homo sapiens

<400> SEQUENCE: 5
ttcctgtggc agggtaagta                                                  20

<210> SEQ ID NO 6
<211> LENGTH: 20
<212> TYPE: DNA
<213> ORGANISM: Homo sapiens

<400> SEQUENCE: 6
ttcctgtggc agggtaaata                                                  20

<210> SEQ ID NO 7
<211> LENGTH: 20
<212> TYPE: DNA
<213> ORGANISM: Homo sapiens

<400> SEQUENCE: 7
ttcttggagt actctacggg                                                  20

<210> SEQ ID NO 8
<211> LENGTH: 20
<212> TYPE: DNA
<213> ORGANISM: Homo sapiens

<400> SEQUENCE: 8
ttcttggagt actctagggg                                                  20

<210> SEQ ID NO 9
<211> LENGTH: 20
<212> TYPE: DNA
<213> ORGANISM: Homo sapiens

<400> SEQUENCE: 9
ttcttggagt actctacggc                                                  20

<210> SEQ ID NO 10
<211> LENGTH: 20
<212> TYPE: DNA
<213> ORGANISM: Homo sapiens

<400> SEQUENCE: 10
ttcttggagt actctatggg                                                  20

<210> SEQ ID NO 11
<211> LENGTH: 20
<212> TYPE: DNA
<213> ORGANISM: Homo sapiens
```

```
<400> SEQUENCE: 11
ttcttgaagc aggataagtt                                                  20

<210> SEQ ID NO 12
<211> LENGTH: 20
<212> TYPE: DNA
<213> ORGANISM: Homo sapiens

<400> SEQUENCE: 12
ttcttggagg aggttaagtt                                                  20

<210> SEQ ID NO 13
<211> LENGTH: 20
<212> TYPE: DNA
<213> ORGANISM: Homo sapiens

<400> SEQUENCE: 13
ttcttggagc aggctacaca                                                  20

<210> SEQ ID NO 14
<211> LENGTH: 20
<212> TYPE: DNA
<213> ORGANISM: Homo sapiens

<400> SEQUENCE: 14
ttcttggagt tccttaagtc                                                  20

<210> SEQ ID NO 15
<211> LENGTH: 20
<212> TYPE: DNA
<213> ORGANISM: Homo sapiens

<400> SEQUENCE: 15
ttcctgtggc agcctaagag                                                  20

<210> SEQ ID NO 16
<211> LENGTH: 20
<212> TYPE: DNA
<213> ORGANISM: Homo sapiens

<400> SEQUENCE: 16
ttcttggagc tgcgtaagtc                                                  20

<210> SEQ ID NO 17
<211> LENGTH: 20
<212> TYPE: DNA
<213> ORGANISM: Homo sapiens

<400> SEQUENCE: 17
ttcttggagc tgtgtaagtc                                                  20

<210> SEQ ID NO 18
<211> LENGTH: 20
<212> TYPE: DNA
<213> ORGANISM: Homo sapiens

<400> SEQUENCE: 18
ttctcggagc tgcgtaagtc                                                  20

<210> SEQ ID NO 19
<211> LENGTH: 20
<212> TYPE: DNA
```

<213> ORGANISM: Homo sapiens

<400> SEQUENCE: 19
ttcttggagc tgcttaagtc                                           20

<210> SEQ ID NO 20
<211> LENGTH: 20
<212> TYPE: DNA
<213> ORGANISM: Homo sapiens

<400> SEQUENCE: 20
ttcttgcagc tgcttaagtc                                           20

<210> SEQ ID NO 21
<211> LENGTH: 20
<212> TYPE: DNA
<213> ORGANISM: Homo sapiens

<400> SEQUENCE: 21
ttcttggagc aggctaagtg                                           20

<210> SEQ ID NO 22
<211> LENGTH: 20
<212> TYPE: DNA
<213> ORGANISM: Homo sapiens

<400> SEQUENCE: 22
ttcttgcagc aggataagta                                           20

<210> SEQ ID NO 23
<211> LENGTH: 20
<212> TYPE: DNA
<213> ORGANISM: Homo sapiens

<400> SEQUENCE: 23
ttcttggagt actctacgtc                                           20

<210> SEQ ID NO 24
<211> LENGTH: 20
<212> TYPE: DNA
<213> ORGANISM: Homo sapiens

<400> SEQUENCE: 24
ttcttggagt gccttaagtc                                           20

<210> SEQ ID NO 25
<211> LENGTH: 20
<212> TYPE: DNA
<213> ORGANISM: Homo sapiens

<400> SEQUENCE: 25
ttcttggagc tgcgtaagtc                                           20

<210> SEQ ID NO 26
<211> LENGTH: 20
<212> TYPE: DNA
<213> ORGANISM: Homo sapiens

<400> SEQUENCE: 26
ttcttggagc tgtgtaagtc                                           20

<210> SEQ ID NO 27
<211> LENGTH: 20

<212> TYPE: DNA
<213> ORGANISM: Homo sapiens

<400> SEQUENCE: 27
ttctcggagc tgcgtaagtc                                               20

<210> SEQ ID NO 28
<211> LENGTH: 20
<212> TYPE: DNA
<213> ORGANISM: Homo sapiens

<400> SEQUENCE: 28
ttcttggagc tgcttaagtc                                               20

<210> SEQ ID NO 29
<211> LENGTH: 20
<212> TYPE: DNA
<213> ORGANISM: Homo sapiens

<400> SEQUENCE: 29
ttcttgcagc tgcttaagtc                                               20

<210> SEQ ID NO 30
<211> LENGTH: 20
<212> TYPE: DNA
<213> ORGANISM: Homo sapiens

<400> SEQUENCE: 30
ttcttgtggc agcttaagtt                                               20

<210> SEQ ID NO 31
<211> LENGTH: 20
<212> TYPE: DNA
<213> ORGANISM: Homo sapiens

<400> SEQUENCE: 31
ttcttgaagc aggataagtt                                               20

<210> SEQ ID NO 32
<211> LENGTH: 20
<212> TYPE: DNA
<213> ORGANISM: Homo sapiens

<400> SEQUENCE: 32
ttcttggagg aggttaagtt                                               20

<210> SEQ ID NO 33
<211> LENGTH: 20
<212> TYPE: DNA
<213> ORGANISM: Homo sapiens

<400> SEQUENCE: 33
ttcttggagc aggttaaaca                                               20

<210> SEQ ID NO 34
<211> LENGTH: 20
<212> TYPE: DNA
<213> ORGANISM: Homo sapiens

<400> SEQUENCE: 34
ttcttggagc aggctacaca                                               20

<210> SEQ ID NO 35

```
<211> LENGTH: 20
<212> TYPE: DNA
<213> ORGANISM: Homo sapiens

<400> SEQUENCE: 35
ttcttggagc aggttaaacc                                               20

<210> SEQ ID NO 36
<211> LENGTH: 20
<212> TYPE: DNA
<213> ORGANISM: Homo sapiens

<400> SEQUENCE: 36
ttcctgtggc agggtaagta                                               20

<210> SEQ ID NO 37
<211> LENGTH: 20
<212> TYPE: DNA
<213> ORGANISM: Homo sapiens

<400> SEQUENCE: 37
ttcttgcagc aggataagta                                               20

<210> SEQ ID NO 38
<211> LENGTH: 20
<212> TYPE: DNA
<213> ORGANISM: Homo sapiens

<400> SEQUENCE: 38
ttcctgtggc agggtaaata                                               20

<210> SEQ ID NO 39
<211> LENGTH: 20
<212> TYPE: DNA
<213> ORGANISM: Homo sapiens

<400> SEQUENCE: 39
ttcttggagt actctacggg                                               20

<210> SEQ ID NO 40
<211> LENGTH: 20
<212> TYPE: DNA
<213> ORGANISM: Homo sapiens

<400> SEQUENCE: 40
ttcttggagt actctagggg                                               20

<210> SEQ ID NO 41
<211> LENGTH: 20
<212> TYPE: DNA
<213> ORGANISM: Homo sapiens

<400> SEQUENCE: 41
ttcttggagt actctatggg                                               20

<210> SEQ ID NO 42
<211> LENGTH: 20
<212> TYPE: DNA
<213> ORGANISM: Homo sapiens

<400> SEQUENCE: 42
ttcttggagt actctacggc                                               20
```

-continued

<210> SEQ ID NO 43
<211> LENGTH: 20
<212> TYPE: DNA
<213> ORGANISM: Homo sapiens

<400> SEQUENCE: 43
ttcctgtggc agcctaagag                                              20

<210> SEQ ID NO 44
<211> LENGTH: 20
<212> TYPE: DNA
<213> ORGANISM: Homo sapiens

<400> SEQUENCE: 44
ttcttggagc aggctaagtg                                              20

<210> SEQ ID NO 45
<211> LENGTH: 20
<212> TYPE: DNA
<213> ORGANISM: Homo sapiens

<400> SEQUENCE: 45
ttcttggagc tgcttaagtc                                              20

<210> SEQ ID NO 46
<211> LENGTH: 20
<212> TYPE: DNA
<213> ORGANISM: Homo sapiens

<400> SEQUENCE: 46
ttcttggagt tccttaagtc                                              20

<210> SEQ ID NO 47
<211> LENGTH: 20
<212> TYPE: DNA
<213> ORGANISM: Homo sapiens

<400> SEQUENCE: 47
ttcttggagc tgcgtaagtc                                              20

<210> SEQ ID NO 48
<211> LENGTH: 20
<212> TYPE: DNA
<213> ORGANISM: Homo sapiens

<400> SEQUENCE: 48
ttcttggagc tgtgtaagtc                                              20

<210> SEQ ID NO 49
<211> LENGTH: 20
<212> TYPE: DNA
<213> ORGANISM: Homo sapiens

<400> SEQUENCE: 49
ttctcggagc tgcgtaagtc                                              20

<210> SEQ ID NO 50
<211> LENGTH: 20
<212> TYPE: DNA
<213> ORGANISM: Homo sapiens

<400> SEQUENCE: 50
ttcttgcagc tgcttaagtc                                              20

<210> SEQ ID NO 51
<211> LENGTH: 17
<212> TYPE: DNA
<213> ORGANISM: Homo sapiens

<400> SEQUENCE: 51
gacatcctgg aagacga                                                17

<210> SEQ ID NO 52
<211> LENGTH: 17
<212> TYPE: DNA
<213> ORGANISM: Homo sapiens

<400> SEQUENCE: 52
gacttcctgg aagacga                                                17

<210> SEQ ID NO 53
<211> LENGTH: 17
<212> TYPE: DNA
<213> ORGANISM: Homo sapiens

<400> SEQUENCE: 53
gacctcctgg aagacga                                                17

<210> SEQ ID NO 54
<211> LENGTH: 12
<212> TYPE: DNA
<213> ORGANISM: Homo sapiens

<400> SEQUENCE: 54
agccagaagg ac                                                     12

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
aaggacatcc tggaagacg                                              19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
aaggacatcc tggaagaca                                              19

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
ataaccagga ggagttcc                                               18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 58
ataaccagga ggagttcg                                                  18

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 59
gtcgaagcgc aggaactcct cctggttatg gaa                                 33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 60
gtcgaagcgc acgaactcct cctggttata gaa                                 33

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 61
ggcccgctcg tcttccagga tgtccttctg gct                                 33

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 62
ggcccgcttg tcttccagga tgtccttctg gct                                 33

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
gatccttcgt gtccccacag cacg                                           24

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gccgctgcac tgtgaagctc tc                                        22

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 65
acggagcggg tgcggttg                                             18

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic probe

<400> SEQUENCE: 66
gctgtcgaag cgcacgg                                              17

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 67
cgctgtcgaa gcgcacgtt                                            19

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 68
gttatggaag tatctgtcca ggt                                       23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 69
acgtttcttg gagcaggtta aac                                       23

<210> SEQ ID NO 70

<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
cgtttcctgt ggcagggtaa gtata                                          25

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
tcgctgtcga agcgcacga                                                 19

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
cgtttcttgg agtactctac ggg                                            23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
tctgcagtag gtgtccacca                                                20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
cacgtttctt ggagctgcg                                                 19

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
ggagtaccgg gcggtgag                                                  18

<210> SEQ ID NO 76
<211> LENGTH: 23

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
gtgtctgcag taattgtcca cct                                          23

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
ctgttccagg actcggcga                                               19

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
ctctccacaa ccccgtagtt gta                                          23

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
cgtttcctgt ggcagcctaa ga                                           22

<210> SEQ ID NO 80
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
caccgcggcc cgcgc                                                   15

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
gctgtcgaag cgcaagtc                                                18

<210> SEQ ID NO 82
<211> LENGTH: 18
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 82
gctgtcgaag cgcacgta                                                   18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
aaaaaaaaaa aaaaaaaa                                                   18

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
gctgtcgaag cgcacgg                                                    17

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
tcgctgtcga agcgcacga                                                  19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
cgctgtcgaa gcgcacgtt                                                  19

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
gctgtcgaag cgcaagtc                                                   18

<210> SEQ ID NO 88
<211> LENGTH: 18
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 88
gctgtcgaag cgcacgta                                                  18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
cactccacgc acgtgcca                                                  18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
gcgcaggtcc tcgttcaa                                                  18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
ctccaggtag gctctcaa                                                  18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
ctccaggtag gctctctg                                                  18

<210> SEQ ID NO 93
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
gcccgtccac gcaccg                                                    16

<210> SEQ ID NO 94
<211> LENGTH: 17
<212> TYPE: DNA
<213> ORGANISM: Artificial Sequence
<220> FEATURE:

-continued

<223> OTHER INFORMATION: Description of Artificial Sequence: Synthetic
      probe

<400> SEQUENCE: 94
ggtatctgcg gagcccg                                                    17

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
catccaggta ggctctcaa                                                  19

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
gccggagtat tgggacga                                                   18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
tggatagagc aggagggt                                                   18

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
gaccaggaga cacggaata                                                  19

<210> SEQ ID NO 99
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ccgcgcgctc cagcgtg                                                    17

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic -continued probe

<400> SEQUENCE: 100
ccactccatg aggtatttcc                                                   20

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
ctccaacttg cgctggga                                                     18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
cgccacgagt ccgaggaa                                                     18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
gtcgtaggcg tcctggtc                                                     18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
taccagcgcg ctccagct                                                     18

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
agcaggaggg gccggaa                                                      17

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 106
cgtcgcagcc atacatcca                                                  19

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
gcgccgtgga tagagcaa                                                   18

<210> SEQ ID NO 108
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
gccgcgagtc cgaggac                                                    17

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
gaccggaaca cacagatctt                                                 20

<210> SEQ ID NO 110
<211> LENGTH: 21
<212> TYPE: DNA
<213> ORGANISM: Homo sapiens

<400> SEQUENCE: 110
cccctaaata taaaaagatt c                                               21

<210> SEQ ID NO 111
<211> LENGTH: 21
<212> TYPE: DNA
<213> ORGANISM: Homo sapiens

<400> SEQUENCE: 111
cccctaaata taaaaagatt t                                               21

<210> SEQ ID NO 112
<211> LENGTH: 19
<212> TYPE: DNA
<213> ORGANISM: Homo sapiens

<400> SEQUENCE: 112
attctcatct ccattccaa                                                  19

<210> SEQ ID NO 113
<211> LENGTH: 19
<212> TYPE: DNA
<213> ORGANISM: Homo sapiens
```

<400> SEQUENCE: 113
attctcatct ccattccag                                                    19

<210> SEQ ID NO 114
<211> LENGTH: 20
<212> TYPE: DNA
<213> ORGANISM: Homo sapiens

<400> SEQUENCE: 114
tgtgtgcaag gaagtattac                                                   20

<210> SEQ ID NO 115
<211> LENGTH: 20
<212> TYPE: DNA
<213> ORGANISM: Homo sapiens

<400> SEQUENCE: 115
tgtgtgcaag gaagtattaa                                                   20

<210> SEQ ID NO 116
<211> LENGTH: 20
<212> TYPE: DNA
<213> ORGANISM: Homo sapiens

<400> SEQUENCE: 116
tagataaatc gcgatagagc                                                   20

<210> SEQ ID NO 117
<211> LENGTH: 20
<212> TYPE: DNA
<213> ORGANISM: Homo sapiens

<400> SEQUENCE: 117
tagataaatc gcgatagagt                                                   20

<210> SEQ ID NO 118
<211> LENGTH: 19
<212> TYPE: DNA
<213> ORGANISM: Homo sapiens

<400> SEQUENCE: 118
taaatcaata ggtacatac                                                    19

<210> SEQ ID NO 119
<211> LENGTH: 19
<212> TYPE: DNA
<213> ORGANISM: Homo sapiens

<400> SEQUENCE: 119
taaatcaata ggtacataa                                                    19

<210> SEQ ID NO 120
<211> LENGTH: 20
<212> TYPE: DNA
<213> ORGANISM: Homo sapiens

<400> SEQUENCE: 120
atggtggtga atattttccg                                                   20

<210> SEQ ID NO 121
<211> LENGTH: 20
<212> TYPE: DNA

```
<213> ORGANISM: Homo sapiens

<400> SEQUENCE: 121
atggtggtga atattttcca                                              20

<210> SEQ ID NO 122
<211> LENGTH: 21
<212> TYPE: DNA
<213> ORGANISM: Homo sapiens

<400> SEQUENCE: 122
attgccgagt gaccgccatg c                                            21

<210> SEQ ID NO 123
<211> LENGTH: 21
<212> TYPE: DNA
<213> ORGANISM: Homo sapiens

<400> SEQUENCE: 123
attgccgagt gaccgccatg g                                            21

<210> SEQ ID NO 124
<211> LENGTH: 21
<212> TYPE: DNA
<213> ORGANISM: Homo sapiens

<400> SEQUENCE: 124
cacagataaa aacaccacaa a                                            21

<210> SEQ ID NO 125
<211> LENGTH: 20
<212> TYPE: DNA
<213> ORGANISM: Homo sapiens

<400> SEQUENCE: 125
cacagataaa aacaccacaa                                              20

<210> SEQ ID NO 126
<211> LENGTH: 19
<212> TYPE: DNA
<213> ORGANISM: Homo sapiens

<400> SEQUENCE: 126
cacagataaa aacaccaca                                               19

<210> SEQ ID NO 127
<211> LENGTH: 20
<212> TYPE: DNA
<213> ORGANISM: Homo sapiens

<400> SEQUENCE: 127
tccagtggat ccagcaaccg                                              20

<210> SEQ ID NO 128
<211> LENGTH: 20
<212> TYPE: DNA
<213> ORGANISM: Homo sapiens

<400> SEQUENCE: 128
tccagtggat ccagcaacct                                              20

<210> SEQ ID NO 129
<211> LENGTH: 19
```

```
<212> TYPE: DNA
<213> ORGANISM: Homo sapiens

<400> SEQUENCE: 129
cataggaaac accaaagat                                                19

<210> SEQ ID NO 130
<211> LENGTH: 16
<212> TYPE: DNA
<213> ORGANISM: Homo sapiens

<400> SEQUENCE: 130
cataggaaac accaaa                                                   16

<210> SEQ ID NO 131
<211> LENGTH: 16
<212> TYPE: DNA
<213> ORGANISM: Homo sapiens

<400> SEQUENCE: 131
cataggaaac accaat                                                   16

<210> SEQ ID NO 132
<211> LENGTH: 20
<212> TYPE: DNA
<213> ORGANISM: Homo sapiens

<400> SEQUENCE: 132
ctgcaaactt ggagatgtcc                                               20

<210> SEQ ID NO 133
<211> LENGTH: 20
<212> TYPE: DNA
<213> ORGANISM: Homo sapiens

<400> SEQUENCE: 133
ctgcaaactt ggagatgtct                                               20

<210> SEQ ID NO 134
<211> LENGTH: 15
<212> TYPE: DNA
<213> ORGANISM: Homo sapiens

<400> SEQUENCE: 134
ttcttgctcg ttgac                                                    15

<210> SEQ ID NO 135
<211> LENGTH: 15
<212> TYPE: DNA
<213> ORGANISM: Homo sapiens

<400> SEQUENCE: 135
ttcttgctcg ttgat                                                    15

<210> SEQ ID NO 136
<211> LENGTH: 18
<212> TYPE: DNA
<213> ORGANISM: Homo sapiens

<400> SEQUENCE: 136
taaagaaatt cttgctcg                                                 18

<210> SEQ ID NO 137
```

```
<211> LENGTH: 18
<212> TYPE: DNA
<213> ORGANISM: Homo sapiens

<400> SEQUENCE: 137
taaagaaatt cttgctca                                                    18

<210> SEQ ID NO 138
<211> LENGTH: 21
<212> TYPE: DNA
<213> ORGANISM: Homo sapiens

<400> SEQUENCE: 138
accaataatt agttattcac c                                                21

<210> SEQ ID NO 139
<211> LENGTH: 21
<212> TYPE: DNA
<213> ORGANISM: Homo sapiens

<400> SEQUENCE: 139
accaataatt agttattcac g                                                21

<210> SEQ ID NO 140
<211> LENGTH: 19
<212> TYPE: DNA
<213> ORGANISM: Homo sapiens

<400> SEQUENCE: 140
gtgtgattcc accttctcc                                                   19

<210> SEQ ID NO 141
<211> LENGTH: 19
<212> TYPE: DNA
<213> ORGANISM: Homo sapiens

<400> SEQUENCE: 141
gtgtgattcc accttctca                                                   19

<210> SEQ ID NO 142
<211> LENGTH: 19
<212> TYPE: DNA
<213> ORGANISM: Homo sapiens

<400> SEQUENCE: 142
aggtattcaa agaacatac                                                   19

<210> SEQ ID NO 143
<211> LENGTH: 19
<212> TYPE: DNA
<213> ORGANISM: Homo sapiens

<400> SEQUENCE: 143
aggtattcaa agaacatat                                                   19

<210> SEQ ID NO 144
<211> LENGTH: 19
<212> TYPE: DNA
<213> ORGANISM: Homo sapiens

<400> SEQUENCE: 144
tgtctgttta aaagattgt                                                   19
```

```
<210> SEQ ID NO 145
<211> LENGTH: 19
<212> TYPE: DNA
<213> ORGANISM: Homo sapiens

<400> SEQUENCE: 145
tgtctgttta aaagattgc                                                19

<210> SEQ ID NO 146
<211> LENGTH: 18
<212> TYPE: DNA
<213> ORGANISM: Homo sapiens

<400> SEQUENCE: 146
caataggaca tggaatac                                                 18

<210> SEQ ID NO 147
<211> LENGTH: 19
<212> TYPE: DNA
<213> ORGANISM: Homo sapiens

<400> SEQUENCE: 147
caataggaca tggaatact                                                19

<210> SEQ ID NO 148
<211> LENGTH: 16
<212> TYPE: DNA
<213> ORGANISM: Homo sapiens

<400> SEQUENCE: 148
acttattttt acatac                                                   16

<210> SEQ ID NO 149
<211> LENGTH: 16
<212> TYPE: DNA
<213> ORGANISM: Homo sapiens

<400> SEQUENCE: 149
acttattttt acatat                                                   16

<210> SEQ ID NO 150
<211> LENGTH: 21
<212> TYPE: DNA
<213> ORGANISM: Homo sapiens

<400> SEQUENCE: 150
acttaccaag ctatccacat c                                             21

<210> SEQ ID NO 151
<211> LENGTH: 21
<212> TYPE: DNA
<213> ORGANISM: Homo sapiens

<400> SEQUENCE: 151
acttaccaag ctatccacat g                                             21

<210> SEQ ID NO 152
<211> LENGTH: 21
<212> TYPE: DNA
<213> ORGANISM: Homo sapiens

<400> SEQUENCE: 152
cctttcaggg tgtcttactc g                                             21
```

```
<210> SEQ ID NO 153
<211> LENGTH: 21
<212> TYPE: DNA
<213> ORGANISM: Homo sapiens

<400> SEQUENCE: 153
cctttcaggg tgtcttactc a                                              21

<210> SEQ ID NO 154
<211> LENGTH: 18
<212> TYPE: DNA
<213> ORGANISM: Homo sapiens

<400> SEQUENCE: 154
aatgaactta aagactcg                                                  18

<210> SEQ ID NO 155
<211> LENGTH: 18
<212> TYPE: DNA
<213> ORGANISM: Homo sapiens

<400> SEQUENCE: 155
aatgaactta aagactca                                                  18

<210> SEQ ID NO 156
<211> LENGTH: 20
<212> TYPE: DNA
<213> ORGANISM: Homo sapiens

<400> SEQUENCE: 156
gtatggtttg gttgacttgg                                                20

<210> SEQ ID NO 157
<211> LENGTH: 21
<212> TYPE: DNA
<213> ORGANISM: Homo sapiens

<400> SEQUENCE: 157
gtatggtttg gttgacttgt a                                              21

<210> SEQ ID NO 158
<211> LENGTH: 22
<212> TYPE: DNA
<213> ORGANISM: Homo sapiens

<400> SEQUENCE: 158
gtatggtttg gttgacttgg ta                                             22

<210> SEQ ID NO 159
<211> LENGTH: 21
<212> TYPE: DNA
<213> ORGANISM: Homo sapiens

<400> SEQUENCE: 159
gtatggtttg gttgacttgt a                                              21

<210> SEQ ID NO 160
<211> LENGTH: 18
<212> TYPE: DNA
<213> ORGANISM: Homo sapiens

<400> SEQUENCE: 160
actccaaagg ctttcctc                                                  18
```

<210> SEQ ID NO 161
<211> LENGTH: 17
<212> TYPE: DNA
<213> ORGANISM: Homo sapiens

<400> SEQUENCE: 161
ctccaaaggc tttcctt                                                    17

<210> SEQ ID NO 162
<211> LENGTH: 18
<212> TYPE: DNA
<213> ORGANISM: Homo sapiens

<400> SEQUENCE: 162
tgttcatagg gatccaag                                                   18

<210> SEQ ID NO 163
<211> LENGTH: 18
<212> TYPE: DNA
<213> ORGANISM: Homo sapiens

<400> SEQUENCE: 163
tgttcatagg gatccaac                                                   18

<210> SEQ ID NO 164
<211> LENGTH: 16
<212> TYPE: DNA
<213> ORGANISM: Homo sapiens

<400> SEQUENCE: 164
aggactccat gcccag                                                     16

<210> SEQ ID NO 165
<211> LENGTH: 831
<212> TYPE: DNA
<213> ORGANISM: Homo sapiens

<400> SEQUENCE: 165
cactgtagct gtactacctt ccatctcctc aacctattcc aactatctga atcatgtgcc      60
cttctctgtg aacctctatc ataatacttg tcacactgta ttgtaattgt ctcttttact     120
ttcccttgta tcttttgtgc atagcagagt acctgaaaca ggaagtattt taaatatttt     180
gaatcaaatg agttaataga atctttacaa ataagaatat acacttctgc ttaggatgat     240
aattggaggc aagtgaatcc tgagcgtgat ttgataatga cctaataatg atgggtttta     300
tttccagact tcacttctaa tgatgattat gggagaactg gagccttcag agggtaaaat     360
taagcacagt ggaagaattt cattctgttc tcagttttcc tggattatgc ctggcaccat     420
taaagaaaat atcatctttg gtgtttccta tgatgaatat agatacagaa gcgtcatcaa     480
agcatgccaa ctagaagagg taagaaacta tgtgaaaact ttttgattat gcatatgaac     540
ccttcacact acccaaatta tatatttggc tccatattca atcggttagt ctacatatat     600
ttatgtttcc tctatgggta agctactgtg aatggatcaa ttaataaaac acatgaccta     660
tgctttaaga agcttgcaaa cacatgaaat aaatgcaatt tatttttttaa ataatgggtt     720 catttgatca caataaatgc attttatgaa atggtgagaa ttttgttcac tcattagtga     780
gacaaacgtc tcaatggtta tttatatggc atgcatatag tgatatgtgg t              831

<210> SEQ ID NO 166

```
<211> LENGTH: 19
<212> TYPE: DNA
<213> ORGANISM: Homo sapiens

<400> SEQUENCE: 166
gcatggcggt cactcggca                                                 19

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (19)
<223> OTHER INFORMATION: a, c, g, t, unknown or other

<400> SEQUENCE: 167
tycryagtga ccyccytgn                                                 19

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
cgggagtgac cgccatgc                                                  18

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 169
cgtaccgcca gtgagngn                                                  18

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 170
cgtaccgcca gtgacngn                                                  18
```

```
<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 171
cgtaccccca gtgagngn                                                 18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 172
cgtaccccca gtgacngn                                                 18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 173
cgttccgcca gtgagngn                                                 18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
```

<223> OTHER INFORMATION: inosine

<400> SEQUENCE: 174
cgttccgcca gtgacngn                                               18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 175 cgttcccca gtgagngn                                                18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 176 cgttcccca gtgacngn                                                18

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 177
ggtaccgcca gtgagngn                                               18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base

```
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 178
ggtaccgcca gtgacngn                                            18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 179
ggtaccccca gtgagngn                                            18

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 180
ggtaccccca gtgacngn                                            18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 181
ggttccgcca gtgagngn                                            18

<210> SEQ ID NO 182
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 182
ggttccgcca gtgacngn                                                  18

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 183
ggttccccca gtgagngn                                                  18

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 184
ggttccccca gtgacngn                                                  18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 185
agtaccgcca gtgagngn                                                  18
```

```
<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 186
agtaccgcca gtgacngn                                                 18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 187
agtaccccca gtgagngn                                                 18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 188
agtaccccca gtgacngn                                                 18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine
```

```
<400> SEQUENCE: 189
agttccgcca gtgagngn                                              18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 190
agttccgcca gtgacngn                                              18

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 191
agttccccca gtgagngn                                              18

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 192
agttccccca gtgacngn                                              18

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
```

```
<223> OTHER INFORMATION: inosine
<220> FEATURE:
<221> NAME/KEY: modified_base
<222> LOCATION: (18)
<223> OTHER INFORMATION: inosine

<400> SEQUENCE: 193
tgtaccgcca gtgagngn                                                18

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 194
tgtaccgcca gtgacngn                                                18

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 195
tgtaccccca gtgagngn                                                18

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 196
tgtaccccca gtgacngn                                                18

<210> SEQ ID NO 197
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 197
tgttccgcca gtgagngn                                                   18

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 198
tgttccgcca gtgacngn                                                   18

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 199
tgttccccca gtgagngn                                                   18

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (16)
<223> OTHER INFORMATION: inosine
<220> FEATURE:
<221> NAME/KEY: modified_base
<222> LOCATION: (18)
<223> OTHER INFORMATION: inosine

<400> SEQUENCE: 200
tgttccccca gtgacngn                                                   18
```

```
<210> SEQ ID NO 201
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ggaacactct atcgcgattt atctaggcat aggctt                                36

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tgagatagcg ctaaataga                                                   19

<210> SEQ ID NO 203
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggaaccctct atcgcgattt atctaggcat aggctt                                36

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ggagatagcg ctaaataga                                                   19

<210> SEQ ID NO 205
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ggaacgctct atcgcgattt atctaggcat aggctt                                36

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cgagatagcg ctaaataga                                                   19

<210> SEQ ID NO 207
```

-continued

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ggaactctct atcgcgattt atctaggcat aggctt                              36

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
agagatagcg ctaaataga                                                 19
```

MULTIPLEXED ANALYSIS OF POLYMORPHIC LOCI BY CONCURRENT INTERROGATION AND ENZYME-MEDIATED DETECTION

CROSS-REFERENCE TO RELATED APPLICATIONS

This application is a divisional of U.S. application Ser. No. 11/438,741, filed May 22, 2006, which claims priority to U.S. application Ser. No. 10/271,602, filed Oct. 15, 2002, now abandoned, which claims the benefit under 35 U.S.C. 119(e) to U.S. Provisional Application No. 60/364,416, filed Mar. 14, 2002; U.S. Provisional Application No. 60/329,620, filed Oct. 15, 2001; U.S. Provisional No. 60/329,428, filed Oct. 15, 2001; U.S. Provisional Application No. 60/329,427, filed Oct. 15, 2001; and U.S. Provisional Application No. 60/329,619, filed Oct. 15, 2001, the entire disclosures of which are incorporated herein by reference for all purposes.

FIELD OF THE INVENTION

The present invention generally relates to molecular diagnostics and genetic typing or profiling. The invention relates to methods, processes and probes for the multiplexed analysis of highly polymorphic genes. The invention also relates to the molecular typing and profiling of the Human Leukocyte Antigen (HLA) gene complex and the Cystic Fibrosis Conductance Transmembrane Regulator gene (CFTR) and to compositions, methods and designs relating thereto.

BACKGROUND OF THE INVENTION

The ability to efficiently, rapidly and unambiguously analyze polymorphisms in the nucleic acid sequences of a gene of interest plays an important role in the development of molecular diagnostic assays, the applications of which includes genetic testing, carrier screening, genotyping or genetic profiling, and identity testing. For example, it is the objective of genetic testing and carrier screening to determine whether mutations associated with a particular disease are present in a gene of interest. The analysis of polymorphic loci, whether or not these comprise mutations known to cause disease, generally provides clinical benefit, as for example in the context of pharmacogenomic genotyping or in the context of HLA molecular typing, in which the degree of allele matching in the HLA loci of transplant donor and prospective recipient is determined in context of allogeneic tissue and bone marrow transplantation.

The multiplexed analysis of polymorphisms while desirable in facilitating the analysis of a high volume of patient samples, faces a considerable level of complexity which will likely increase as new polymorphisms, genetic markers and mutations are identified and must be included in the analysis. The limitations of current methods to handle this complexity in a multiplexed format of analysis so as to ensure reliable assay performance while accommodating high sample volume, and the consequent need for novel methods of multiplexed analysis of polymorphisms and mutations is the subject of the present invention. By way of example, the genetic loci encoding the Cystic Fibrosis Transmembrane Conductance (CFTR) channel and Human Leukocyte Antigens (HLA) are analyzed by the methods of the invention. Cystic fibrosis (CF) is one of the most common recessive disorders in Caucasians with a rate of occurrence in the US of 1 in 2000 live births. About 4% of the population carry one of the CF mutations. The CFTR gene is highly variable: more than 900 mutations have been identified to date (see the website at found at server name genet.sickkids.on with domain name ca, at resource ID cftr, which is incorporated herein by reference). The characterization of the CFTR gene provides the key to the molecular diagnosis of CF by facilitating the development of sequence-specific probes (Roments et al., 1989; Riordan, et al., 1989; Kerem et al., 1989, each of which is incorporated herein by reference). The National Institutes of Health (NIH)—sponsored consensus development conference recommended carrier screening for CFTR mutations for adults with a positive family history of CF (NIH 1997). The committee on carrier screening of the American College of Medical Genetics (ACMG) has recommended for use in general population carrier screening a pan-ethnic mutation panel that includes a set of 25 disease-causing CF mutations with an allele frequency of >0.1% in the general population of United States (see the Federation of American Societies of Experimental Biology website (domain name .org) at resource ID genetics/acmg, which is incorporated herein by reference). The mutations in the ACMG panel also include the most common mutations in Ashkenazi Jewish and African-American populations.

Several methods have been described for the detection of CFTR mutations including the following: denaturing gradient gel electrophoresis (Devoto et al., 1991); single strand conformation polymorphism analysis (Plieth et al., 1992); RFLP (Friedman et al., 1991); amplification with allele-specific primers (ASPs) (Gremonesi et al., 1992), and probing with allele specific oligonucleotides (ASO) (Saiki et al., 1986). A widely used method involves PCR amplification followed by blotting of amplified target strands onto a membrane and probing of strands with oligonucleotides designed to match either the normal ("wild type") or mutant configuration. Specifically, multiplex PCR has been used in conjunction with ASO hybridization in this dot blot format to screen 12 CF mutations (Shuber et al., 1993). In several instances, arrays of substrate-immobilized oligonucleotide probes were used to facilitate the detection of known genomic DNA sequence variations (Saiki, R K et al., 1989) in a "reverse dot blot" format An array of short oligonucleotides synthesized in-situ by photolithographic processes was used to detect known mutations in the coding region of the CFTR gene (Cronin, M T., et al., 1996). Primer extension using reverse transcriptase has been reported as a method for detecting the A508 mutation in CFTR (Pastinen, T., 2000). This approach was described as early as 1989 (Wu, D. Y. et al, Proc. Natl. Acad. Sci. USA. 86:2757-2760 (1989), Newton, C. R. et al, Nucleic Acids Res. 17:2503-2506 (1989)). As further discussed herein below, while providing reasonable detection in a research laboratory setting, these methods require significant labor, provide only slow turnaround, offer only low sample throughput, and hence require a high cost per sample.

In connection with the spotted microarrays, several methods of spotting have been described, along with many substrate materials and methods of probe immobilization. However, the spotted arrays of current methods exhibit not only significant array-to-array variability but also significant spot-to-spot variability, an aspect that leads to limitations in assay reliability and sensitivity. In addition, spotted arrays are difficult to miniaturize beyond their current spot dimensions of typically 100 μm diameter on 500 μm centers, thereby increasing total sample volumes and contributing to slow assay kinetics limiting the performance of hybridization assays whose completion on spotted arrays may require as much as 18 hours. Further, use of spotted arrays involve readout via highly specialized confocal laser scanning apparatus. In an alternative approach, oligonucleotide arrays synthesized in-situ by a photolithographic process have been described. The complexity of array fabrication, however, limits routine customization and combines considerable expense with lack of flexibility for diagnostic applications.

The major histocompatibility complex (MHC) includes the human leukocyte antigen (HLA) gene complex, located on the short arm of human chromosome six. This region encodes cell-surface proteins which regulate the cell-cell interactions underlying immune response. The various HLA Class I loci encode 44,000 dalton polypeptides which associate with 13-2 microglobulin at the cell surface and mediate the recognition of target cells by cytotoxic T lymphocytes. HLA Class II loci encode cell surface heterodimers, composed of a 29,000 dalton and a 34,000 dalton polypeptide which mediate the recognition of target cells by helper T lymphocytes. HLA antigens, by presenting foreign pathogenic peptides to T-cells in the context of a "self" protein, mediate the initiation of an immune response. Consequently, a large repertoire of peptides is desirable because it increases the immune response potential of the host. On the other hand, the correspondingly high degree of immunogenetic polymorphism represents significant difficulties in allotransplantation, with a mismatch in HLA loci representing one of the main causes of allograft rejection. The degree of allele matching in the HLA loci of a donor and prospective recipient is a major factor in the success of allogeneic tissue and bone marrow transplantation.

The HLA-A, HLA-B, and HLA-C loci of the HLA Class I region as well as the HLA-DRB, HLA-DQB, HLA-DQA, HLA-DPB and HLA-DPA loci of the HLA Class II region exhibit an extremely high degree of polymorphism. To date, the WHO nomenclature committee for factors of the HLA system has designated 225 alleles of HLA A (HLA A*0101, A*0201, etc.), 444 alleles of HLA-B, and 111 alleles of HLA-C, 358 HLA-DRB alleles, 22 HLA-DQA alleles, 47 HLA-DQB alleles, 20 HLA-DPA alleles and 96 HLA-DPB alleles (See IMGT/HLA Sequence Database, found at server name ebi.ac with domain name uk80, at resource ID imgt/h1a/index.html and Schreuder, G. M. Th. et al, Tissue Antigens. 54:409-437 (1999)), both of which are hereby incorporated by reference.

HLA typing is a routine procedure that is used to determine the immunogenetic profile of transplant donors. The objective of HLA typing is the determination of the patient's allele configuration at the requisite level of resolution, based on the analysis of a set of designated polymorphisms within the genetic locus of interest. Increasingly, molecular typing of HLA is the method of choice over traditional serological typing, because it eliminates the requirement for viable cells, offers higher allelic resolution, and extends HLA typing to Class II for which serology has not been adequate (Erlich, H. A. et al, Immunity 14:347-356 (2001)).

One method currently applied to clinical HLA typing uses the polymerase chain reaction (PCR) in conjunction with sequence-specific oligonucleotide probes (SSO or SSOP), which are allowed to hybridize to amplified target sequences to produce a pattern as a basis for HLA typing.

The availability of sequence information for all available HLA alleles has permitted the design of sequence-specific oligonucleotides (SSO) and allele-specific oligonucleotides (ASO) for the characterization of known HLA polymorphisms as well as for sequencing by hybridization (Saiki, R. K. Nature 324:163-166 (1986), Cao, K. et al, Rev Immunogenetics, 1999: 1: 177-208).

In one embodiment of SSO analysis, also referred to as a "dot blot format", DNA samples are extracted from patients, amplified and blotted onto a set of nylon membranes in an 8×12 grid format. One radio-labeled oligonucleotide probe is added to each spot on each such membrane; following hybridization, spots are inspected by autoradiography and scored either positive (1) or negative (0). For each patient sample, the string of 1's and 0's constructed from the analysis of all membranes defines the allele configuration. A multiplexed format of SSO analysis in the "reverse dot blot format" employs sets of oligonucleotide probes immobilized on planar supports (Saiki, R. et al, Immunological Rev. 167: 193-199 (1989), Erlich, H. A. Eur. J. Immunogenet. 18: 33-55 (1991)).

Another method of HLA typing uses the polymerase-catalyzed elongation of sequence-specific primers (SSPs) to discriminate between alleles. The high specificity of DNA polymerase generally endows this method with superior specificity. In the SSP method, PCR amplification is performed with a specific primer pair for each polymorphic sequence motif or pair of motifs and a DNA polymerase lacking 3'→5' exonuclease activity so that elongation (and hence amplification) occurs only for that primer whose 3' terminus is perfectly complementary ("matched") to the template. The presence of the corresponding PCR product is ascertained by gel electrophoretic analysis. An example of a highly polymorphic locus is the 280 nt DNA fragment of the HLA class II DR gene which features a high incidence of polymorphisms HLA typing based on the use of sequence-specific probes (SSP), also referred to as phototyping (Dupont, B. Tissue Antigen. 46: 353-354 (1995)), has been developed as a commercial technology that is in routine use for class I and class II typing (Bunce, M. et al, Tissue Antigens. 46:355-367 (1995), Krausa, P and Browning, M. J., Tissue Antigens. 47: 237-244 (1996), Bunce, M. et al, Tissue Antigens. 45:81-90 (1995)). However, the requirement of the SSP methods of the prior art for extensive gel electrophoretic analysis for individual detection of amplicons represents a significant impediment to the implementation of multiplexed assay formats that can achieve high throughput. This disadvantage is overcome by the methods of the present invention.

In the context of elongation reactions, highly polymorphic loci and the effect of non-designated polymorphic sites as interfering polymorphisms were not considered in previous applications, especially in multiplexed format. Thus, there is a need to provide for methods, compositions and processes for the multiplexed analysis of polymorphic loci that would enable the detection of designated while accommodating the presence of no-designated sites and without interference from such non-designated sites.

SUMMARY OF THE INVENTION

The present invention provides methods and processes for the concurrent interrogation of multiple designated polymorphic sites in the presence of non-designated polymorphic sites and without interference from such non-designated sites. Sets of probes are provided which facilitate such concurrent interrogation. The present invention also provides methods, processes, and probes for the identification of polymorphisms of the HLA gene complex and the CFTR gene.

The specificity of methods of detection using probe extension or elongation is intrinsically superior to that of methods using hybridization, particularly in a multiplexed format, because the discrimination of sequence configurations no longer depends on differential hybridization but on the fidelity of enzymatic recognition. To date, the overwhelming majority of applications of enzyme-mediated analysis use single base probe extension. However, probe elongation, in analogy to that used in the SSP method of HLA typing, offers several advantages for the multiplexed analysis of polymorphisms, as disclosed herein. Thus, single nucleotide as well as multi-nucleotide polymorphisms are readily accommodated. The method, as described herein, is generally practiced with only single label detection, accommodates concurrent as well as consecutive interrogation of polymorphic loci and incorporates complexity in the probe design.

One aspect of this invention provides a method of concurrent determination of nucleotide composition at designated polymorphic sites located within one or more target nucleotide sequences. This method comprises the following steps: (a) providing one or more sets of probes, each probe capable of annealing to a subsequence of the one or more target nucleotide sequences located within a range of proximity to a designated polymorphic site; (b) contacting the set of probes with the one or more target nucleotide sequences so as to permit formation of hybridization complexes by placing an interrogation site within a probe sequence in direct alignment with the designated polymorphic site; (c) for each hybridization complex, determining the presence of a match or a mismatch between the interrogation site and a designated polymorphic site; and (d) determining the composition of the designated polymorphic site.

Another aspect of this invention is to provide a method of sequence-specific amplification of assay signals produced in the analysis of a nucleic acid sequence of interest in a biological sample. This method comprises the following steps: (a) providing a set of immobilized probes capable of forming a hybridization complex with the sequence of interest; (b) contacting said set of immobilized probes with the biological sample containing the sequence of interest under conditions which permit the sequence of interest to anneal to at least one of the immobilized probes to form a hybridization complex; (c) contacting the hybridization complex with a polymerase to allow elongation or extension of the probes contained within the hybridization complex; (d) converting elongation or extension of the probes into an optical signal; and (e) recording the optical signal from the set of immobilized probes in real time.

Yet another aspect of this invention is to provide a method of forming a covering probe set for the concurrent interrogation of a designated polymorphic site located in one or more target nucleic acid sequences. This method comprises the steps of: (a) determining the sequence of an elongation probe capable of alignment of the interrogation site of the probe with a designated polymorphic site; (b) further determining a complete set of degenerate probes to accommodate all non-designated as well as non-selected designated polymorphic sites while maintaining alignment of the interrogation site of the probe with the designated polymorphic site; and (c) reducing the degree of degeneracy by removing all tolerated polymorphisms.

One aspect of this invention is to provide a method for identifying polymorphisms at one or more designated sites within a target polynucleotide sequence. This the method comprise the following steps: (a) providing one or more probes capable of interrogating said designated sites; (b) assigning a value to each such designated site while accommodating non-designated polymorphic sites located within a range of proximity to each such polymorphism.

Another aspect of this invention is to provide a method for determining a polymorphism at one or more designated sites in a target polynucleotide sequence. This method comprises providing a probe set for the designated sites and grouping the probe set in different probe subsets according to the terminal elongation initiation of each probe.

Another aspect of this invention is to provide a method for the concurrent interrogation of a multiplicity of polymorphic sites comprising the step of conducting a multiplexed elongation assay by applying one or more temperature cycles to achieve linear amplification of such target.

Yet another aspect of this invention is to provide a method for the concurrent interrogation of a multiplicity of polymorphic sites. This method comprises the step of conducting a multiplexed elongation assay by applying a combination of annealing and elongation steps under temperature-controlled conditions.

Another aspect of this invention is to provide a method of concurrent interrogation of nucleotide composition at S polymorphic sites, $P_s:=\{c_p(s); 1 \leq s \leq S\}$ located within one or more contiguous target sequences, said method assigning to each c. one of a limited set of possible values by performing the following steps: (a) providing a set of designated immobilized oligonucleotide probes, also known as elongation probes, each probe capable of annealing in a preferred alignment to a subsequence of the target located proximal to a designated polymorphic site, the preferred alignment placing an interrogation site within the probe sequence in direct juxtaposition to the designated polymorphic site, the probes further containing a terminal elongation initiation (TEI) region capable of initiating an elongation or extension reaction; (b) permitting the one or more target sequences to anneal to the set of immobilized oligonucleotide probes so as form probe-target hybridization complexes; and (c) for each probe-target hybridization complex, calling a match or a mismatch in composition between interrogation site and corresponding designated polymorphic site.

Other objects, features and advantages of the invention will be more clearly understood when taken together with the following detailed description of an embodiment which will be understood as being illustrative only.

BRIEF DESCRIPTION OF THE D WINGS

FIG. 4 shows simulated ambiguity in allele identification due to allele combination.

FIG. 16 is an illustration of results for probe elongation of a multiplexed CF mutation.

DETAILED DESCRIPTION OF THE INVENTION

Figure 1A:
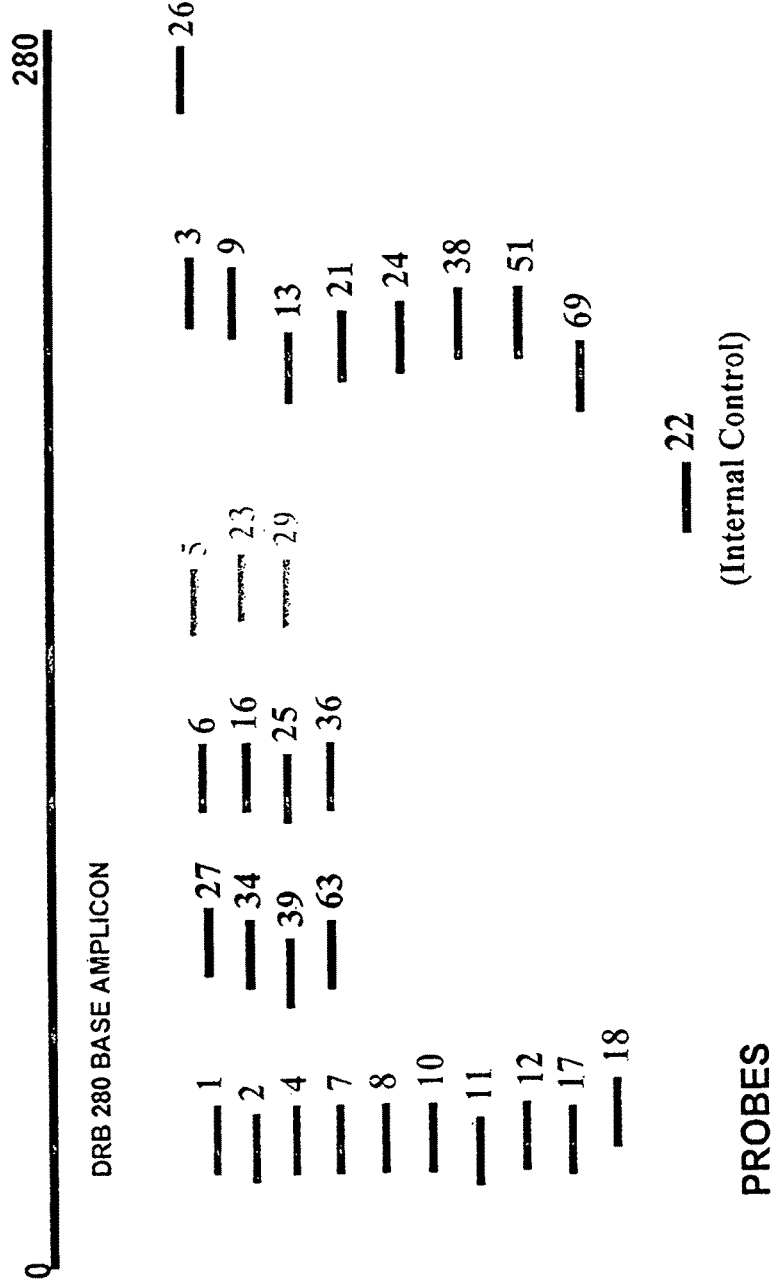
FIG. 1a is an illustration of probe sets designed to interrogate designated sites in HLA-DR and an internal control.

This invention provides compositions, methods and designs for the multiplexed analysis of highly polymorphic loci; that is, loci featuring a high density of specific ("designated") polymorphic sites, as well as interfering non-designated polymorphic sites. The multiplexed analysis of such sites thus generally involves significant overlap in the sequences of probes directed to adjacent sites on the same target, such that probes designed for any specific or designated site generally also will cover neighboring polymorphic sites. The interference in the analysis of important genes including CFTR and HLA has not been addressed in the prior art. To exemplify the methods of the methods of the invention, the HLA gene complex and the CFTR gene are analyzed.

The present invention provides compositions and methods for the parallel or multiplexed analysis of polymorphisms ("MAP") in nucleic acid sequences displaying a high density of polymorphic sites. In a given nucleic acid sequence, each polymorphic site comprises a difference comprising one or more nucleotides.\

This invention provides methods and compositions for the concurrent interrogation of an entire set of designated polymorphisms within a nucleic acid sequence. This invention provides compositions, methods and designs to determine the composition at each such site and thereby provide the requisite information to select, from the set of possible configurations for the sequence of interest, the actual configuration in a given specific sample. The invention also serves to narrow the set of possible sequences in that sample. Accordingly, in certain embodiments, it will be useful or necessary to determine sequence composition by assigning to a designated site one of the possible values corresponding to nucleotide identity. In other embodiments, it will be sufficient to determine the site composition to be either matching or non-matching with respect to a known reference sequence, as in the assignment of "wild-type" or "mutation" in the context mutation analysis. The capability of sequence determination thereby afforded is referred to herein as confirmatory sequencing or resequencing. In a preferred embodiment, the present invention provides elongation-mediated multiplexed analysis of polymorphisms (eMAP) of the Cystic Fibrosis Transmembrane Conductance Regulator (CFTR) gene and for the Human Leukocyte Antigen (HLA) gene complex.

The methods and compositions of this invention are useful for improving the reliability and accuracy of polymorphism analysis of target regions which contain polymorphic sites in addition to the polymorphic sites designated for interrogation. These non-designated sites represent a source of interference in the analysis. Depending on the specific assay applications, one or more probes of differing composition may be designated for the same polymorphic site, as elaborated in several Examples provided herein. It is a specific objective of the present invention to provide compositions and methods for efficient, rapid and unambiguous analysis of polymorphisms in genes of interest. This analysis is useful in molecular diagnostic assays, such as those designed, for example, for genetic testing, carrier screening, genotyping or genetic profiling, identity testing, paternity testing and forensics.

Preparation of target sequences may be carried out using methods known in the art. In a non-limiting example, a sample of cells or tissue is obtained from a patient. The nucleic acid regions containing target sequences (e.g., Exons 2 and 3 of 1-ILA) are then amplified using standard techniques such as PCR (e.g., asymmetric PCR).

Probes for detecting polymorphic sites function as the point of initiation of a polymerase-catalyzed elongation reaction when the composition of a polymorphic site being analyzed is complementary ("matched") to that of the aligned site in the probe. Generally, the probes of the invention should be sufficiently long to avoid annealing to unrelated DNA target sequences. In certain embodiments, the length of the probe may be about 10 to 50 bases, more preferably about 15 to 25, and more preferably 18 to 20 bases. Probes may be immobilized on the solid supports via linker moieties using methods and compositions well known in the art.

As used herein, the term "nucleic acid" or "oligonucleotide" refers to deoxyribonucleic acid or ribonucleic acid in a single or double-stranded form. The term also covers nucleic-acid like structures with synthetic backbones. DNA backbone analogues include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs). See Oligonucleotides and Analogues, A Practical Approach (Editor: F. Eckstein), IRL Press at Oxford University Press (1991); Antisense Strategies, Annals of the New York Academy of Sciences, vol. 600, Eds.; Baserga and Denhardt (NYAS 1992); Milligan, J. Med. Chem., vol. 36, pp. 1923-1937;

Antisense Research and Applications (1993, CRC Press). PNAs contain non-ionic backbones, such as N-2(2-aminoethyl) glycine units. Phosphorothioate linkages are described in WO 97/03211; WO 96/39159; and Mata, Toxicol. Appl. Phaimacol. 144: 189-197 (1997). Other synthetic backbones encompassed by the term include methyl-phosphonate linkages or alternating methylphosphonate and phosphodiester linkages (Strauss-Soukup, Biochemistry, 36: 8692-8698 (1997), and benzylphosphonate linkages (Samstag, Antisense Nucleic Acid Drug Dev., 6: 153-156 (1996)). The term nucleic acid includes genes, cDNAs, and mRNAs.

As used herein, the term "hybridization" refers to the binding, duplexing, or hybridizing of a nucleic acid molecule preferentially to a particular nucleotide sequence under stringent conditions. The term "stringent conditions" refers to conditions under which a probe will hybridize preferentially to the corresponding target sequence, and to a lesser extent or not at all to other sequences. A "stringent hybridization" is sequence dependent, and is different under different conditions. An extensive guide to the hybridization of nucleic acids may be found in, e.g. Tijssen, Laboratory Techniques in Biochemistry and Molecular Biology, Elsevier, N.Y. (1993). Generally, highly stringent hybridization and wash conditions are selected to about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected by conducting the assay at a temperature set to be equal to the $T_m$ for a particular probe. An example of highly stringent wash condition is 0.15 M NaCl at 72° C. for about 15 minutes. An example of stringent wash conditions is a 0.2×SSC wash at 65° C. for 15 minutes. See Sambrook, Molecular Cloning: A Laboratory Manual (2nd Ed), vol. 1-3 (1989).

As used herein, the term "designated site" is defined as a polymorphic site of interest (i.e., a polymorphic site that one intends to identify) on a given nucleic acid. The term "non-designated site" refers to any polymorphic site that co-exists with a designated site or sites on a given nucleic acid but is not of interest.

As used herein, the term "correlated designated sites" refers to polymorphic sites with correlated occurrences. Typically, each member of such a set of polymorphic sites must be identified in order to identify the allele to which the set belongs.

As used herein, the term "selected designated site" refers to a polymorphic site of interest on a given nucleic acid that also overlaps with the 3 'end of a probe sequence of this invention. A "non-selected designated site" refers to a polymorphic site of interest that does not overlap with a 3' end of a probe sequence of this invention.

As used herein, an "interfering non-designated site" refers to a non-designated polymorphic site that is within 1-5 bases from the 3' end of a probe sequence of this invention. A "non-interfering non-designated site" refers to a non-designated site that is greater than 5 bases from the 3' end of a probe sequence of this invention. The non-interfering non-designated site may be closer to the 5' end of the probe sequence than to the 3' end.

In certain embodiments, the probes of this invention comprise a "terminal elongation initiation" region (also referred to as a "TEI" region) and a Duplex Anchoring ("DA") region. The TEI region refers a section of the probe sequence, typically the three or four 3' terminal positions of the probe. The TEI region is designed to align with a portion of the target nucleic acid sequence at a designated polymorphic site so as to initiate the polymerase-catalyzed elongation of the probe. The DA region, typically comprises the remaining positions within the probe sequence and is preferably designed to align with a portion of the target sequence in a region located close (within 3-5 bases) to the designated polymorphism.

As used herein, the term a "close range of proximity" refers to a distance of between 1-5 bases along a given nucleic acid strand. A "range of proximity" refers to a distance within 1-10 bases along a given nucleic acid strand. The term "range of tolerance" refers to the total number of mismatches in the TEI region of a probe hybridized to a target sequence that still permits annealing and elongation of the probe. Typically, more than 2 mismatches in the TEI region of a hybridized probe is beyond the range of tolerance.

The terms "microspheres", "microparticles", "beads", and "particles" are herein used interchangeably. The composition of the beads includes, but is not limited to, plastics, ceramics, glass, polystyrene, methylstyrene, acrylic polymers, paramagnetic materials, thoria sol, carbon graphite, titanium dioxide, latex or cross-linked dextrans such as sepharose, cellulose, nylon, cross-linked micelles and Teflon. See "Microsphere Detection Guide" from Bangs Laboratories, Fishers Ind. The particles need not be spherical and may be porous. The bead sizes may range from nanometers (e.g., 100 nm) to millimeters (e.g., 1 mm), with beads from about 0.2 micron to about 200 microns being preferred, more preferably from about 0.5 to about 5 micron being particularly preferred.

This invention provides for the concurrent interrogation of a set of designated polymorphic sites within one or more target strands by first annealing a set of immobilized sequence specific oligonucleotide probes to target nucleic acid strands and by probing the configuration of designated polymorphic sites by way of polymerase-catalyzed elongation of the annealed set of immobilized sequence-specific oligonucleotide probes. An elongation probe is designed to interrogate a designated site by annealing to a sequence in a given target, thereby forming a hybridization complex ("duplex"). The probe's 3' terminus is placed at or near the designated site within the target and polymerase-catalyzed probe elongation is initiated if the 3' terminal probe composition matches (i.e., is complementary to) that of the target at the interrogation site. As described herein, the probe may be designed to anneal in a manner such that the designated site is within a range of proximity of the 3' terminus.

In one embodiment of the invention, two or more probes may be provided for interrogation of a specific designated site. The probes are designed to take into account the possibility of polymorphisms or mutations at the interrogation site and non-designated polymorphic sites within a certain range of proximity of the designated polymorphic site. In this context, the term "polymorphism" refers to any variation in a nucleic acid sequence, while the term "mutation" refers to a sequence variation in a gene that is associated or believed to be associated with a phenotype. In a preferred embodiment, this multiplicity of probe sequences contains at least one probe that matches the specific target sequence in all positions within the range of proximity to ensure elongation.

In certain embodiments, the invention discloses compositions and methods for the parallel interrogation of S polymorphic sites selected from a target sequence of length N by a set of L≥S oligonucleotide primers.

In accordance with the requirements of specific assay applications, one or more probes of differing composition may be designated for the same polymorphic site, as elaborated in several Examples provided herein.

Each designated probe is composed of a nucleotide sequence of length M which contains an interrogation site (one that, upon hybridization, aligns with the polymorphic site being analyzed) at or near the 3' terminus. Although 3' end is preferred, those within 3-4 bases from the 3' end may be used. The primer is immobilized on a solid phase carrier (may be linked via a linker sequence or other linker moiety) and is identified by its association with that carrier. The probe sequence is designed to permit annealing of the primer with the target so as to form a hybridization complex between probe and target and to ensure the alignment of the interrogation site with the designated polymorphic site, the preferred configuration providing an interrogation site at the probe's 3' terminus and alignment of the 3' terminus with the designated polymorphic site. The step of interrogating the nucleotide composition of the designated polymorphic site with a designated probe of given interrogation site composition assigns to that site one of two values, namely matched, numerically represented by 1, or non-matched, numerically represented by 0. In HLA molecular typing, the resulting binary string of length L identifies an allele to a desired typing resolution.

In a preferred embodiment, the interrogation step uses the extension of the designated probe. This reaction, catalyzed by a polymerase, produces an extended hybridization complex by adding to the probe sequence one or more nucleoside triphosphates in the order reflecting the sequence of the target sequence in the existing hybridization complex. In order for this extension reaction to proceed, a designated primer of length M must contain a terminal extension initiation region of length $M^* \leq M$, herein also referred to as terminal extension initiation sequence (or TEI sequence), which contains the interrogation site. Extension proceeds if the composition of the designated interrogation site matches that of the designated polymorphic site.

Methods of the prior art of detecting successful extension have been described which involve the use labeled deoxy nucleoside triphosphates (dNTPs) or dideoxy nucleoside triphosphates (ddNTPs). The present invention also discloses novel methods of providing optical signatures for detection of successful extension eliminating the need for labeled dNTPs or ddNTPs, an advantage arising from the reduction in the efficiency of available polymerases in accommodating labeled dNTPs or ddNTPs.

However, the density of polymorphic sites in highly polymorphic loci considered in connection with the present invention makes it likely that designated primers directed to selected polymorphic sites, when annealing to the target subsequence proximal to the designated polymorphic site, will overlap adjacent polymorphic sites.

That is, an oligonucleotide probe, designed to interrogate the configuration of the target at one of the selected polymorphic sites, and constructed with sufficient length to ensure specificity and thermal stability in annealing to the correct target subsequence, will align with other nearby polymorphic sites. These interfering polymorphic sites may include the non-designated sites as well as non-selected designated sites in the target sequence.

In a multiplexed SSP reaction carried out in solution, the partial overlap between designated probes directed to nearby selected polymorphisms may lead to mutual competition between probes for the same target. The present invention significantly reduces this complication by way of probe immobilization.

As with multiplexed differential hybridization generally, the mismatch in one or more positions between a designated probe and target may affect the thermal stability of the hybridization complex. That is, any set of annealing conditions applied to the entire reaction mixture may produce varying degrees of annealing between probe and target and may affect the outcome of the subsequent probe extension reaction, thereby introducing ambiguities in the assay which may require subsequent resequencing.

Non-designated polymorphic sites located in immediate proximity to the interrogation site near or at the 3' terminus of the designated probe are particularly deleterious to the effectiveness of the probe's TEI sequence in initiating the extension reaction.

The power of currently available polymerase enzymes catalyzing the extension reaction to discriminate between a match and a mismatch in composition between the interrogation site within the designated primer and the polymorphic site depends on the displacement of the interrogation site from the primer's 3' terminus, considering single nucleotide as well as multiple nucleotide polymorphisms.

In a preferred embodiment yielding optimal discriminating power, the interrogation site is provided at the probe's 3' terminus. Given a probe sequence of length M designated for a selected site s* in the representation $P_{M(s^*)} := \{c_{p(m)}; 1 \leq m \leq M\}$, the index m increasing in the primer's 5' to 3' direction, this configuration provides for alignment of the designated site s* with position M in the probe sequence; in the case of multiple nucleotide polymorphisms, positions M−1 (for a dinucleotide polymorphism) and M−2 (for a trinucleotide polymorphism), etc. also are implicated.

Under these circumstances as they are anticipated in the multiplexed analysis of highly polymorphic loci, the advantage of enhanced specificity afforded by the application of a polymerase-catalyzed extension reaction is greatly diminished or lost as a result of complications arising from "sub-optimal" annealing conditions closely related to those limiting the performance of SSO analysis.

In connection with the optimization of the design of multiple probe sequences sharing the same interrogation site composition for any given designated polymorphic site, it will be useful to consider the concept of tolerance of interfering polymorphisms. Considering without limitation of generality the example of the single nucleotide polymorphism, a shift in alignment of s* away from the 3' terminus to positions M−1, M−2, . . . , M−m* leads to a gradually diminished discriminatory power. That is, when the designated polymorphic site is aligned with an interior probe position, m*, the extension reaction no longer discriminates between match and mismatch. Conversely, in the preferred embodiment of placing the interrogation site at the probe's 3' terminus, the deleterious effect of nearby non-designated polymorphisms on the effectiveness of the extension reaction likewise decreases with distance from the 3' terminus. That is, non-designated polymorphisms aligned with position between 1 and m* will not affect the extension reaction.

The terminal sequence of length M−m*+1 within the probe is herein referred to as the TEI sequence of a given primer. In general, 1<m*<M, and the TEI sequence may comprise only small number of terminal probe positions; in certain cases, m*=1, so that the probe sequence encompasses the entire probe sequence.

The present invention accommodates the presence of interfering polymorphic sites within the length of a designated probe sequence by taking into account these known sequence variations in the design of multiple probes. In particular, the number of alternate probe sequence configurations to be provided for given probe length M is significantly reduced as a result of the existence of a TEI sequence of length M−m*+1. That is, in order to ensure effective discriminatory power of the extension reaction, it is sufficient to restrict the anticipatory alternate probe sequence configurations to the length of the TEI sequence. In a preferred embodiment, all possible alternative sequences are anticipated so that one of these alternate probe sequences will match the target in all of the positions m*, m*+1, . . . M−1, M.

Providing, for each selected polymorphic site, a multiplicity of designated probes with anticipatory sequences increases the complexity of coding if all of these probes are separately encoded by the unique association with coded solid phase carriers. However, this complexity is reduced by placing this set of probes on a common solid phase carrier. That is, only the interrogation site composition of any designated probes is encoded, a concept herein referred to as TEI sequence pooling or probe pooling. Complete probe sequence pooling reduces the coding complexity to that of the original design in which no anticipatory probe sequences were provided. Partial pooling also is possible.

In certain preferred embodiments, the polymerase used in probe elongation is a DNA polymerase that lacks 3' to 5' exonuclease activity. Examples of such polymerases include T7 DNA polymerase, T4 DNA polymerase, ThermoSequenase and Taq polymerase. When the target nucleic acid sequence is RNA, reverse transcriptase may be used. In addition to polymerase, nucleoside triphosphates are added, preferably all four bases. For example dNTPs, or analogues, may be added. In certain other embodiments, ddNTPs may be added. Labeled nucleotide analogues, such as Cyc3-dUTP may also be used to facilitate detection.

Prior art methods for detecting successful elongation have been described which use labeled deoxy nucleoside triphosphates (dNTPs) or dideoxy nucleoside triphosphates (ddNTPs). This invention discloses novel methods of providing optical signatures for detecting successful elongation, thus eliminating the need for labeled dNTPs or ddNTPs. This is advantageous because currently available polymerases are less efficient in accommodating labeled dNTPs or ddNTPs.

This invention provides methods and compositions for accurate polymorphism analysis of highly polymorphic target regions. As used herein, highly polymorphic sequences are those containing, within a portion of the sequence contacted by the probe, not only the designated or interrogated polymorphic site, but also non-designated polymorphic sites which represent a potential source of error in the analysis. Analogous considerations pertain to designs, compositions and methods of multiplexing PCR reactions. In a preferred embodiment, covering sets of PCR probes composed of priming and annealing subsequences are displayed on encoded microparticles to produce bead-displayed amplicons by probe elongation. Assemblies of beads may be formed on planar substrates, prior to or subsequent to amplification to facilitate decoding and imaging of probes.

In one embodiment, this invention provides probes that are designed to contain a 3' terminal "priming" subsequence, also referred to herein as a Terminal Elongation Initiation (TE 1) region, and an annealing subsequence, also referred to herein as a Duplex Anchoring (DA) region. The TEI region typically comprises the three or four 3' terminal positions of a probe sequence. The TEI region is designed to align with a portion of the target sequence at a designated polymorphic site so as to initiate the polymerase-catalyzed elongation of the probe. Probe elongation indicates a perfect match in composition of the entire TEI region and the corresponding portion of the target sequence. The DA region, comprising remaining positions within the probe sequence, is preferably designed to align with a portion of the target sequence in a region located close (within 3-5 bases) to the designated polymorphism. The duplex anchoring region is designed to ensure specific and strong annealing, and is not designed for polymorphism analysis. As described herein, the DA and TEI regions may be located immediately adjacent to one another within the probe or may be linked by a molecular tether. The latter approach permits flexibility in the placement of DA region so as to avoid non-designated polymorphisms located immediately adjacent to the designated site. The composition and length of the DA region are chosen to facilitate the formation of a stable sequence-specific hybridization complex ("duplex"), while accommodating (i.e., taking into account) the presence of one or more non-designated polymorphisms located in that region of the target. The length of the annealing subsequence is chosen to minimize cross-hybridization by minimizing sequence homologies between probe and non-selected subsequences of the target. The length of the annealing subsequence generally exceeds that of the priming subsequence so that failure to form a duplex generally implies failure to produce an elongation product.

The elongation reaction provides high specificity in detecting polymorphisms located within the TEI region. For non-designated polymorphisms in the DA region, the elongation reaction will proceed at a level either comparable to, or lower than that of the perfect match under certain conditions. This is referred to as the tolerance effect of the elongation reaction. Tolerance is utilized in the design of probes to analyze designated and non-designated polymorphisms as described in examples herein.

The density of polymorphic sites in the highly polymorphic loci considered in certain embodiments of this invention makes it likely that probes directed to designated polymorphic sites will overlap adjacent polythorphic sites, when annealing to a target subsequence proximal to the designated polymorphic site. That is, an oligonucleotide probe designed to interrogate the configuration of the target at a selected designated polymorphic site, and constructed with sufficient length to ensure specificity and thermal stability in annealing to the correct target subsequence will align with nearby polymorphic sites. These interfering polymorphic sites may include non-designated sites in the target sequence as well as designated but not selected polymorphic sites Specifically, non-designated polymorphisms as contemplated in the present invention may interfere with duplex formation, thereby interfering with or completely inhibiting probe elongation. In one embodiment, the present invention provides designs of covering probe sets to accommodate such non-designated polymorphisms. A covering probe set contains probes for concurrently interrogating a given multiplicity of designated polymorphic sites within a nucleic acid sequence. A covering probe set comprises, for each site, at least one probe capable of annealing to the target so as to permit, on the basis of a subsequent elongation reaction, assignment of one of two possible values to that site: "matched" (elongation) or "unmatched", (no elongation).

The covering probe set associated with each designated site may contain two or more probes differing in one or more positions, also referred to herein as a degenerate set. In certain embodiments, the probe sequence may contain universal nucleotides capable of forming a base-pair with any of the nucleotides encountered in DNA. In certain embodiments, probes may be attached to encoded microparticles, and specifically, two or more of the probes in a covering set or degenerate set may be attached to the same type of microparticle. The process of attaching two or more probes to a microparticle or bead is referred to as "probe pooling".

The design of covering probe sets is described herein in connection with elongation-mediated multiplexed analysis of polymorphisms in two representative areas of genetic analysis: (1): the scoring of multiple uncorrelated designated polymorphisms and mutations, as in the case of mutation analysis for CF and Ashkenazi Jewish (AJ) disease carrier screening, and (2) the scoring of a correlated set of polymorphisms as in the case of HLA molecular typing. In the first instance, the covering set for the entire multiplicity of mutations contains multiple subsets, each subset being associated with one designated site. In such a case, two or more probes are provided to ascertain heterozygosity. For the purpose of general SNP identification and confirmatory sequencing, degenerate probe sets can be provided to contain up to four labeled (e.g., bead-displayed) probes per polymorphic site. In the second instance, the covering set contains subsets constructed to minimize the number of probes in the set, as elaborated herein. The set of designated probes is designed to identify allele-specific sequence configurations on the basis of the elongation pattern.

While this method of accommodating or identifying non-designated polymorphic sites is especially useful in connection with the multiplexed elongation of sequence specific probes, it also may be used in conjunction with single base extension of probes, also known as mini-sequencing (see e.g., Pastinen, et al. Genome Res. 7: 606-614 (1997), incorporated herein by reference).

The elongation-mediated method of analysis of the present invention, unlike the single-base probe extension method, may be used to detect not only SNPs, but also to detect other types of polymorphisms such as multiple (e.g., double, triple, etc.) nucleotide polymorphisms, as well as insertions and deletions commonly observed in the typing of highly polymorphic genetic loci such as HLA. In these complex systems, sequence-specific probe elongation in accordance with the methods of this invention, simplifies the detection step because two or more probes are provided for each polymorphic target location of interest and the detection step is performed only to determine which of the two or more probes was elongated, rather than to distinguish between two extended probes, as in the case of single-base probe extension Thus, although the methods of this invention accommodate the use of multiple fluorophore or chromophore labels in the detection step, a single universal label generally will suffice for the sequence specific probe elongation. This is in contrast to single-base extension methods whose application in a multiplexed format requires at least two fluorophore or chromophore labels.

DNA Methylation:

In certain embodiments, methods and compositions for determining the methylation status of DNA are provided. Cytosine methylation has long been recognized as an important factor in the silencing of genes in mammalian cells. Cytosine methylation at single CpG dinucleotides within the recognition sites of a number of transcription factors is enough to block binding and related to several diseases. eMAP can be used to determine the methylation status of genomic DNA for diagnostic and other purposes. The DNA is modified by sodium bisulfite treatment converting unmethylated Cytosines to Uracil. Following removal of bisulfite and completion of the chemical conversion, this modified DNA is used as a template for PCR. A pair of probes is designed, one specific for DNA that was originally methylated for the gene of interest, and one specific for unmethylated DNA. eMAP is performed with DNA polymerase and one labeled dNTP and unlabeled mixture of 3 dNTPs or ddNTPs. The elongated product on the specific bead surface can indicate the methylation status.

Selective Sequencing:

In certain other embodiments of this invention, selective sequencing (also referred to as "sequencing") is used for concurrent interrogation of an entire set of designated polymorphisms within a nucleic acid sequence in order to determine the composition at each such site. Selective sequencing can be used to provide the requisite information to select, from the set of possible configurations for the sequence of interest, the actual configuration in a given specific sample or to narrow the set of possible sequences in that sample. In selective sequencing, the length of probes used in an extension reaction determine the length of the sequences that can be determined. For longer DNA sequences, staggered probe designs can be used to link the sequences together. Thus, known sequence combinations can be confirmed, while unknown sequence combinations can be identified as new alleles.

Cystic Fibrosis Carrier Screening—

One practical application of this invention involves the analysis of a set of designated mutations within the context of a large set of non-designated mutations and polymorphisms in the Cystic Fibrosis Transmembrane Conductance (CFTR) gene. Each of the designated mutations in the set is associated with the disease and must be independently scored. In the simplest case of a point mutation, two encoded probes are provided to ensure alignment of their respective 3' termini with the designated site, with one probe anticipating the wild-type, and the other anticipating the altered ("mutated") target sequence.

However, to ensure elongation regardless of the specific target sequence configuration encountered near the designated site, additional probes are provided to match any of the possible or likely configurations, as described in several Example herein. In a preferred embodiment, the covering probe set is constructed to contain probes displaying TEI sequences corresponding to all known or likely variations of the corresponding target subsequence. This ensures elongation in the presence of otherwise elongation-inhibiting non-designated polymorphisms located within a range of proximity of the designated site.

In certain embodiments, the identification of the specific target configuration encountered in the non-designated sites is not necessary so long as one of the sequences provided in the covering probe set matches the target sequence sufficiently closely to ensure elongation, and thus matches the target sequence exactly within the TEI region. In this case, all or some of the covering probes sharing the same 3' terminus may be assigned the same code In a preferred embodiment, such probes may be associated with the same solid support ("probe pooling"). Probe pooling reduces the number of distinguishable solid supports required to represent the requisite number of TEI sequences. In one particularly preferred embodiment, solid supports are provided in the form of a set or array of distinguishable microparticles which may be decoded in-situ. Inclusion of additional probes in the covering probe set to identify additional polymorphisms in the target region is a useful method to elucidate haplotypes for various populations.

HLA—

Another application of this invention involves the genetic analysis of the Human Leukocyte Antigen (HLA) complex, allowing the identification of one or more alleles within regions of HLA encoding class I HLA antigens (preferably HLA-A, HLA-B, HLA-C or any combination thereof) and class II HLA antigens (preferably including HLA-DR, HLA-DQ, HLA-DP or any combination thereof). Class I and II gene loci also may be analyzed simultaneously.

In contrast to the independent scoring of multiple uncorrelated designated mutations, identification of alleles (or groups of alleles) relies on the scoring of an entire set of elongation reactions. Each of these reactions involves one or more probes directed to a member of a selected set of designated polymorphic sites. The set of these elongation reactions produces a characteristic elongation signal pattern. In a preferred embodiment, a binary pattern is produced, assigning a value of "1" to matching (and hence elongated) probes, and a value of "0" to non-elongated probes. The binary pattern ("string") of given length uniquely identifies an allele or a group of alleles.

The total number of probes required for HLA typing depends on the desired resolution. The term "resolution" is used here to indicate the degree of allelic discrimination. Preferably, the method of this invention allows typing of an HLA allele that is sufficient to distinguish different antigen groups. For example, A*01 and A*03 are different antigen groups that have to be distinguished in clinical applications. The National Marrow Donor Program (NMDP) recommended a panel for molecular typing of the donors. The low-to-medium resolution required by the NMDP panel means that different antigen groups should be distinguished at all times. Further, at least some of the alleles within one group should be distinguished, though not necessarily all alleles. In certain embodiments, the present invention allows typing of the HLA allele to a low to medium resolution, as defined by the NMDP standard (www.NMDPresearch.org), incorporated herein by reference.

With such resolution, A*01, A*03 etc., will always be identified. A*0101 and A*0102 may not be necessarily distinguishable. For the SSO method, the current NMDP panel contains 30 probes for HLA-A; 48 for HLA-B and 31 for HLA-DR-B. High resolution HLA typing refers to the situation when most of the alleles will be identified within each group. In this case, A*0101 and A*0102 will be distinguished. To reach such resolution, approximately 500 to 1000 probes will be required for both class I and class II typing. In certain embodiments, the method of the present invention provides high resolution HLA typing, at least to the degree described in Cao, et al., Rev. Immunogenetics, 1: 177-208 (1999), incorporated herein by reference.

This invention also provides strategies for designating sites and for designing probe sets for such designated sites in order to produce unique allele assignments based on the elongation reaction signal patterns. The design of covering probes explicitly takes into account the distinct respective functions of TEI and DA regions of each probe.

A covering set of probes associated with a given designated site is constructed to contain subsets. Each subset in turn contains probes displaying identical TEI regions. A mismatch in a single position within the TEI region, or a mismatch in three or more positions within the DA region precludes elongation. Accordingly, the elongation of two probes displaying such differences in composition generally will produce distinct elongation patterns. All such probes can be multiplexed in a parallel elongation reaction as long as they are individually encoded. In a preferred embodiment, encoding is accomplished by attaching probes to color-encoded beads.

Probes displaying identical TEI subsequences and displaying DA subsequences differing in not more than two positions generally will produce elongation reactions at a yield (and hence signal intensity) either comparable to, or lower than that of a perfect match. In the first case which indicates tolerance of the mismatch, the set of alleles matched by the probe in question will be expanded to include alleles that display the tolerated mismatched sequence configurations within the DA region. In the second case, indicating only partial tolerance, three approaches are described herein to further elucidate the allele matching pattern. In the first approach, probes displaying one or two nucleotide polymorphisms in their respective DA regions are included in the covering set. Information regarding the target sequence is obtained by quantitatively comparing the signal intensities produced by the different probes within the covering set. In the second approach, probes comprising separate TEI and DA regions joined by a tether are used to place the DA region farther away from the TEI region in order to avoid target polymorphisms. In the third approach, probes are optionally pooled in such cases offering only a modest expansion of the set of matched alleles.

In certain embodiments of this invention probes preferably are designed to be complementary to certain target sequences that are known to correlate with allele combinations within the HLA gene locus. Known polymorphisms are those that have appeared in the literature or are available from a searchable database of sequences (e.g., www.NMDProcessing.org). In certain embodiments, the HLA gene of interest belongs to HLA class I group, (e.g., HLA-A, HLA-B or HLA-C or combination thereof). In certain other embodiments, the HLA gene of interest belongs to the HLA class II group, (e.g., DR, DQ, DP or combination thereof). The HLA class I and class II loci may be examined in combination and by way of concurrent interrogation.

Probes previously employed in the SSP/gel method also may be used in this invention. Preferably, the probes set forth in Bunce et al., Tissue Antigen, 46: 355-367 (1995) and/or Bunce et al., Tissue Antigen, 45:81-90 (1995), (each of which are hereby incorporated by reference) are used in preparing the probes for this invention. The probe sequences or HLA sequence information provided in WO 00/65088; European Application No. 98111696.5; WO 00/70006; and Erlich et al., Immunity, 14: 347-356 (2001), (each of which are hereby incorporated by reference) may be used in designing the probes for this invention.

The complexity of an encoded bead array is readily adjusted to accommodate the requisite typing resolution. For example, when 32 types of beads are used for each of four distinct subarrays, a total of 128 probes will be available to attain a medium level of resolution for HLA class I and class II typing in a multiplexed elongation reaction. Analogously, with 128 types of beads and four subarrays, or 64 types of beads and 8 subarrays, a total of 512 probes will be available to attain a high resolution of HLA class I and class II typing in a multiplexed elongation reaction.

The encoded bead array format is compatible with high throughput analysis. For example, certain embodiments of this invention provide a carrier that accommodates multiple samples in a format that is compatible with the dimensions of 96-well microplates, so that sample distribution may be handled by a standard robotic fluid handling apparatus. This format can accommodate multiple encoded bead arrays mounted on chips and permits the simultaneous completion of multiple typing reactions for each of multiple patient samples on a single multichip carrier in a 96-well carrier testing 128 types per patient, more than 10,000 genotypes can be determined at a rate of throughput that is not attainable by current SSP or SSO methodology.

In certain embodiments of this invention, the elongation reaction can be combined with a subsequent hybridization reaction to correlate subsequences on the same DNA target strand, a capability referred to herein as "phasing". Phasing resolves ambiguities in allele assignment arising from the possibility that a given elongation pattern is generated by different combinations of alleles. Similarly, phasing is useful in the context of haplotyping to assign polymorphisms to the same DNA strand or chromosome.

In certain embodiments of this invention, the annealing and elongation steps of the elongation reaction can be combined as a one-step reaction. Furthermore, means to create continuous or discrete temperature variations can be incorporated into the system to accommodate multiple optimal conditions for probes with different melting temperatures in a multiplexed reaction.

In certain embodiments of this invention, encoded bead arrays are formed on solid substrates. These solid substrates may comprise any suitable solid material, such as glass or semiconductor, that has sufficient mechanical strength and can be subjected to fabrication steps, if desired. In some embodiments, the solid substrates are divided into discrete units known as "chips". Chips comprising encoded bead arrays may be processed individually or in groups, if they are loaded into a multichip carrier. For example, standard methods of temperature control are readily applied to set the operating temperature of, or to apply a preprogrammed sequence of temperature changes to, single chips or to multichip carriers. Further, chips may be analyzed with the direct imaging capability of Random Encoded Array Detection ("READ"), as disclosed in PCT/US01/20179, the contents of which are incorporated herein by reference. Using READ, the multiplexed analysis of entire arrays of encoded beads on chips is possible. Furthermore, in the READ format, the application of preprogrammed temperature cycles provides real-time on-chip amplification of elongation products. Given genomic, mitochondrial or other DNA, linear on-chip amplification may obviate the need for pre-assay DNA amplification such as PCR, thereby dramatically shortening the time required to complete the entire typing assay. Time-sensitive applications such as cadaver typing are therefore possible. More importantly, this approach eliminates the complexities of PCR multiplexing, which is a limiting step in many genetic screening and polymorphism analyses. In a preferred embodiment, a fluidic cartridge provides for sample and reagent injection as well as temperature control.

In one embodiment, the invention provides a method for polymorphism analysis in which each target nucleic acid sequence is used as a template in multiple elongation reactions by applying one or more "annealing-extending-detecting-denaturing" temperature cycles. This method achieves linear amplification with in-situ detection of the elongation products. This additional capability obviates the need for a first step of sequence-specific amplification of a polynucleotide sample Integration of assay procedure and signal amplification by way of cycling not only simplifies and accelerates the completion of genetic analysis, but also eliminates the need to develop, test and implement multiplexed PCR procedures. The methods of this invention also provide a high-throughput format for the simultaneous genetic analysis of multiple patient samples.

Several embodiments of this invention are provided for the multiplexed elongation of sequence-specific probes to permit simultaneous evaluation of a number of different targets. In certain embodiments, oligonucleotide probes are immobilized on a solid support to create dense patterns of probes on a single surface, e.g., silicon or glass surface. In certain embodiments, presynthesized oligonucleotide probes are immobilized on a solid support, examples of which include silicon, chemically modified silicon, glass, chemically modified glass or plastic. These solid supports may be in the form of microscopic beads. The resolution of the oligonucicotide array is determined by both spatial resolution of the delivery system and the physical space requirements of the delivered nucleotide solution volume. [See Guo, et al., Nucleic Acids Res. 22: 5456-5465 (1994); Fahy, et al., Nucleic Acid Res. 21: 1819-1826 (1993); Wolf, et al., Nuc. Acids Res. 15: 2911-2926 (1987); and Ghosh, et al., Nuc. Acids Res. 15: 5353-5372 (1987).]

This invention provides methods for multiplexed assays. In certain embodiments, sets of elongation probes are immobilized on a solid phase in a way that preserves their identity, e.g., by spatially separating different probes and/or by chemically encoding the probe identities. One or more solution-borne targets are then allowed to contact a multiplicity of immobilized probes in the annealing and elongation reactions. This spatial separation of probes from one another by immobilization reduces ambiguities in identifying elongation products. Thus, this invention offers advantages over the existing PCR-SSP method, which is not adaptable to a high throughput format because of (i) its requirement for two probes for each PCR amplification; (ii) the competition between overlapping probes for the highly polymorphic genes, such as HLA, in a multiplexed homogeneous reaction; and (iii) the difficulty in distinguishing between specific products in such a multiplexed reaction.

In a preferred embodiment, probes are attached, via their respective 5' termini, to encoded microparticles ("beads") having a chemically or physically distinguishable characteristic that uniquely identifies the attached probe. Probes capture target sequences of interest contained in a solution that contacts the beads. Elongation of the probe displayed on a particular bead produces an optically detectable signature or a chemical signature that may be converted into an optically detectable signature. In a multiplexed elongation reaction, the optical signature of each participating bead uniquely corresponds to the probe displayed on that bead. Subsequent to the probe elongation step, one may determine the identity of the probes by way of particle identification and detection, e.g., by flow cytometry.

In certain embodiments, beads may be arranged in a planar array on a substrate before the elongation step. Beads also may be assembled on a planar substrate to facilitate imaging after the elongation step. The process and system described herein provide a high throughput assay format permitting the instant imaging of an entire array of beads and the simultaneous genetic analysis of multiple patient samples.

The array of beads may be a random encoded array, in which a chemically or physically distinguishable characteristic of the beads within the array indicates the identity of oligonucleotide probes attached to the beads. The array may be formed according to the READ format.

The bead array may be prepared by employing separate batch processes to produce application-specific substrates (e.g., a chip at the wafer scale). Beads that are encoded and attached to oligonucleotide probes (e.g., at the scale of about $10^8$ beads/100 µl suspension) are combined with a substrate (e.g., silicon chip) and assembled to form dense arrays on a designated area of the substrate. In certain embodiments, the bead array contains 4000 beads of 3.2 µm diameter and has a dimension of 300 µm by 300 µm. With beads of different size, the density will vary. Multiple bead arrays also can be formed simultaneously in discrete fluid compartments maintained on the same chip. Such methods are disclosed in U.S. application Ser. No. 10/192,351, filed Jul. 9, 2002, which is incorporated herein by reference in its entirety.

Bead arrays may be formed by the methods collectively referred to as "LEAPS", as described in U.S. Pat. No. 6,251,691 and PCT International Application No. PCT/US00/25466), both of which are incorporated herein by reference.

The substrate (e.g., a chip) used in this invention may be in the form of a planar electrode patterned in accordance with the interfacial patterning methods of LEAPS. For example, the substrate may be patterned with oxide or other dielectric materials to create a desired configuration of impedance gradients in the presence of an applied AC electric field. Patterns may be designed so as to produce a desired configuration of AC field-induced fluid flow and corresponding particle transport. Substrates may be patterned on a wafer scale by using semiconductor processing technology. In addition, substrates may be compartmentalized by depositing a thin film of a UV-patternable, optically transparent polymer to affix to the substrate a desired layout of fluidic conduits and compartments. These conduits and compartments confine fluid in one or several discrete compartments, thereby accommodating multiple samples on a given substrate.

Bead arrays may be prepared using LEAPS by providing a first planar electrode that is in substantially parallel to a second planar electrode ("sandwich" configuration) with the two electrodes being separated by a gap and containing a polarizable liquid medium, such as an electrolyte solution. The surface or the interior of the second planar electrode may be patterned with the interfacial patterning method. The beads are introduced into the gap. When an AC voltage is applied to the gap, the beads form a random encoded array on the second electrode (e.g., a "chip").

In another embodiment of LEAPS, an array of beads may be formed on a light-sensitive electrode (e.g., a "chip"). Preferably, the sandwich configuration described above is also used with a planar light sensitive electrode and another planar electrode. Once again, the two electrodes are separated by the a gap and contain an electrolyte solution. The functionalized and encoded beads are introduced into the gap. Upon application of an AC voltage in combination with light, the beads form an array on the light-sensitive electrode.

In certain embodiments of the present invention, beads may be associated with a chemically or physically distinguishable characteristic. This may be provided, for example, by staining beads with sets of optically distinguishable tags, such as those containing one or more fluorophore or chromophore dyes spectrally distinguishable by excitation wavelength, emission wavelength, excited-state lifetime or emission intensity. The optically distinguishable tags may be used to stain beads in specified ratios, as disclosed, for example, in Fulwyler, U.S. Pat. No. 4,717,655 (Jan. 5, 1988). Staining may also be accomplished by swelling of particles in accordance with methods known to those skilled in the art, (Molday, Dreyer, Rembaum & Yen, J. Mol Biol 64, 75-88 (1975); L. Bangs, "Uniform latex Particles, Seragen Diagnostics, 1984). For example, up to twelve types of beads were encoded by swelling and bulk staining with two colors, each individually in four intensity levels, and mixed in four nominal molar ratios. Alternatively, the methods of combinatorial color encoding described in International Application No. PCT/US 98/10719 (incorporated by reference in its entirety) can be used to endow the bead arrays with optically distinguishable tags. In addition to chemical encoding, beads may also be rendered magnetic by the processes described in PCT/USO/20179.

In addition to chemical encoding with dyes, beads having certain oligonucleotide primers may be spatially separated ("spatial encoding"), such that the location of the beads provides information as to the identity of the beads. Spatial encoding, for example, can be accomplished within a single fluid phase in the course of array assembly by using Light-controlled Electrokinetic Assembly of Particles near Surfaces (LEAPS). LEAPS can be used to assemble planar bead arrays in any desired configuration in response to alternating electric fields and/or in accordance with patterns of light projected onto the substrate.

LEAPS can be used to create lateral gradients in the impedance at the interface between a silicon chip and a solution to modulate the electrohydrodynamics forces that mediate array assembly. Electrical requirements are modest: low AC voltages of typically less than $10V_{pp}$ are applied across a fluid gap between two planar electrodes that is typically 100 µm. This assembly process is rapid and it is optically programmable: arrays containing thousands of beads are formed within seconds under an applied electric field. The formation of multiple subarrays can also occur in multiple fluid phases maintained on a compartmentalized chip surface.

Subsequent to the formation of an array, the array may be immobilized. For example, the bead arrays may be immobilized, for example, by application of a DC voltage to produce random encoded arrays. The DC voltage, set to typically 5-7 V (for beads in the range of 2-6 µm and for a gap size of 100-150 µm) and applied for <30 s in "reverse bias" configuration so that an n-doped silicon substrate would form the anode, causes the array to be compressed to an extent facilitating contact between adjacent beads within the array and simultaneously causes beads to be moved toward the region of high electric field in immediate proximity of the electrode surface. Once in sufficiently close proximity, beads are anchored by van der Waals forces mediating physical adsorption. This adsorption process is facilitated by providing on the bead surface a population of "tethers" extending from the bead surface; polylysine and streptavidin have been used for this purpose.

In certain embodiments, the particle arrays may be immobilized by chemical means, e.g., by forming a composite gel-particle film. In one exemplary method for forming such gel-composite particle films, a suspension of microparticles is provided which also contains monomer, crosslinker and initiator for in-situ gel formation. The particles are assembled into a planar assembly on a substrate by using LEAPS. AC voltages of 1-20 $V_{pp}$ in a frequency range from 100's of hertz to several kilohertz are applied between the electrodes across the fluid gap. In the presence of the applied AC voltage, polymerization of the fluid phase is triggered after array assembly by thermally heating the cell to ~40-45° C. using an infra-red (IR) lamp or photoinitiating the reaction using a mercury lamp source. The resultant gel effectively entraps the particle array. Gels may be composed of a mixture of acrylamide and bisacrylamide of varying monomer concentrations from 20% to 5% (acrylamide:bisacrylamide=37.5:1, molar ratio), but any other low viscosity water soluble monomer or monomer mixture may be used as well. Chemically immobilized functionalized microparticle arrays prepared by this process may be used for a variety of bioassays, e.g., ligand receptor binding assays.

In one example, thermal hydrogels are formed using azodiisobutyramidine dihydrochloride as a thermal initiator at a low concentration to ensure that the overall ionic strength of the polymerization mixture falls in the range of ~0.1 mM to 1.0 mM. The initiator used for the UV polymerization is Irgacure 2959® (2-Hydroxy-4'-hydroxyethoxy-2-methylpropiophenone, Ciba Geigy, Tarrytown, N.Y.). The initiator is added to the monomer to give a 1.5% by weight solution.

In certain embodiments, the particle arrays may be immobilized by mechanical means. For example, an array of microwells may be produced by standard semiconductor processing methods in the low impedance regions of a silicon substrate. Particle arrays may be formed using such structures. In certain embodiments LEAPS mediated hydrodynamic and ponderomotive forces are utilized to transport and to accumulate particles on the hole arrays. The AC field is then switched off and particles are trapped into microwells and thus mechanically confined Excess beads are removed leaving behind a spatially ordered random bead array on the substrate surface.

Substrates (e.g., chips) can be placed in one or more enclosed compartments that permit samples and reagents to be transported in and out of the compartments through fluidic interconnection. Reactions can also be performed in an open compartment format such as a microtiter plate. Reagents may be pipetted on top of the chip by robotic liquid handling equipment, and multiple samples may be processed simultaneously. Such a format accommodates standard sample processing and liquid handling for the existing microtiter plate format and integrates sample processing and array detection.

In certain embodiments of this invention, encoded beads are assembled on the substrate surface, but not in an array. For example, by spotting bead suspensions into multiple regions of the substrate and allowing beads to settle under gravity, assemblies of beads can be formed on the substrate. In contrast to the bead arrays formed by LEAPS, these assemblies generally assume disordered configurations of low-density or non-planar configurations involving stacking or clumping of beads, thereby preventing imaging of affected beads. However, the combination of spatial and color encoding attained by spotting mixtures of chemically encoded beads into a multiplicity of discrete positions on the substrate still allows multiplexing.

In certain embodiments, a comparison of an image of an array after the assay with a decoded image of the array can be used to reveal chemically or physically distinguishable characteristics, as well as the elongation of probes. This comparison can be achieved by using, for example, an optical microscope with an imaging detector and computerized image capture and analysis equipment. The assay image of the array is taken to detect the optical signature that indicates the probe elongation. The decoded image is taken to determine the chemically and/or physically distinguishable characteristics that uniquely identify the probe displayed on the bead surface. In this way, the identity of the probe on each particle in the array may be identified by a distinguishable characteristic.

Image analysis algorithms may be used in analyzing the data obtained from the decoding and the assay images. These algorithms may be used to obtain quantitative data for each bead within an array. The analysis software automatically locates bead centers using a bright-field image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances. Examples of such algorithms are set forth in PCT/US01/120179.

Probe elongation may be indicated by a change in the optical signature, or a change in chemical signature which may be converted to a change in optical signature, originating from the beads displaying elongated probes, for example. Direct and indirect labeling methods well known in the art are available for this purpose. Direct labeling refers to a change in optical signature resulting from the elongation; indirect labeling refers to a change introduced by elongation which requires one or more additional steps to produce a detectable optical signature.

In certain embodiments, fluorophore or chromophore dyes may be attached to one of the nucleotides added as an ingredient of probe elongation, such that probe elongation changes the optical signature of beads by changing, for example, fluorescence intensities or by providing other changes in the optical signatures of beads displaying elongation products.

EXAMPLES

The present invention will be better understood from the Examples which follow. It should be understood that these examples are for illustrative purposes and are not to be construed as limiting this invention in any manner.

Example 1: Staggered Probe Design for Multiplexed SSP Analysis

Figure 1B:
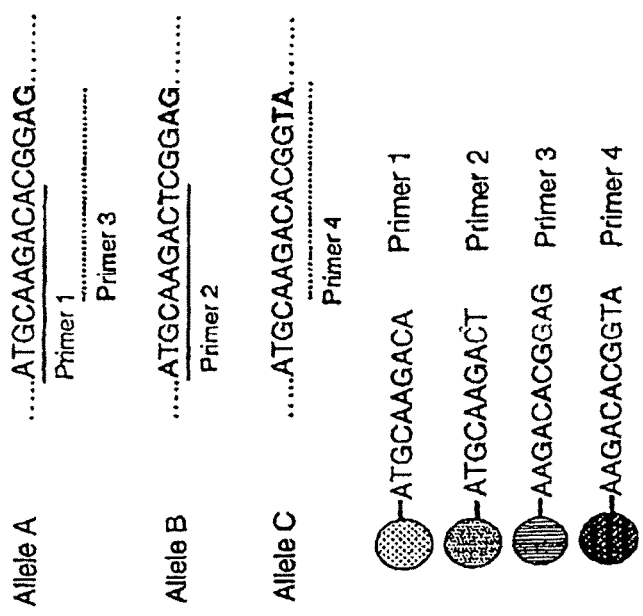
FIG. 1b is an illustration of a staggered primer design.

Probes for each polymorphism are immobilized on a solid phase carrier to provide a format in which multiple concurrent annealing and extension reactions can proceed with minimal mutual interference. Specifically, this method provides a design which accommodates overlapping probes, as illustrated in FIG. 1. In this example, we consider three alleles: allele A, allele B and allele C. Probes 1 and 2 detect SNPs that are aligned with their respective 3' termini while probes 3 and 4 detect two-nucleotide polymorphisms that are aligned with their respective 3' termini. The polymorphic sites targeted by probes 1 and 2 are located five nucleotides upstream of those targeted by probes 3 and 4. This design permits each probe to bind its corresponding target and permits elongation to proceed when there is a perfect match at the designated polymorphic site. Thus, probes 1 and 3 match allele A, probe 2 and possibly probe 3 match allele B, and probes 1 and 4 match allele C Example 2: Probe Design for HLA Typing To design probes for the analysis of the polymorphic region ranging from base 106 to base 125 of the DRB gene, twenty-two different types of sequences for the 20 base long fragment were located in the DRB database. These are listed in the table below:

| | | | |
|---|---|---|---|
| 7 | DRB1*0101 | SEQ. ID NO.: 1 | TTCTTGTGGCAGCTTAAGTT |
| 104 | DRB1*03011 | SEQ. ID NO.: 2 | TTCTTGGAGTACTCTACGTC |
| 26 | DRB1*04011 | SEQ. ID NO.: 3 | TTCTTGGAGCAGGTTAAACA |
| 1 | DRB1*0434 | SEQ. ID NO.: 4 | TTCTTGGAGCAGGTTAAACC |
| 3 | DRB1*07011 | SEQ. ID NO.: 5 | TTCCTGTGGCAGGGTAAGTA |
| 1 | DRB1*07012 | SEQ. ID NO.: 6 | TTCCTGTGGCAGGGTAAATA |
| 28 | DRB1*0801 | SEQ. ID NO.: 7 | TTCTTGGAGTACTCTACGGG |
| 1 | DRB1*0814 | SEQ. ID NO.: 8 | TTCTTGGAGTACTCTAGGGG |
| 1 | DRB1*0820 | SEQ. ID NO.: 9 | TTCTTGGAGTACTCTACGGC |
| 1 | DRB1*0821 | SEQ. ID NO.: 10 | TTCTTGGAGTACTCTATGGG |
| 1 | DRB1*09012 | SEQ. ID NO.: 11 | TTCTTGAAGCAGGATAAGTT |
| 2 | DRB1*10011 | SEQ. ID NO.: 12 | TTCTTGGAGGAGGTTAAGTT |
| 1 | DRB1*1122 | SEQ. ID NO.: 13 | TTCTTGGAGCAGGCTACACA |
| 1 | DRB1*1130 | SEQ. ID NO.: 14 | TTCTTGGAGTTCCTTAAGTC |
| 18 | DRB1*15011 | SEQ. ID NO.: 15 | TTCCTGTGGCAGCCTAAGAG |
| 9 | DRB3*01011 | SEQ. ID NO.: 16 | TTCTTGGAGCTGCGTAAGTC |
| 1 | DRB3*0102 | SEQ. ID NO.: 17 | TTCTTGGAGCTGTGTAAGTC |
| 1 | DRB3*0104 | SEQ. ID NO.: 18 | TTCTCGGAGCTGCGTAAGTC |
| 16 | DRB3*0201 | SEQ. ID NO.: 19 | TTCTTGGAGCTGCTTAAGTC |
| 1 | DRB3*0212 | SEQ. ID NO.: 20 | TTCTTGCAGCTGCTTAAGTC |
| 6 | DRB4*01011 | SEQ. ID NO.: 21 | TTCTTGGAGCAGGCTAAGTG |
| 14 | DRB5*01011 | SEQ. ID NO.: 22 | TTCTTGCAGCAGGATAAGTA |

The first column contains the number of alleles sharing the sequence listed in third column, the second column contains one of the allele names We selected the last three bases of the 20-base fragment as the TEI region and sorted the set of sequences according to their TEI region to obtain the following groups:

| | | | | |
|---|---|---|---|---|
| 1 | 104 | DRB1*03011 | SEQ. ID NO.: 23 | TTCTTGGAGTACTCTACGTCe1 |
| | 1 | DRB1*1130 | SEQ. ID NO.: 24 | TTCTTGGAGTGCctTAaGTC |
| | 9 | DRB3*01011 | SEQ. ID NO.: 25 | TTCTTGGAGctgcgTAaGTC |
| | 1 | DRB3*0102 | SEQ. ID NO.: 26 | TTCTTGGAGctgTgTAaGTC |
| | 1 | DRB3*0104 | SEQ. ID NO.: 27 | TTCTcGGAGctgcgTAaGTC |
| | 16 | DRB3*0201 | SEQ. ID NO.: 28 | TTCTTGGAGctgctTAaGTCe2 |
| | 1 | DRB3*0212 | SEQ. ID NO.: 29 | TTCTTGcAGctgctTAaGTC |
| 2 | 7 | DRB1*0101 | SEQ. ID NO.: 30 | TTCTTGTGGCAGCTTAAGTT |
| | 1 | DRB1*09012 | SEQ. ID NO.: 31 | TTCTTGaaGCAGgaTAAGTT |
| | 2 | DRB1*10011 | SEQ. ID NO.: 32 | TTCTTGgaGGAGgTTAAGTT |
| 3 | 26 | DRB1*04011 | SEQ. ID NO.: 33 | TTCTTGGAGCAGGTTAAACA |
| | 1 | DRB1*1122 | SEQ. ID NO.: 34 | TTCTTGGAGCAGGcTAcACA |
| 4 | 1 | DRB1*0434 | SEQ. ID NO.: 35 | TTCTTGGAGCAGGTTAAACC |
| 5 | 3 | DRB1*07011 | SEQ. ID NO.: 36 | TTCCTGTGGCAGGGTAAGTA |
| | 14 | DRB5*01011 | SEQ. ID NO.: 37 | TTCtTGcaGCAGGaTAAGTA |
| 6 | 1 | DRB1*07012 | SEQ. ID NO.: 38 | TTCCTGTGGCAGGGTAAATA |
| 7 | 28 | DRB1*0801 | SEQ. ID NO.: 39 | TTCTTGGAGTACTCTACGGGe3 |
| | 1 | DRB1*0814 | SEQ. ID NO.: 40 | TTCTTGGAGTACTCTAgGGG |
| | 1 | DRB1*0821 | SEQ. ID NO.: 41 | TTCTTGGAGTACTCTAtGGG |
| 8 | 1 | DRB1*0820 | SEQ. ID NO.: 42 | TTCTTGGAGTACTCTACGGC |

```
 9   18 DRB1*SEQ. ID NO.: 43 TTCCTGTGGCAGCCTAAGAG
        15011

10    6 DRB4*SEQ. ID NO.: 44 TTCTTGGAGCAGGCTAAGTG
        01011
```

For sequences in the same group, variations between the first sequence of the group and the rest are indicated in lower case. Three probe sequences are used to illustrate the application of our probe design rules. The first sequence in the first group is selected as probe e1; the 6th sequence in the first group is selected as probe e2; and the first group in the 7th sequence is selected as probe e3.

Due to requirement for perfect complementarity of the target and the probe's TEI region, sequences in group 2 to group 10 do not produce elongation products for e1 and e2.

Similarly, sequences in groups other than the 7th group do not produce elongation products for e3. Each group is distinctive from the others with respect to elongation reaction patterns.

For sequences in the same group, there are two types of situations. For example, e1 and e2 differ by one nucleotide in 6 positions within the annealing region. Thus, targets matching e1 and e2 will not produce elongation products for the other sequences, and e1 and e2 are also distinct probes.

Similarly, targets for the second to the 7th sequences in group 1 will not produce elongation products for probe e1.

Except for the target matching e1, the remaining 5 sequences only differ from e2 by one or two nucleotides as indicated below:

```
                              1, 2 . . . M

16 DRB3*0201  SEQ. ID NO.: 45 TTCTTGGAGCTGCTTAAGTCe2

1 DRB1*1130  SEQ. ID NO.: 46 TTCTTGGAGtTcCTTAAGTCa

9 DRB3*01011 SEQ. ID NO.: 47 TTCTTGGAGCTGCgTAAGTCb

1 DRB3*0102  SEQ. ID NO.: 48 TTCTTGGAGCTGtgTAAGTCc

1 DRB3*0104  SEQ. ID NO.: 49 TTCTcGGAGCTGCgTAAGTCd

1 DRB3*0212  SEQ. ID NO.: 50 TTCTTGcAGCTGCTTAAGTCE
```

These sequences are cross-reactive. When targets for sequences b and e, which differ from e2 by one base at respective positions M–7 and M–14 anneal to probe e2, the non-designated polymorphism(s) in the annealing region will be tolerated and the elongation reaction will proceed to substantially the same degree as for perfectly matched sequences. When targets for sequences a, c, and d, which differ from e2 by two nucleotides anneal to probe e2, the elongation reaction will exhibit only partial tolerance of the non-designated polymoprhism(s). One approach to improve on this situation is to provide separate probes for a, c, and d, then quantitatively analyze the yield of elongation products by analyzing signals intensities to identify the correct sequences. An alternative would be to bridge the non-designated polymorphisms in the annealing region altogether by adding a physical linker (e.g., a tether) to the e2 probe to be able to separate annealing and TEI regions.

For the sequences in the 7th group, the other two sequences will be partially tolerated by the e3 probe. These three sequences may be pooled. The e2 probe will yield elongation products for 30 alleles instead of 28 alleles.

Example 3: Utilizing Mismatch Tolerance to Modify Allele Binding Patterns

Figure 2:
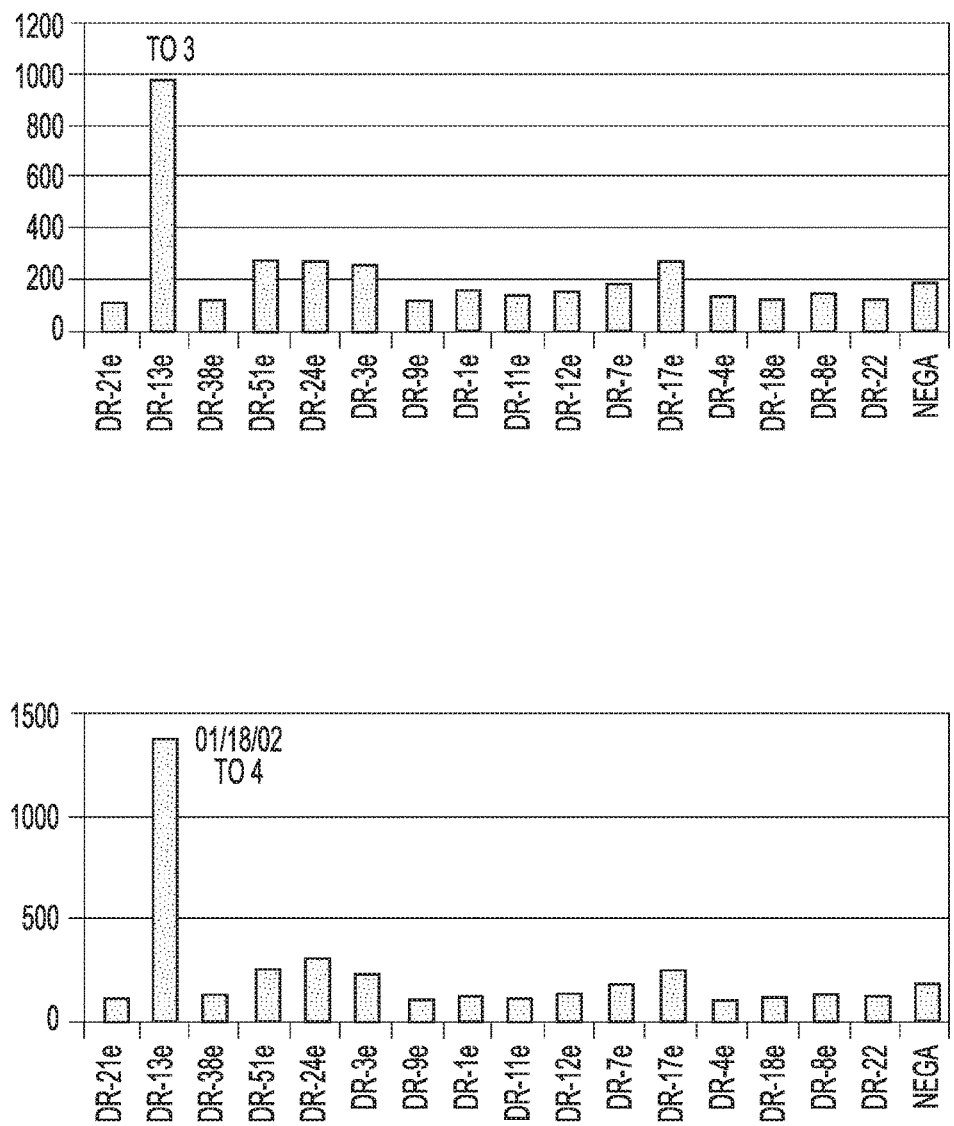
FIG. 2 is an illustration of a modification of allele binding pattern based on tolerance effect.

Probe DR-13e, SEQ. ID NO.: 51, GACATCCTG-GAAGACGA, was used to target the bases 281-299 of the DRB gene. Thirty-four alleles, including allele DRB1*0103, are perfectly matched to this sequence. Thus, in the binding pattern, 13e is positive for theses 34 alleles (that is, 13e will yield elongation products with these 34 alleles). Several additional alleles display the same TEI region but display non-designated polymorphisms in their respective annealing regions. For example, five alleles, such as DRB1*0415, contain T in instead of A in position 4 while four alleles, such as DRB1*1136, contain C in the that position. Due to mismatch tolerance in the annealing region, target sequences complementary to these nine alleles will produce elongation reaction patterns similar to that of the perfectly matched sequence. The result is shown in FIG. 2. TO-3 and TO-4 are completely complementary sequences to allele *0415 and *1136, respectively.

```
DRB1*0103 SEQ. ID NO.: 51 GACATCCTGGAAGACGA  34
                                             alleles DRB1*0415 SEQ. ID NO.: 52 GACTTCCTGGAAGACGA   5
                                             alleles DRB1*1136 SEQ. ID NO.: 53 GACCTCCTGGAAGACGA   4
                                             alleles
```

Figure 3:
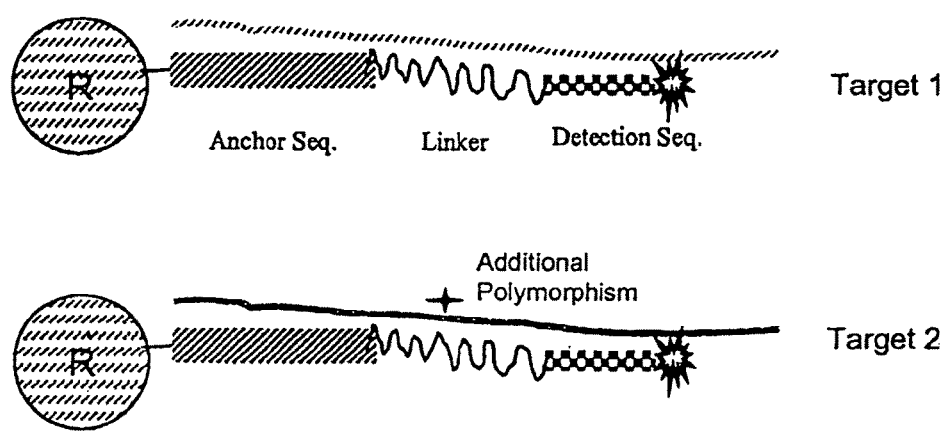
FIG. 3 is an illustration of the use of linked primer structure to separate the anchoring sequence and polymorphism detection sequence.

Example 4: Design of Linker Structure in the Probes to Bridge Non-Designated Polymorphisms As illustrated in FIG. 3, an anchor sequence is derived from conserved sequence regions to ensure specific and strong annealing. It is not designed for polymorphism detection. For that purpose, a shorter sequence for polymorphism detection is attached to the anchoring sequence by way of a neutral chemical linker. The shorter length of the sequence designed for polymorphism detection will limit potential interference to non-designated polymorphisms in the immediate vicinity of the designated site and thus decreases the number of possible sequence combinations required to accommodate such interfering polymorphisms This approach avoids highly dense polymorphic sites in certain situations. For example, it would be possible to distinguish between the sequences listed in Example 3 using a probe which takes into account the additional polymorphism(s). Illustrative designs of the linker and the sequences are listed below:

```
linker    (SEQ. ID NO.: 54)  AGCCAGAAGGAC/Spacer
13-5                         18/spacer 18/GGAAGACGA linker    (SEQ. ID NO.: 54)  AGCCAGAAGGAC/Spacer
13-8                         18/spacer 18/AGACGA linker    (SEQ. ID NO.: 54)  AGCCAGAAGGAC/Spacer
13-11                        18/spacer 18/CGA
```

Example 5: Phasing

Figure 5:
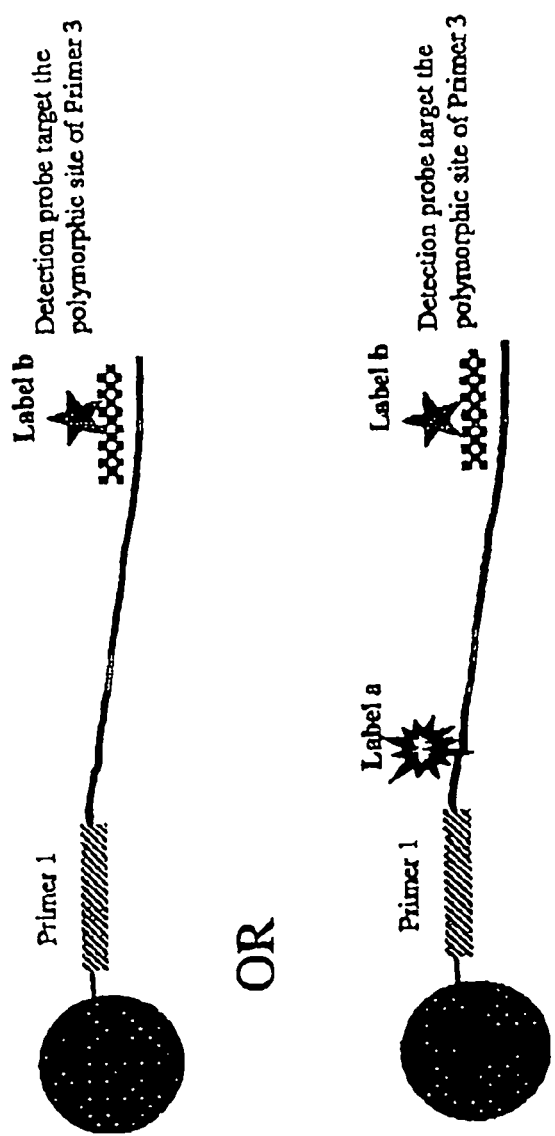
FIG. 5 shows one method for decreasing the ambiguity in allele identification that arises from allele combination.

The present invention also is useful in reducing ambiguities that arise when two or more allele combinations can produce the same reaction pattern. In a simulated situation shown in FIGS. 4 and 5, allele A which matches—and hence produces an elongation product with—Probe 1 and Probe 3, and allele B, which matches Probe 2 and Probe 4 when present in the same multiplexed reaction, generate the same total reaction pattern as does the combination of allele C which matches Probe 1 and 2, and allele D which matches Probe 3 and Probe 4. Such ambiguity can be reduced or eliminated by using the detection methods provided in this invention to analyze the elongation product of Probe 1 by hybridization using a labeled detection probe that is designed to target the same polymorphic site as Probe 3. If the result of the analysis is positive, only one allele combination, namely combination 1, is possible because Probe 1 and Probe 3 are associated with the same allele. The detection probe can be labeled by using any of the methods disclosed in this invention or methods known in the art. If this identification detection step is performed together with the multiplexed elongation reaction detection, different labels are used for the elongation detection and probe hybridization detection as shown in the FIG. 5.

In this method, the ambiguity is resolved by assigning two or more polymorphisms to the same "phase" using elongation in conjunction with hybridization. Phasing is rapidly emerging as an important concern for haplotype analysis in other genetic studies designed in the art. More probes can be included by reacting them with the target sequentially, or they can be arranged in the same reaction with different labels for detection.

Figure 6:
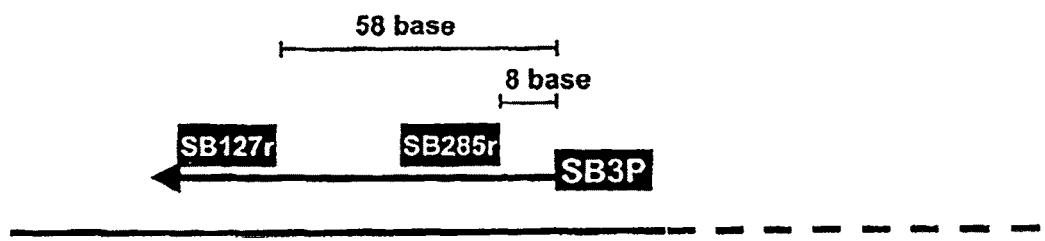
FIG. 6 is an illustration of a combination of hybridization and elongation.
Figure 6:
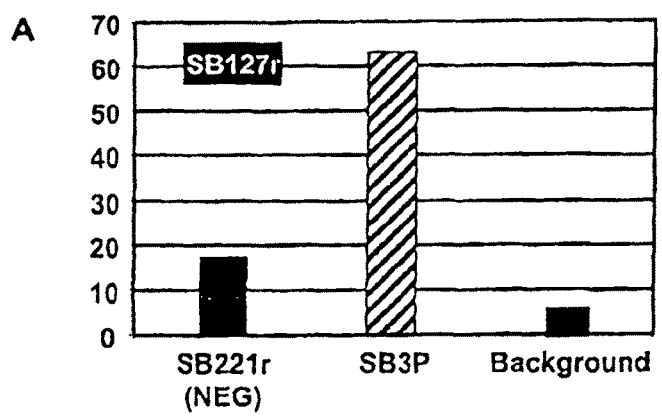
Figure 6:
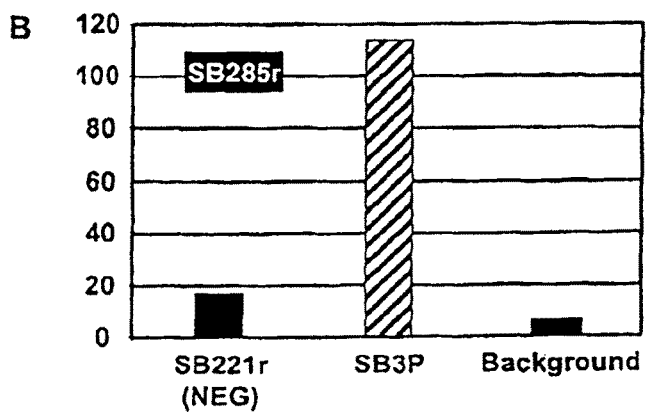

The capability of combining probe elongation and hybridization reactions is demonstrated in experiments using a sample sequence from HLA-B exon 3. The result is shown in FIG. 6. A probe SB3P was elongated in the reaction and the elongated product was detected using a labeled DNA probe. For the two samples presented in FIGS. 6A and 6B, SB 127r and SB3P, and SB285r and SB3P are in the same phase, respectively.

Example 6: Model HLA Typing Reaction Using Random Encoded Probe Arrays

To illustrate the discrimination of polymorphisms, a model reaction was performed using a synthetic single strand as the target. Color encoded, tosyl-functionalized beads of 3.2 µm diameter were used as solid phase carriers. A set of 32 distinguishable color codes was generated by staining particles using standard methods known in the art (Bangs. L. B., "Uniform Latex Particles", Seragen Diagnostics Inc., p.40) and using different combinations of blue dye (absorption/emission 419/466 nm) and green dye (absorption/emission 504/511). Stained beads were functionalized with Neutravidin (Pierce, Rockford, Ill.), a biotin binding protein, to mediate immobilization of biotinylated probes. In a typical small-scale coupling reaction, 200 µl of suspension containing 1% beads were washed three times with 500 µl of 100 mM phosphate buffer/pH 7.4 (buffer A) and resuspended in 500 µl of that buffer. After applying 20 µl of 5 mg/ml neutravidin to the bead suspension, the reaction was sealed and allowed to proceed overnight at 37° C. Coupled beads were then washed once with 500 µl of PBS/pH 7.4 with 10 mg/ml BSA (buffer B), resuspended in 500 µl of that buffer and reacted for 1 hour at 37° C. to block unreacted sites on bead surface. After blocking, beads were washed three times with buffer B and stored in 200 µl of that buffer.

In the model reaction system, two pairs of probes were synthesized to contain SNPs at their respective 3' termini. The respective sequences were as follows:

```
SSP13:
SEQ. ID NO.: 55    AAGGACATCCTGGAAGACG;

SSP24:
SEQ. ID NO.: 56    AAGGACATCCTGGAAGACA;

SSP16:
SEQ. ID NO.: 57    ATAACCAGGAGGAGTTCC;

SSP36:
SEQ. ID NO.: 58    ATAACCAGGAGGAGTTCG.
```

The probes were biotinylated at the 5' end; a 15-carbon triethylene glycol linker was inserted between biotin and the oligonucleotide to minimize disruptive effects of the surface immobilization on the subsequent reactions. For each probe, coupling to encoded beads was performed using 501.11 of bead suspension. Beads were washed once with 500 µl of 20 mM Tris/pH 7.4, 0.5M NaCl (buffer C) and resuspended in 300 µl of that buffer, 2.5 µl of a 100 µM solution of probe were added to the bead suspension and allowed to react for 30 mM at room temperature. Beads were then washed three times with 20 mM Tris/pH 7.4, 150 mM NaCl, 0.01% triton and stored in 20 mM Tris/pH 7.4, 150 mM NaCl.

The following synthetic targets of 33 bases in length were provided:

```
TA16:
SEQ. ID NO.: 59  GTCGAAGCGCAGGAACTCCTCCTGGTTATGGAA

TA36:
SEQ. ID NO.: 60  GTCGAAGCGCACGAACTCCTCCTGGTTATAGAA

TA13:
SEQ. ID NO.: 61  GGCCCGCTCGTCTTCCAGGATGTCCTTCTGGCT

TA24:
SEQ. ID NO.: 62  GGCCCGCTTGTCTTCCAGGATGTCCTTCTGGCT
```

Figure 7:
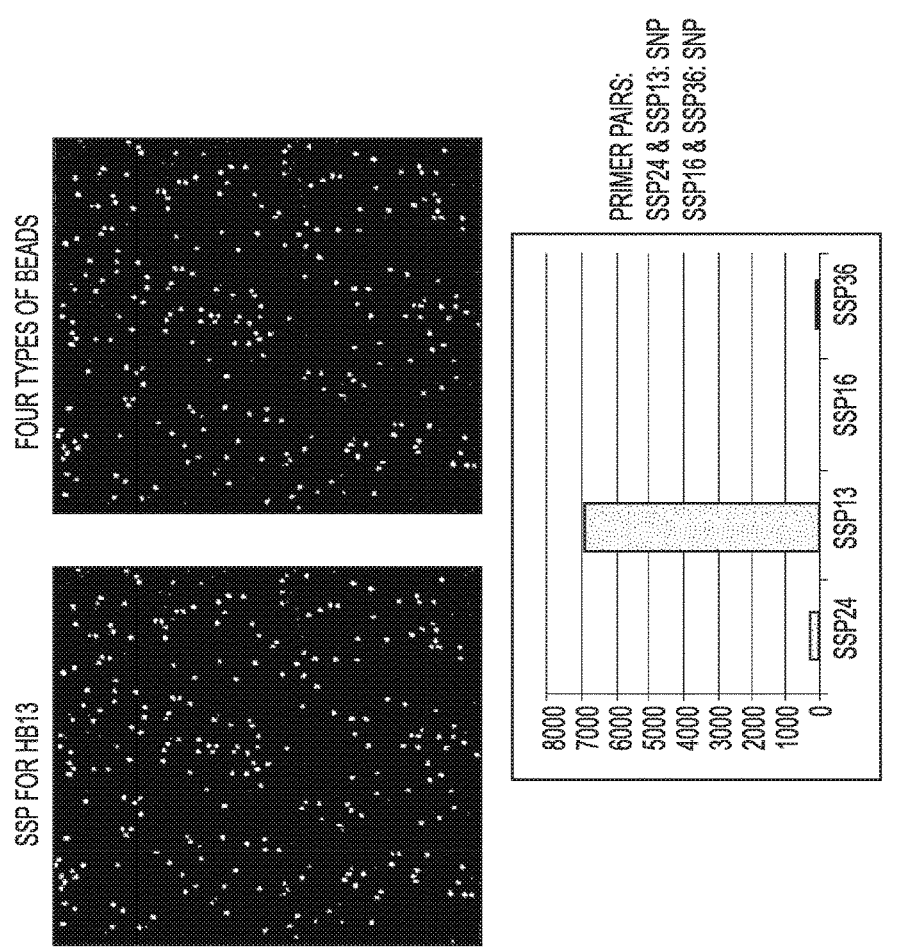
FIG. 7 shows a model reaction using synthetic oligonucleotides as targets.

Targets were allowed to react with four probes (SSP13, SSP24, SSP16, SSP36) on the chip. An aliquot of 10 µl of a 100 nM solution of the target in annealing buffer of 0.2 M NaCl, 0.1% Triton X-100, 10 mM Tris/pH 8.0, 0.1 mM EDTA was applied to the chip and allowed to react for 15 min at 30° C. The chip was then washed once with the same buffer and was then covered with an extension reaction mixture including: 100 nM of TAMRA-ddCTP (absorption/emission: 550/580) (PerkinElmer Bioscience, Boston, Mass.), 10 µM dATP-dGTP-dTTP, ThermoSequenase (Amersham, Piscataway, N.J.) in the associated buffer supplied by the manufacturer. The reaction was allowed to proceed for 5 min at 60° C., and the chip was then washed in H$_2$O. Decoding and assay images of the chip were acquired using a Nikon fluorescence E800 microscope with an automated filter changer containing hydroxy coumarin, HQ narrow band GFP and HQ Cy3 filters for blue, green decoding images and for the assay image, respectively. An Apogee CCD KX85 (Apogee Instruments, Auburn, Calif.) was used for image acquisition. In each reaction, only the perfectly matching target was extended producing, in the case of the SNPs tested here, discrimination between matching and non-matching targets in the range from 13-fold to 30-fold; this is illustrated in FIG. 7 for TA13.

Example 7: HLA-DR Typing of Patient Sample

A DNA sample extracted from a patient was processed using a standard PCR protocol. The following primers were used for general DR amplification:

```
forward    SEQ. ID NO.: 63  GATCCTTCGTGTCCCCACAGCACG
primer:

reverse    SEQ. ID NO.: 64  GCCGCTGCACTGTGAAGCTCTC.
primer:
```

The PCR protocol was as follows: one cycle of 95° C. for 7 min, 35 cycles of 95° C. for 30 sec, 60° C. for 30 sec and 72° C. for 1 min and one cycle of 72° C. for 7 min.

The PCR product, 287 bases in length and covering the DR locus, was denatured at 100° C. for 5 min, chilled on ice and mixed with annealing buffer as described in Example 6 for the model reaction. An aliquot of 10 ul was applied to each chip and reacted at 40° C. for 15 min. The elongation reaction and subsequent image acquisition proceeded as in the previous Example 6.

Figure 8:
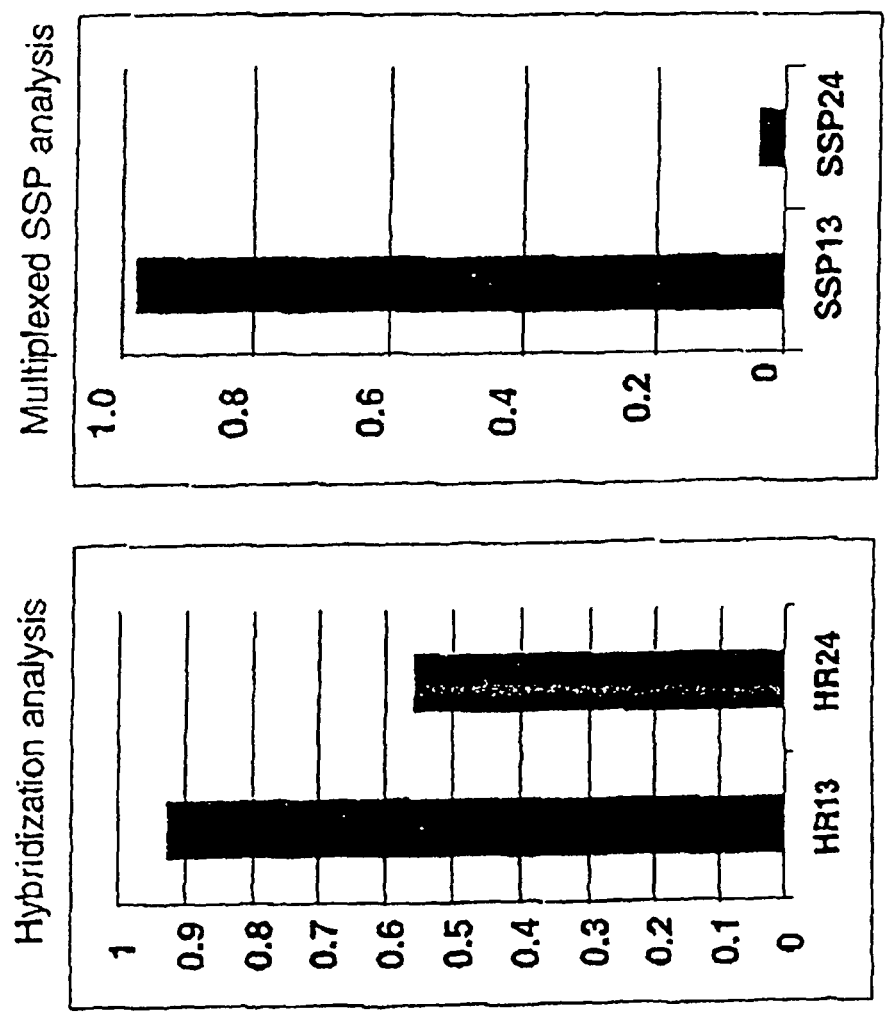
FIG. 8 shows results obtained using testing real patient sample in an eMAP format.

The multiplexed extension of sequence-specific probes using the PCR product produced from the patient sample produced results in accordance with the probe design. Of the four probes tested in parallel (SSP13, SSP16, SSP24, SSP36), SSP13 was elongated while the SNP probe SSP24 only showed background binding as did the unrelated SSP16 and SSP36 probes. As illustrated in FIG. 8, the multiplexed elongation of SSP significantly enhanced the discrimination between matching and non-matching SNPs from approximately two-fold for an analysis based on the hybridization of matching and non-matching sequence-specific oligonucleotide probes to at least 20-fold.

Example 8: Group-Specific Amplification

Primers for group-specific amplification (GSA) are most frequently used when multiplexed hybridization with SSOs yields ambiguous assignments of heterozygous allele combinations. In such a situation, GSA primers are selected to amplify selected sets of specific alleles so as to remove ambiguities, a labor-intensive additional assay step which delays the analysis. Using the methods of the present invention, preferably an embodiment of displaying probes on random encoded bead arrays, GSA primers may be incorporated as probes into the multiplexed reaction thereby eliminating an entire second step of analysis.

Example 9: Analysis of HLA-DR, -A and -B Loci Using Cell Lines

Probes for the elongation-mediated multiplexed analysis of HI,A-DR, HLA-A and HLA-B were designed and tested using standard cell lines. The probes were derived from SSP probes previously reported in the literature (Bunce, M. et al, Tissue Antigens. 46:355-367 (1995), Krausa, P and Browning, M. J., Tissue Antigens. 47: 237-244 (1996), Bunce, M. et al, Tissue Antigens. 45:81-90 (1995)).

The probes used for DR were:

```
SR2:   SEQ. ID NO.: 65  ACGGAGCGGGTGCGGTTG
SR3:   SEQ. ID NO.: 66  GCTGTCGAAGCGCACGG
SR11:  SEQ. ID NO.: 67  CGCTGTCGAAGCGCACGTT
SR19:  SEQ. ID NO.: 68  GTTATGGAAGTATCTGTCCAGGT
SR23:  SEQ. ID NO.: 69  ACGTTTCTTGGAGCAGGTTAAAC
SR32:  SEQ. ID NO.: 70  CGTTTCCTGTGGCAGGGTAAGTATA
SR33:  SEQ. ID NO.: 71  TCGCTGTCGAAGCGCACGA
SR36:  SEQ. ID NO.: 72  CGTTTCTTGGAGTACTCTACGGG
SR39:  SEQ. ID NO.: 73  TCTGCAGTAGGTGTCCACCA
SR45:  SEQ. ID NO.: 74  CACGTTTCTTGGAGCTGCG
SR46:  SEQ. ID NO.: 75  GGAGTACCGGGCGGTGAG
SR48:  SEQ. ID NO.: 76  GTGTCTGCAGTAATTGTCCACCT
SR52:  SEQ. ID NO.: 77  CTGTTCCAGGACTCGGCGA
SR57:  SEQ. ID NO.: 78  CTCTCCACAACCCCGTAGTTGTA
SR58:  SEQ. ID NO.: 79  CGTTTCCTGTGGCAGCCTAAGA
SR60:  SEQ. ID NO.: 70  CACCGCGGCCCGCGC
SR67:  SEQ. ID NO.: 81  GCTGTCGAAGCGCAAGTC
SR71:  SEQ. ID NO.: 82  GCTGTCGAAGCGCACGTA
NEG    SEQ. ID NO.: 83  AAAAAAAAAAAAAAAAA
```

Some of the probes have a SNP site at their respective 3' termini, for example: SR3 and SR33 (G and A, respectively); SR11, SR67 and SR71 (T, C, and A, respectively). In addition, probes SR3 and 33 are staggered at the 3'-end with respect to probes the group of SR11, 67 and 71 by one base.

```
SR3    SEQ. ID NO.: 84  GCTGTCGAAGCGCACGG
SR33   SEQ. ID NO.: 85  TCGCTGTCGAAGCGCACGA
SR11   SEQ. ID NO.: 86  CGCTGTCGAAGCGCACGTT
SR67   SEQ. ID NO.: 87  GCTGTCGAAGCGCAAGTC
SR71   SEQ. ID NO.: 88  GCTGTCGAAGCGCACGTA
```

Figure 9:
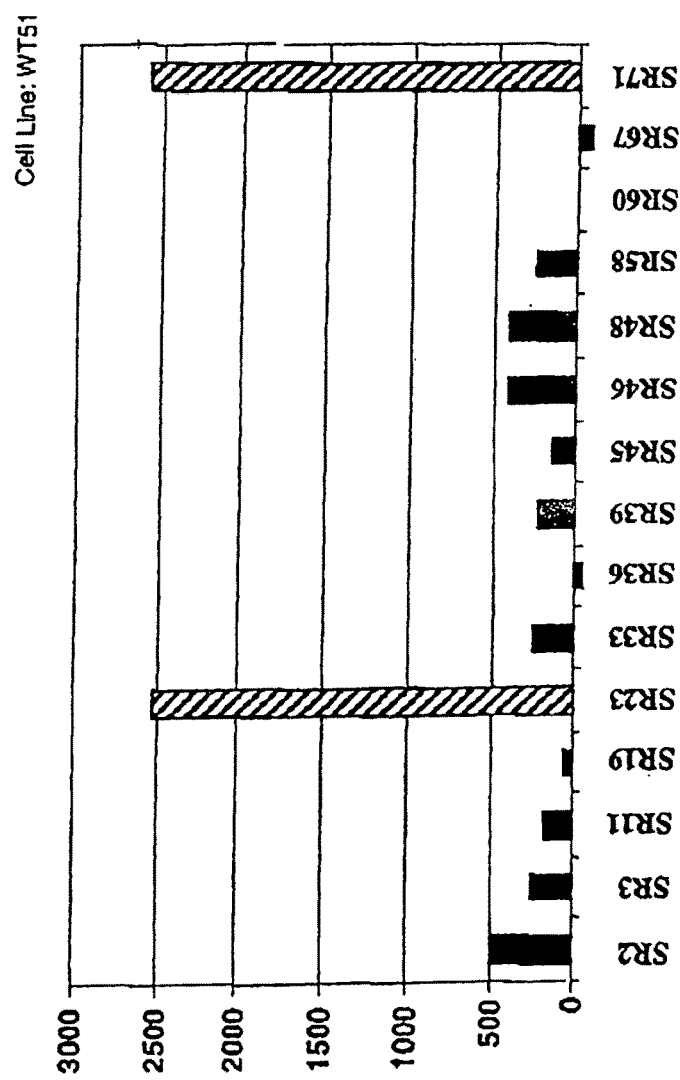
FIG. 9 shows results obtained from eMAP primer extension for DR locus.
Figure 10:
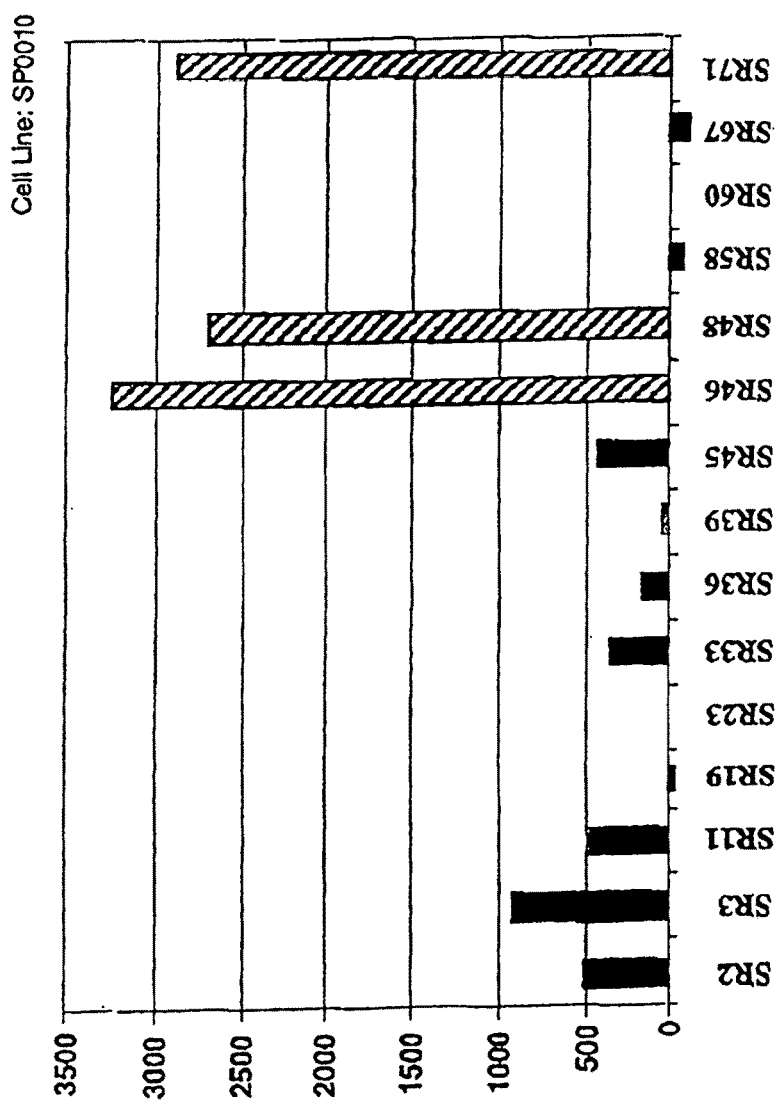
FIG. 10 shows results obtained from eMAP for DR locus.

Reaction conditions were as described in Example 7 except that the annealing temperature was 55° C. instead of 40° C., and the extension temperature was 70° C. instead of 60° C. Double-stranded DNA was used as in Example 7. Single-stranded DNA generated better results under current conditions. Single-stranded DNA was generated by re-amplifying the initial PCR product in the same PCR program with only one of the probes. Results for two cell lines, W51 and SP0010, are shown in FIG. 9 and FIG. 10. NEG, a negative control, was coupled to a selected type of bead. Signal intensity for other probes minus NEG was considered to be real signal for the probe and the values were plotted in the figures. The Y axis unit was the signal unit from the camera used in the experiment. The distinction between the positive and negative probes was unambiguous for each sample. In particular, and in contrast to the situation typically encountered in SSO analysis, it was not necessary to make comparisons to other samples to determine a reliable threshold for each probe.

The probes used for HLA-A were:

```
SAD   SEQ. ID NO.: 89  CACTCCACGCACGTGCCA
SAF   SEQ. ID NO.: 90  GCGCAGGTCCTCGTTCAA
SAQ   SEQ. ID NO.: 91  CTCCAGGTAGGCTCTCAA
SAR   SEQ. ID NO.: 92  CTCCAGGTAGGCTCTCTG
SAX   SEQ. ID NO.: 93  GCCCGTCCACGCACCG
```

```
SAZ      SEQ. ID NO.: 94    GGTATCTGCGGAGCCCG

SAAP     SEQ. ID NO.: 95    CATCCAGGTAGGCTCTCAA

SA8      SEQ. ID NO.: 96    GCCGGAGTATTGGGACGA

SA13     SEQ. ID NO.: 97    TGGATAGAGCAGGAGGGT

SA16     SEQ. ID NO.: 98    GACCAGGAGACACGGAATA
```

Figure 11:
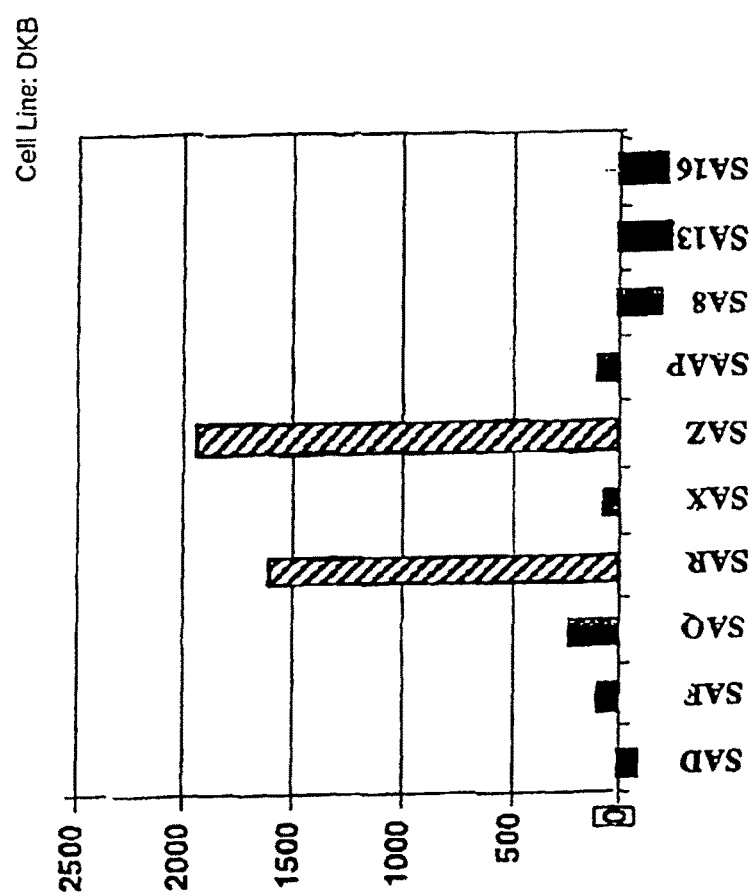
FIG. 11 shows results obtained from eMAP for A locus Exon 3.
Figure 12:
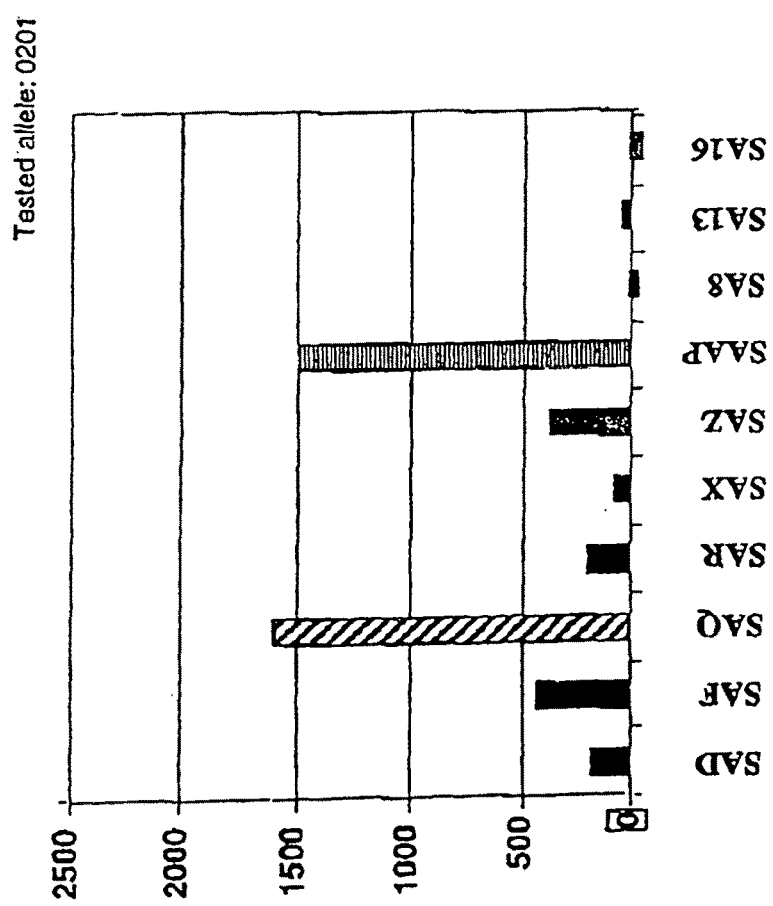
FIG. 12 shows results obtained from eMAP SSP for A locus Exon 3 and is an example of tolerance for the non-designated polymorphism.

Results for A locus exon 3, shown in FIG. 11 and FIG. 12, also were unambiguous. FIG. 12 also shows an example of the mismatch tolerance for a non-designated polymorphism. That is, while allele 0201, displaying C instead of A at position M−18, is not perfectly matched to probe SAAP, the elongation reaction nonetheless proceeded because the polymerase detected a perfect match for the designated polymorphism at the probe's 3' end and tolerated the mismatch at position M−18.

The probes used for HLA-B were:

```
SB220    SEQ. ID NO.: 99     CCGCGCGCTCCAGCGTG

SB246    SEQ. ID NO.: 100    CCACTCCATGAGGTATTTCC

SB229    SEQ. ID NO.: 101    CTCCAACTTGCGCTGGGA

SB272    SEQ. ID NO.: 102    CGCCACGAGTCCGAGGAA

SB285    SEQ. ID NO.: 103    GTCGTAGGCGTCCTGGTC

SB221    SEQ. ID NO.: 104    TACCAGCGCGCTCCAGCT

SB197    SEQ. ID NO.: 105    AGCAGGAGGGGCCGGAA

SB127    SEQ. ID NO.: 106    CGTCGCAGCCATACATCCA

SB187    SEQ. ID NO.: 107    GCGCCGTGGATAGAGCAA

SB188    SEQ. ID NO.: 108    GCCGCGAGTCCGAGGAC

SB195    SEQ. ID NO.: 109    GACCGGAACACACAGATCTT
```

Experiments using these probes for typing HLA-B exon 2 were performed using reference cell lines. As with HLA-A, unambiguous results (not shown here) were obtained.

Example 10: CF Mutation Analysis—Probe and Array Design for Probe Elongation

This Example describes the design and application of a planar array of probes, displayed on color-encoded particles, these probes designed to display several—most frequently two selected base compositions at or near their respective 3' ends and designed to align with designated regions of interest within the CFTR target gene.

The CFTR gene sequence from Genebank (found at the website having server name ncbi.nlm.nih with domain name .gov) was used to design sixteen-mer probes for the multiplexed analysis of the 25 CFTR mutations in the ACMG-CF mutation panel. Probe sequences were designed using PROBE 3.0 (see website having server name genome.wi.mit with domain name .edu) and aligned with respective exon sequences (at website having server name searchlauncher.bcm.tmc with domain name .edu, and resource ID seq-search/alignment.html). Oligonucleotides were designed to comprise 15 to 21 nucleotides, with a 30-50% G+C rich base composition and synthesized to contain a 5' biotin TEG (Synthegen TX); to handle small deletions, the variable sequence of the TEI region was placed at or within 3-5 positions of the probe's 3' terminus. Probe compositions are listed in the table below.

A combination of 17 either pure blue or blue-green stained beads were used with CF mutation analysis. The 48 base long Human B-actin gene (Accession #X00351) was synthesized and used in each reaction as an internal positive control. Sixteen base long complementary probes were included on each array. The CFTR gene sequence from Genebank (at website having server name ncbi.nlm.nih with domain name .gov) was used for probe design for analysis of 25 CFTR mutations in the ACMG-CF mutation panel. The probe sequence was aligned with respective exon sequences (see website having server name searchlauncher.bcm.tmc with domain name.edu, and resource ID seq-search/alignment.html-Oligonucleotides were synthesized with a 5' biotin TEG (Synthegen TX) and coupled on the surface of beads in presence of 0.5 M NaCl. Beads were immobilized on the surface of a chip by LEAPS.

```
                      EXON MUTATIONS
                         SEQUENCE

3    G85E              SEQ. ID NO.: 110 CCC CTA AAT ATA AAA AGA TTC
         G85E-X            SEQ. ID NO.: 111 CCC CTA AAT ATA AAA AGA TTT 4    1148              SEQ. ID NO.: 112 ATT CTC ATC TCC ATT CCA A
         1148-X            SEQ. ID NO.: 113 ATT CTC ATC TCC ATT CCA G
         621 + 1G > T      SEQ. ID NO.: 114 TGT GTG CAA GGA AGT ATT AC
         621 + 1G > T-X    SEQ. ID NO.: 115 TGT GTG CAA GGA AGT ATT AA
         R117H             SEQ. ID NO.: 116 TAG ATA AAT CGC GAT AGA GC
         R117H-X           SEQ. ID NO.: 117 TAG ATA AAT CGC GAT AGA GT 5    711 + 1G > T      SEQ. ID NO.: 118 TAA ATC AAT AGG TAC ATA C
                           SEQ. ID NO.: 119 TAA ATC AAT AGG TAC ATA A

7    R334W             SEQ. ID NO.: 120 ATG GTG GTG AAT ATT TTC CG
         R334W-X           SEQ. ID NO.: 121 ATG GTG GTG AAT ATT TTC CA
         R347P             SEQ. ID NO.: 122 ATT GCC GAG TGA CCG CCA TGC
         R347P-X           SEQ. ID NO.: 123 ATT GCC GAG TGA CCG CCA TGG
         1078delT          SEQ. ID NO.: 124 CAC AGA TAA AAA CAC CAC AAA
         1078delT-X        SEQ. ID NO.: 125 CAC AGA TAA AAA CAC CAC AA
         1078delT-X-2      SEQ. ID NO.: 126 CAC AGA TAA AAA CAC CAC A 9    A455E             SEQ. ID NO.: 127 TCC AGT GGA TCC AGC AAC CG
         A455E-X           SEQ. ID NO.: 138 TCC AGT GGA TCC AGC AAC CT
```

-continued

| EXON | MUTATIONS | SEQUENCE |
|---|---|---|
| 10 | 508 | SEQ. ID NO.: 129 CAT AGG AAA CAC CAA AGA T |
|  | 1507 | SEQ. ID NO.: 130 CAT AGG AAA CAC CAA A |
|  | F508 | SEQ. ID NO.: 131 CAT AGG AAA CAC CAA T |
| 11 | 1717-1G > A | SEQ. ID NO.: 132 CTG CAA ACT TGG AGA TGT CC |
|  | 1717-1G > A | SEQ. ID NO.: 133 CTG CAA ACT TGG AGA TGT CT |
|  | 551D | SEQ. ID NO.: 134 TTC TTG CTC GTT GAC |
|  | 551D-X | SEQ. ID NO.: 135 TTC TTG CTC GTT GAT |
|  | R553 | SEQ. ID NO.: 136 TAAAGAAATTCTTGCTCG |
|  | R553X | SEQ. ID NO.: 137 TAAAGAAATTCTTGCTCA |
|  | R560 | SEQ. ID NO.: 138 ACCAATAATTAGTTATTCACC |
|  | R560X | SEQ. ID NO.: 139 ACCAATAATTAGTTATTCACG |
|  | G542 | SEQ. ID NO.: 140 GTGTGATTCCACCTTCTC C |
|  | G542X | SEQ. ID NO.: 141 GTGTGATTCCACCTTCTC A |
| INT-12 | 1898 | SEQ. ID NO.: 142 AGG TAT TCA AAG AAC ATA C |
|  | 1898-X | SEQ. ID NO.: 143 AGG TAT TCA AAG AAC ATA T |
| 13 | 2183deLA | SEQ. ID NO.: 144 TGT CTG TTT AAA AGA TTG T |
|  | 2183deLA-X | SEQ. ID NO.: 145 TGT CTG TTT AAA AGA TTG C |
| INT 14B | 2789 | SEQ. ID NO.: 146 CAA TAG GAC ATG GAA TAC |
|  | 2789-X | SEQ. ID NO.: 147 CAA TAG GAC ATG GAA TAC T |
| INT 16 | 3120 | SEQ. ID NO.: 148 ACT TAT TTT TAC ATA C |
|  | 3120-X | SEQ. ID NO.: 149 ACT TAT TTT TAC ATA T |
| 18 | D1152 | SEQ. ID NO.: 150 ACT TAC CAA GCT ATC CAC ATC |
|  | D1152 | SEQ. ID NO.: 151 ACT TAC CAA GCT ATC CAC ATG |
| INT 19 | 3849 + 10kbC > T-WT1 | SEQ. ID NO.: 152 CCT TTC Agg GTG TCT TAC TCG |
|  | 3849 + 10kbC > T-M1 | SEQ. ID NO.: 153 CCT TTC Agg GTG TCT TAC TCA |
| 19 | R1162 | SEQ. ID NO.: 154 AAT GAA CTT AAA GAC TCG |
|  | R1162-X | SEQ. ID NO.: 155 AAT GAA CTT AAA GAC TCA |
|  | 3659delC-WT1 | SEQ. ID NO.: 156 GTA TGG TTT GGT TGA CTT GG |
|  | 3659delCX-M1 | SEQ. ID NO.: 157 GTA TGG TTT GGT TGA CTT GTA |
|  | 3659delC-WT2 | SEQ. ID NO.: 158 GTA TGG TTT GGT TGA CTT GGT A |
|  | 3659delCX-M2 | SEQ. ID NO.: 159 GTA TGG TTT GGT TGA CTT GT A |
| 20 | W1282 | SEQ. ID NO.: 160 ACTCCA AAG GCT TTC CTC |
|  | W1282-X | SEQ. ID NO.: 161 CT CCA AAG GCT TTC CTT |
| 21 | N1303K | SEQ. ID NO.: 162 TGT TCA TAG GGA TCC AAG |
|  | N1303K-X | SEQ. ID NO.: 163 TGT TCA TAG GGA TCC AAC |
| b | β Actin | SEQ. ID NO.: 164 AGG ACT CCA TGC CCA G |

Probes were attached, in the presence of 0.5 M NaC 1, to differentially encoded beads, stained either pure blue or blue-green Beads were immobilized on the surface of a chip using LEAPS. A synthetic 48 base Human 13-actin gene (Accession #X00351) was included in each reaction as an internal positive control.

Array Design—

In a preferred embodiment, the 25 CF mutations were divided into four different groups so as to minimize sequence homologies between members of each group. That is, mutations were sorted into separate groups so as to minimize overlap between probe sequences in any such group and thereby to minimize cross-hybridization under conditions of multiplexed analysis. Each group, displayed on color-encoded beads, was assembled into a separate array. (Results for this 4-chip array design are described in the following Example). Alternative robust array designs also are disclosed herein.

Example 11: Multiplexed CF Mutation Analysis by Probe Elongation Using READ

Genomic DNA, extracted from several patients, was amplified with corresponding probes in a multiplex PCR (mPCR) reaction using the method described in L. McCurdy, Thesis, Mount Sinai School of Medicine, 2000, which is incorporated by reference. This mPCR reaction uses chimeric primers tagged with a universal sequence at the 5' end. Antisense primers were phosphorylated at the 5' end (Synthegen, TX). Twenty eight amplification cycles were performed using a Perkin Elmer 9600 thermal cycler, each cycle comprising a 10 second denaturation step at 94° C. with a 48 second ramp, a 10 second annealing step at 60° C. with a 36 second ramp and a 40 second extension step at 72° C. with a 38 second ramp, each reaction (50 µl) containing 500 ng genomic DNA, 1×PCR buffer (10 mM Tris HCL, 50 mM KCL, 0.1% Triton X-100), 1.5 mM $MgCl_2$, 200 µM each of PCR grade dNTPs and 5 units Taq DNA polymerase. Optimal probe concentrations were determined for each probe pair. Following amplification, products were purified to remove all reagents using a commercially available kit (Qiagen). DNA concentration was determined by spectrophotometric analysis.

PCR products were amplified with antisense 5'-phosphorylated primers. To produce single-stranded DNA templates, PCR reaction products were incubated with 2.5 units of exonuclease in 1× buffer at 37° C. for 20 min, followed by enzyme inactivation by heating to 75° C. for 10 min. Under these conditions, the enzyme digests one strand of duplex DNA from the 5'-phosphorylated end and releases 5'-phosphomononucleotides (J. W. Little, et al., 1967). Single-stranded targets also can be produced by other methods known in the art.

Figure 15:
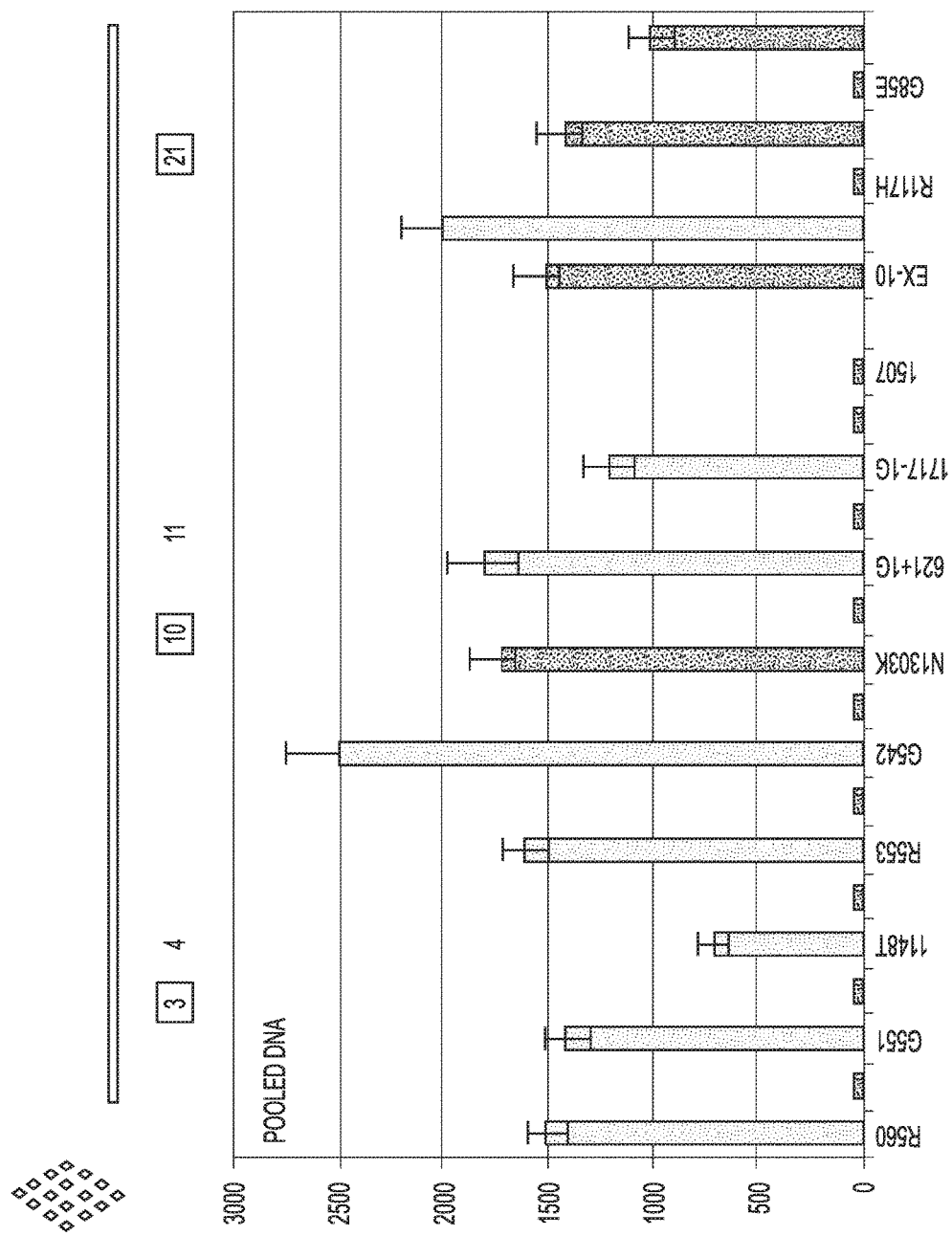
FIG. 15 is an illustration of elongation of multiple probes using combined PCR products.

Single or pooled PCR products (20 ng each) were added to an annealing mixture containing 10 mM Tris-HCL (pH 7.4) 1 mM EDTA, 0.2 M NaCl, 0.1% Triton X-100. The annealing mixture was placed in contact with the encoded array of bead-displayed CF probes (of Example 10) and incubated at 37-55° C. for 20 minutes. The extension mixture—containing 3 U of Thermo Sequenase (Amersham Pharmacia Biotech NJ), 1× enzyme buffer with either Fluorescein-labeled or TAMRA-labeled deoxynucleotide (dNTP) analogs (NEN Life Sciences) and 1 µmole of each type of unlabeled dNTP—was then added, and the elongation reaction was allowed to proceed for 3 minutes at 60° C. The bead array was washed with deionized, sterilized water (dsH$_2$O) for 5-15 minutes. An image containing the fluorescence signal from each bead within the array was recorded using a fluorescence microscope equipped with a CCD camera. Images were analyzed to determine the identity of each of the elongated probes. The results are shown in FIG. 15.

Example 12: Use of Covering Probes

Several SNPs have been identified within exon 10 of the CFTR gene. The polymorphisms in exon 10 are listed at the end of this Example. The following nine SNPs have been identified in the sequence of Δ508, the most common mutation in the CFTR gene (see website having server name snp.csh1 with domain name .org):

dbSNP213450 A/G
dbSNP180001 C/T
dbSNP1800093 G/T
1648 A/G
dbSNP100092 C/G
dbSNP1801178 A/G
dbSNP1800094 A/G
dbSNP1800095 G/A

Probes are designed to accommodate all possible SNPs are synthesized and coupled to color-encoded beads. The primers for target amplification (described in Example 11) are also modified to take into account all possible SNPs. The PCR-amplified target mediates the elongation of terminally matched probes. The information collected from the analysis is twofold: identification of mutations and SNPs.

Exon 10 Polymorphisms

```
                                                            SEQ. ID NO.: 165
      1 cactgtagct gtactacctt ccatctcctc aacctattcc aactatctga atcatgtgcc 61 cttctctgtg aacctctatc ataatacttg tcacactgta ttgtaattgt ctcttttact 121 ttccccttgta tcttttgtgc atagcagagt acctgaaaca ggaagtattt taaatatttt 181 gaatcaaatg agttaataga atctttacaa ataagaatat acacttctgc ttaggatgat 241 aattggaggc aagtgaatcc tgagcgtgat ttgataatga cctaataatg atgggtttta 301 tttccagact tcaCttctaa tgAtgattat gggagaactg gagccttcag agggtaaaat 361 taagcacagt ggaagaattt cattctgttc tcagttttcc tggattatgc ctggcaccat 421 taaagaaaat AtCAtctTtg gtgtttccta tgatgaatat agatacagaa gcgtcatcaa 481 agcatgccaa ctagaAgagG taagaaacta tgtgaaaact ttttgattat gcatatgaac 541 ccttcacact acccaaatta tatatttggc tccatattca atcggttagt ctacatatat 601 ttatgtttcc tctatgggta agctactgtg aatggatcaa ttaataaaac acatgaccta 661 tgctttaaga agcttgcaaa cacatgaaat aaatgcaatt tattttttaa ataatgggtt 721 catttgatca caataaaatgc attttatgaa atggtgagaa ttttgttcac tcattagtga 781 gacaaacgtc tcaatggtta tttatatggc atgcatatag tgatatgtgg t
```

Example 13: CF Mutation Analysis—On-Bead Probe Elongation with Model System

Figure 13:
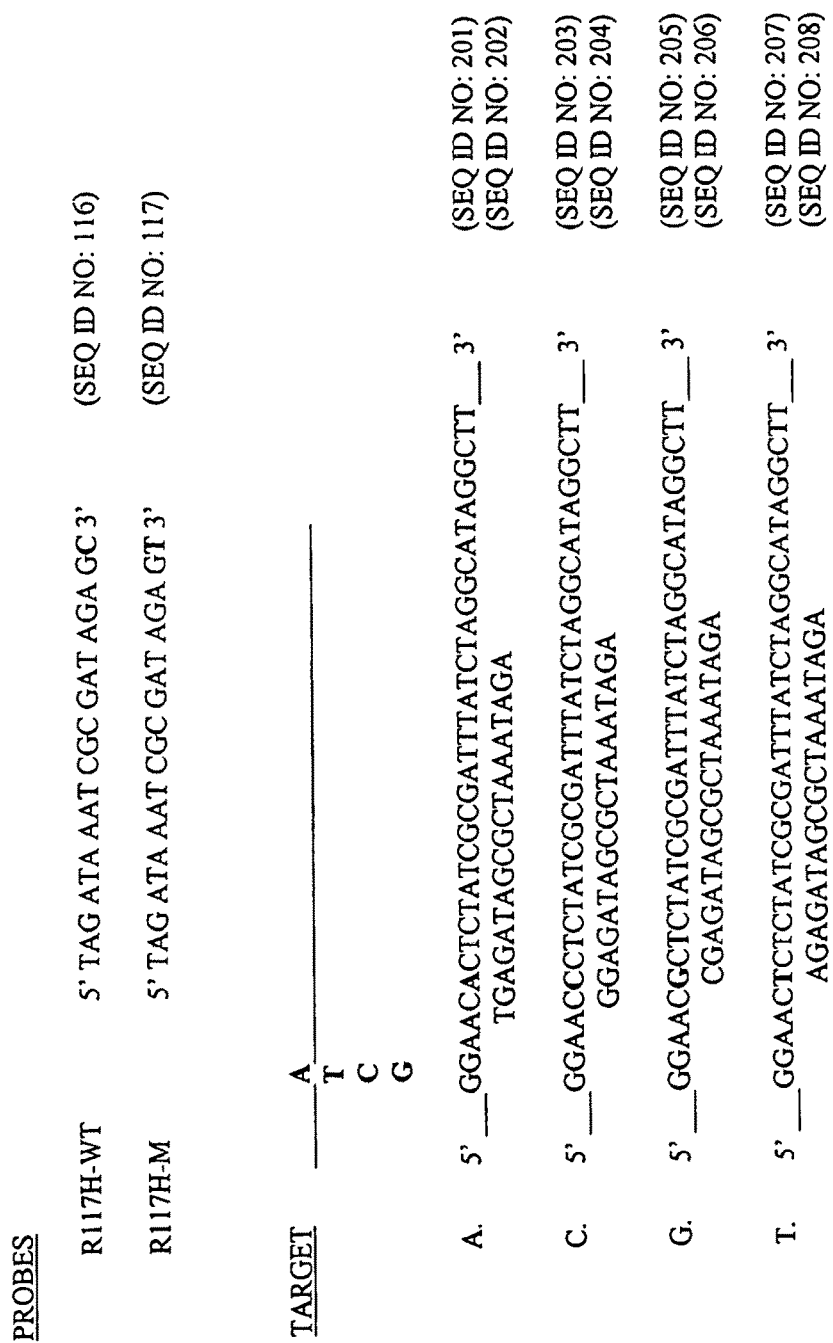
FIG. 13 is an illustration of bead immobilized probe elongation of variable mutant sites.

FIG. 13 provides an overview of detection of CF gene mutation R117H. The target was amplified by PCR as described in Example 11. Two 17-base probes variable at their 3' ends were immobilized on color coded beads. The target nucleic acid sequence was added along with TAMRA-labeled dCTP, unlabeled dNTPs and thermostable DNA polymerase.

Complementary 17-mer oligonucleotide probes variable at the 3' end were synthesized by a commercial vendor (Synthegen TX) to contain 5' biotin attached by way of a 12-C spacer (Biotin-TEG) and were purified by reverse phase HPLC. Probes were immobilized on color encoded beads. Probes were attached to color-encoded beads. A synthetic 48-mer oligonucleotide also was provided to contain either A,T,C or G at a designated variable site, corresponding to a cystic fibrosis gene mutation at exon 4 (R117H).

Figure 16A:
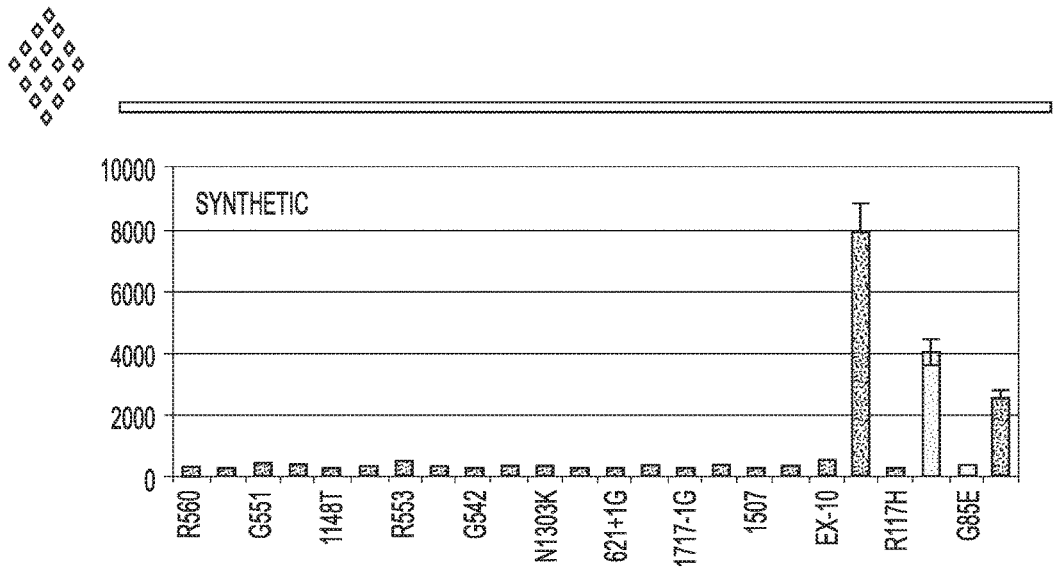
FIG. 16a is an illustration of probe elongation using a synthetic target.

1 µM of synthetic target was added to an annealing mixture containing 10 mM Tris-HCL (pH 7.4) 1 mM EDTA, 0.2 M NaCl, 0.1% Triton X-100. The annealing mixture was placed in contact with the encoded bead array and incubated at 37° C. for 20 minutes. An elongation mixture containing 3 U of Thermo Sequenase (Amersham Pharmacia Biotech NJ), 1× enzyme buffer with TAMRA-labeled deoxynucleotide (dNTP) analogs (NEN Life Sciences) and 1 µM of each type of unlabeled dNTP was then added, and the elongation reaction was allowed to proceed for 3 minutes at 60° C. The bead array was then washed with dsH$_2$O for 5-15 minutes and an image containing the fluorescence signal from each bead within the array was recorded using a fluorescence microscope equipped with a CCD camera. Images were analyzed to determine the identity of each of the elongated probes. The signal was analyzed by capturing the image by a CCD camera and comparing signal intensity between two probes that can be decoded by the bead color. The wild-type probe exactly matched the added target and therefore yielded an elongation product, whereas no elongation was observed for the mutant probe. The results are shown in FIG. 16a.

Figure 14:
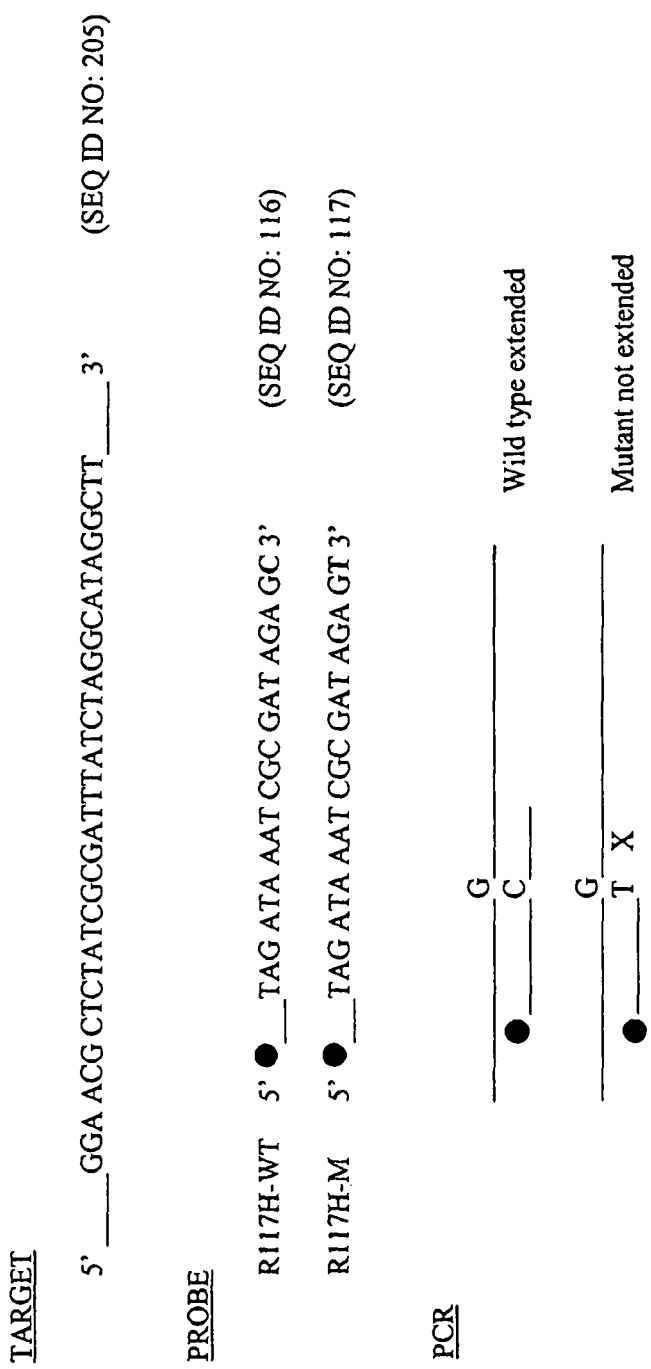
FIG. 14 is an illustration of PCR using primers immobilized on the surface of beads.
Figure 16B:
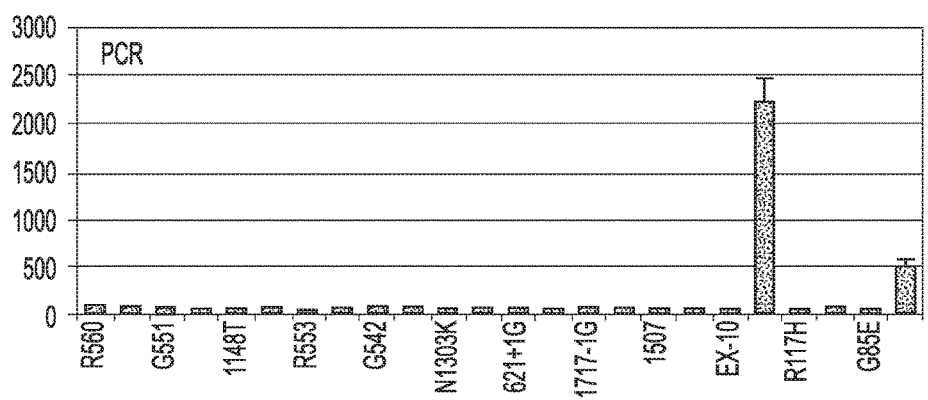
FIG. 16b is an illustration of probe elongation using beads in a PCR reaction.

Example 14: CF Mutation Analysis—PCR with Bead-Tagged Primers and Integrated Detection This example illustrates probe elongation on the surface of beads in suspension, followed by assembly of and immobilization of beads on the surface of a chip for image analysis. Oligonucleotides corresponding to CFTR gene mutation R117H were designed with variable 3' ends (FIG. 14) and were synthesized to contain a 5' biotin-TEG with a 12 C spacer (Synthegen, Texas). The probes were attached to blue stained beads as follows: 2 µM of probe were added to a bead solution in 1×TE (100 mM Tris-HCl, 10 mM EDTA), 500 mM NaCl and reacted for 45 mM at room temperature. Beads were washed with 1×TE, 150 mM of NaCl for 3×, and suspended in 50 µl of the same solution. One µl of each type of bead was added to PCR mix containing 1× buffer (100 mM Tris-HCl, pH. 9.0, 1.5 mM MgCl$_2$ 500 mM KCl), 40 µM Cy5-labeled dCTP (Amersham Pharmacia Biotech NJ), and 80 µM of the other three types of dNTPs, and 3 U of Taq DNA polymerase (Amersham Pharmacia Biotech NJ). Wild type complementary target (40 ng) was added to the PCR mix just before amplification. Eleven cycles of PCR amplification were performed in a Perkin Elmer 9600 thermal cycler, each cycle consisting of denaturation for 30 s at 90° C., annealing for 30 s at 55° C., and elongation at 72° C. for 20 s After amplification, beads were washed four times by centrifugation in 1×TE buffer. and placed on the chip surface. Images were recorded as in previous Examples and analyzed using the software described in WO 01/98765. The results show specific amplification for beads coupled with the wild-type probe, but no amplification for beads coupled with the mutant probe. The results are shown in FIG. 16b.

This example demonstrates the integration of multiplexed PCR using bead-tagged probes with subsequent assembly of beads on planar surfaces for instant imaging analysis. In a preferred embodiment, a microfluidically connected multicompartment device may be used for template amplification as described here. For example, a plurality of compartments capable of permitting temperature cycling and housing, in each compartment, one mPCR reaction producing a subset of all desired amplicons may be used as follows: (1) perform PCR with different probe pairs in each of four compartments, using encoded bead-tagged primers as described in this Example; (2) following completion of all PCR reactions, pool the amplicon-displaying beads; (3) assemble random array; and (4) record image and analyze the data.

Array assembly may be accomplished by one of several methods of the prior art including LEAPS.

Figure 17:
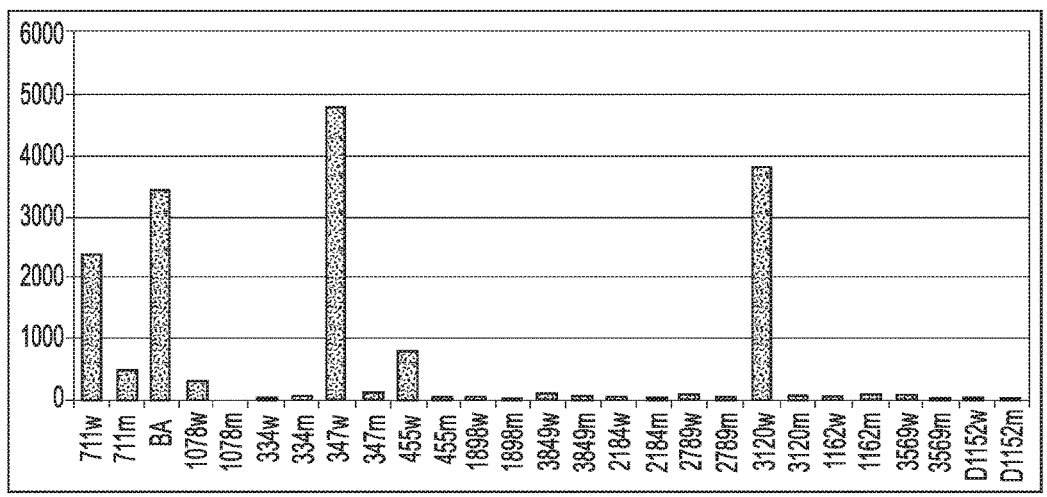
FIG. 17 is an illustration of one-step elongation with temperature-controlled cycling results.

Example 15: CF Mutation Analysis—One-Step Annealing and Elongation in Temperature-Controlled Reactor Genomic DNA, extracted from several patients, was amplified with corresponding primers in a multiplexed PCR (mPCR) reaction, as described in Example 11. Following amplification, products were purified to remove all reagents using a commercially available kit (Qiagen). DNA concentration was determined by spectrophotometric analysis. Single or pooled PCR products (20 ng each) were added to an annealing mixture containing 10 mM Tris-HCL (pH 7.4) 1 mM EDTA, 0.2 M NaCl, 0.1% Triton X-100. The annealing mixture was mixed with elongation mixture containing 3 U of Thermo Sequenase (Amersham Pharmacia Biotech, NJ), 1× enzyme buffer with either fluorescein-labeled or TAMRA-labeled deoxynucleotide (dNTP) analogs (NEN Life Sciences) and 1-10 µmole of each type of unlabeled dNTP and placed in contact with an array of oligonucleotide probes displayed on a color-encoded array. Oligonucleotides were designed and synthesized as in previous Examples. The annealing- and elongation reactions were allowed to proceed in a temperature controlled cycler. The temperature steps were as follows: three minutes each at 65° C., 60° C., 55° C., 50° C. and 45° C., with a ramp between temperatures of less than 30 seconds. The bead array was then washed with dsH$_2$O for 5 to 15 min. and an image containing the fluorescence signal from each bead within the array was recorded using a fluorescence microscope equipped with a CCD camera. Images were analyzed to determine the identity of each of the elongated probes. Typical results are shown in FIG. 17.

Example 16: Pooling of Covering Probes

To analyze designated polymorphisms, 20-mer oligonucleotide elongation probes of 30-50% G+C base composition were designed to contain a variable site (G/T) at the 3'end, to be aligned with the designated polymorphic site. Two non-designated polymorphic sites were anticipated at position 10 (C/A) and at 15 (T/G). A summary of the design follows:
  Wild-Type Probe Sequence:
  Oligo 1: "G" at position 20, "C" at 10, and "T" at 15.
  Oligo 2: "G" at position 20, "C" at 10, and "G" at 15.
  Oligo 3: "G" at position 20, "A" at 10, and "T" at 15.
  Oligo 4: "G" at position 20, "A" at 10, and "G" at 15.
  Mutant Probe Sequence:
  Oligo 1: "T" at position 20, "C" at 10, and "T" at 15.
  Oligo 2: "T" at position 20, "C" at 10, and "G" at 15.
  Oligo 3: "T" at position 20, "A" at 10, and "T" at 15.
  Oligo 4: "T" at position 20, "A" at 10, and "G" at 15.
  All of the probes were pooled and attached to a single type of color-coded bead using protocols of previous Examples. When single-stranded target is added to these beads displaying pooled probes, one of the probes will yield elongation product as long as it is perfectly aligned with the designated polymorphism.

Example 17: Designated Polymorphisms in Heterozygous and Homozygous Configurations To distinguish between heterozygous and homozygous configurations, the design of the previous Example is augmented to contain a second set of probes to permit the identification of the C/A designated polymorphism aligned with the probes' 3'ends, and to permit calling of heterozygous versus homozygous mutations.

As in the previous example, two non-designated polymorphic sites are anticipated at positions 10 (C/A) and 15 (T/G). A summary of the design follows:

Set #1:
Oligo 1: "C" at position 20, "C" at 10, and "T" at 15.
Oligo 2: "C" at position 20, "C" at 10, and "G" at 15.
Oligo 3: "C" at position 20, "A" at 10, and "T" at 15.
Oligo 4: "C" at position 20, "A" at 10, and "G" at 15.

Set #2:
Oligo 5: "A" at position 20, "C" at 10, and "T" at 15.
Oligo 6: "A" at position 20, "C" at 10, and "G" at 15.
Oligo 7: "A" at position 20, "A" at 10, and "T" at 15.
Oligo 8: "A" at position 20, "A" at 10, and "G" at 15.

Oligonucleotides from set #1 are pooled and attached to a single type of color (e.g. green) coded bead using protocols of previous Examples. Oligonucleotides from set #2 were pooled and attached to a second type of color (e.g. orange) coded bead using protocols of previous Examples. Beads were pooled and immobilized on the surface of chip as described earlier. Next, target was introduced, and on-chip reactions performed as described in previous Examples. If probes on green beads only are elongated, the individual has a normal (or wild-type) allele. If probes on orange beads only are elongated, the individual is homozygous for the mutation. If probes on green as well as origan beads are elongated, the individual is heterozygous for that allele. This design is useful for the identification of known and unknown mutations.

Example 18: Confirmatory Sequencing ("Resequencing")

The design of the present invention can be used for re-sequencing of a specific area. This test can be used when on-chip probe elongation reaction requires confirmation, as in the case of reflex tests for 1506V, 1507V, F508C and 7T in the CF mutation panel. The sequence in question, here 20 bases to 30 bases in length, is sequenced on-chip by multiplexed interrogation of all variable sites. This is accomplished by designing specific probes for ambiguous locations, and by probe-pooling as described in Examples 16 and 17.

Example 19: Elongation with One Labeled dNTP and Three Unlabeled dNTPs

Figure 18:
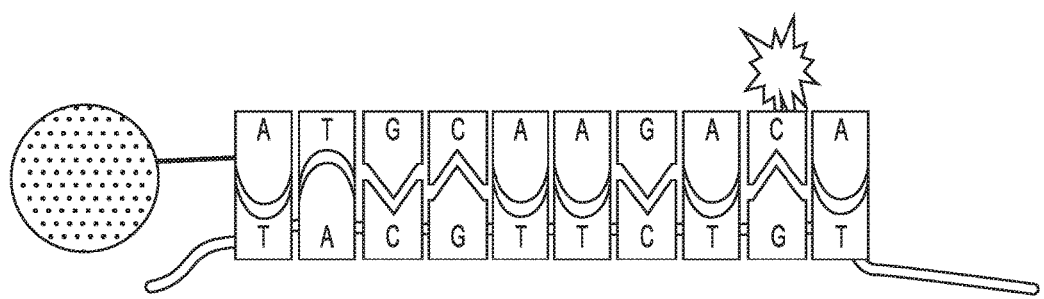
FIG. 18 is an illustration of primer elongation with labeled dNTP and three other unlabeled dNTPs.

By way of incorporating at least one labeled dNTP, all elongation products are detected in real-time and identified by their association with coded solid phase carriers. Using assay conditions described in connection with Examples 6 and 7, tetramethylrhodamine-6-dCTP and unlabeled dATP, dTTP and dGTP were provided in an elongation reaction to produce a fluorescently labeled elongation product as illustrated FIG. 18. Other dye labeling of dNTPs (as in BODIPY-labeled dUTP and Cy5-labeled dUTP) may be used. Similarly, any other labeled dNTP can be used. The length of the elongation product depends on the amount of labeled dNTP tolerated by the DNA polymerase. Available enzymes generally exhibit a higher tolerance for strand-modifying moieties such as biotin and digoxigenin which may then be reacted in a second step with labeled avidins or antibodies to accomplish indirect labeling of elongation products. When using these small molecules, elongation products measuring several hundred bases in length are produced.

Example 20: Extension with One Labeled ddNTP, Three Unlabeled dNTPs

Figure 19:
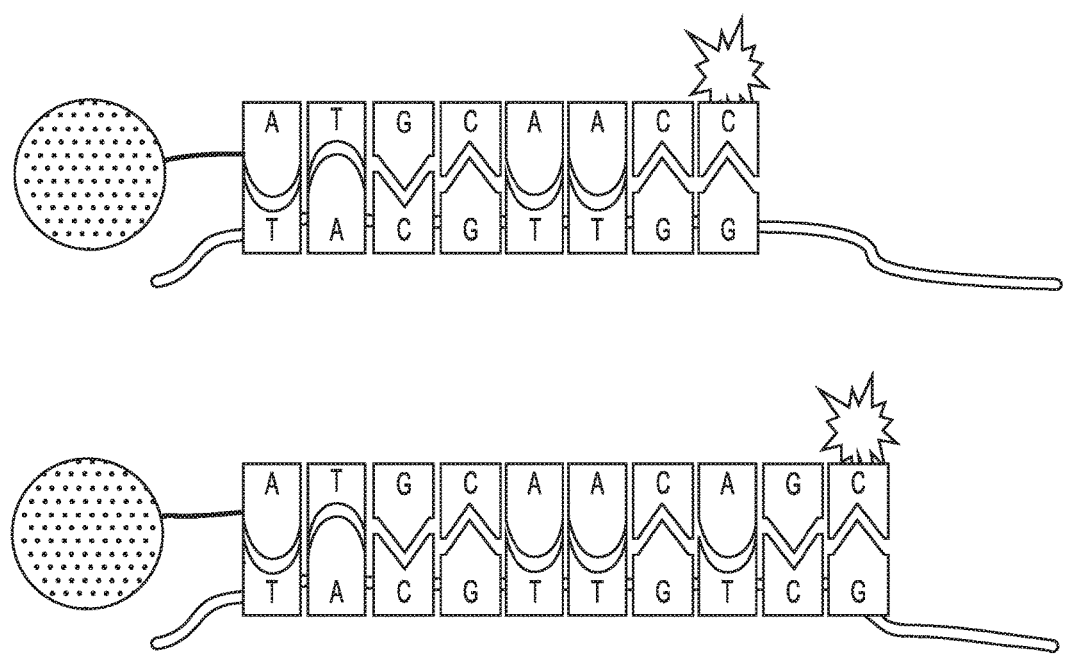
FIG. 19 is an illustration of primer elongation with labeled ddNTP and three other unlabeled dNTPs.

TAMRA-labeled ddCTP may be incorporated to terminate the extension reaction, as illustrated in FIG. 19. On-chip reactions using TAMRA-labeled ddCTP were performed as described in Examples 6 and 7. In a reaction mixture containing TAMRA-ddCTP and unlabeled dTTP, dATP and dGTP, following annealing of the target to the matching probe, the extension reaction terminates when it completes the incorporation of the first ddCTP. This may occur with the very first base incorporated, producing a single base extension product, or it may occur after a number of unlabeled dNTPs have been incorporated.

Figure 20:
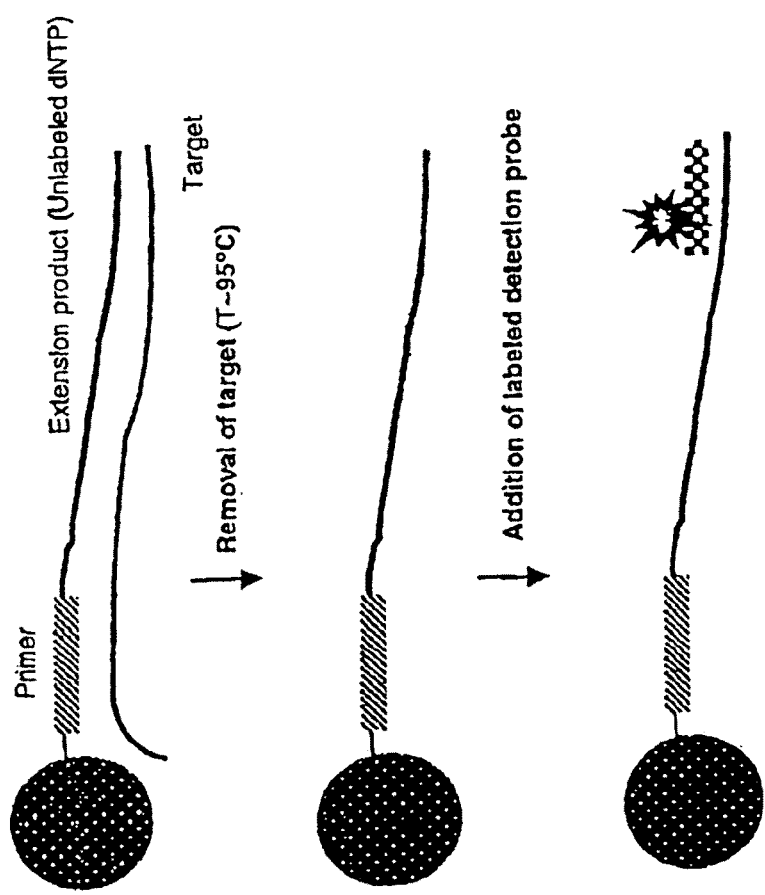
FIG. 20 is an illustration of primer elongation, where four unlabeled dNTPs are used for elongation and the product is detected by a labeled oligonucleotide probe which hybridizes to the extended unlabeled product.

Example 21: Elongation with Four Unlabeled dNTPs, Detection by Hybridization of Labeled Probe Probes are elongated using a full set of four types of unlabeled dNTPs, producing, under these "native" conditions for the polymerase, elongation products measuring several hundred bases in length, limited only by the length of the annealed template and on-chip reaction conditions. The elongation product is detected, following denaturation at high temperature, in a second step by hybridization with a labeled oligonucleotide probe whose sequence is designed to be complementary to a portion of the elongation product. This process is illustrated in FIG. 20.

Figure 21:
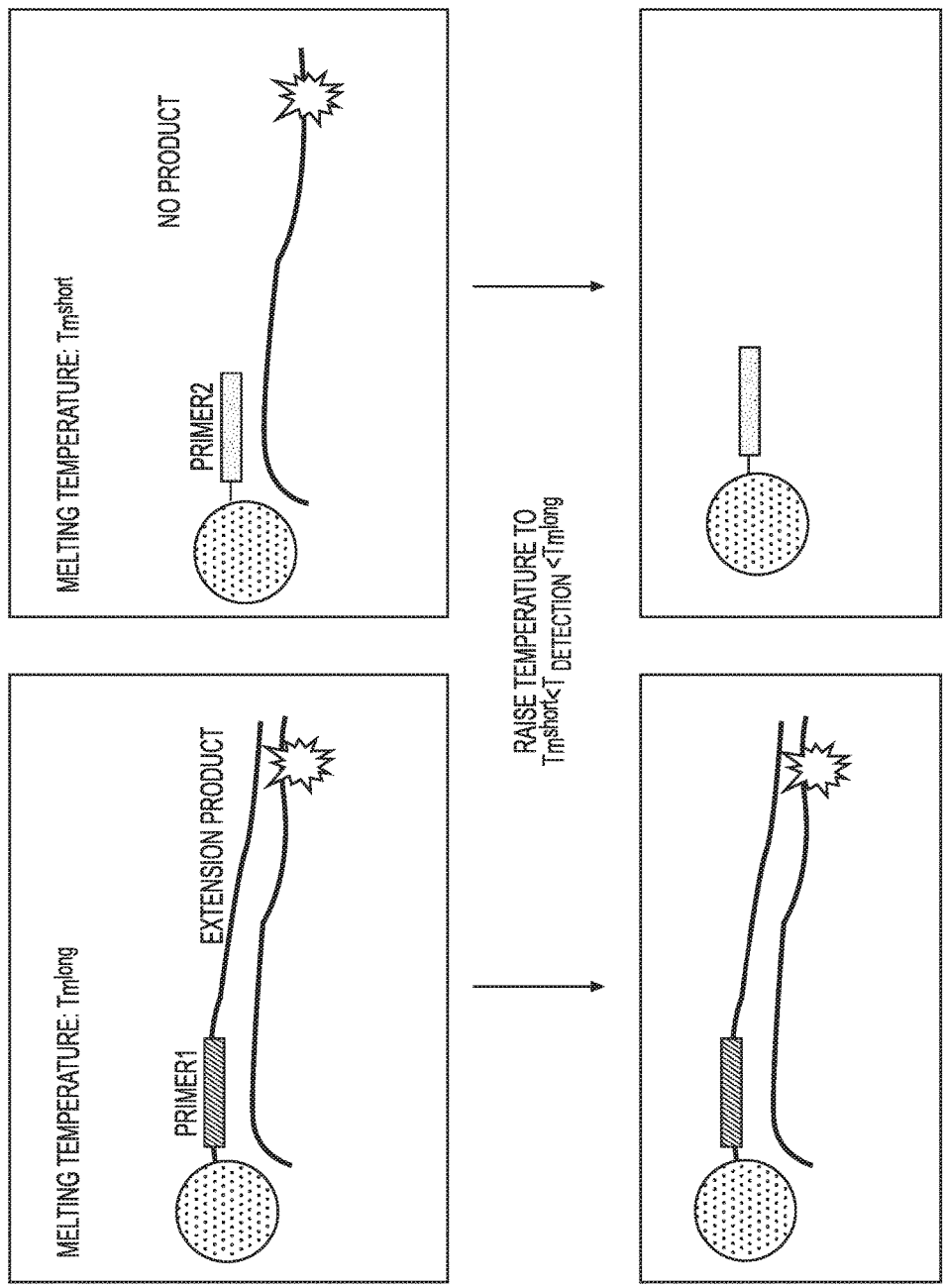
FIG. 21 is an illustration of a primer extension in which a labeled target and four unlabeled dNTPs are added. This illustration which shows that only with the extended product can the labeled target be retained with the beads when high temperature is applied to the chip.

Example 22: Elongation with Four Unlabeled dNTPs, Detection Via Labeled Template As with standard protocols in routine use in multiplexed hybridization assays, the DNA target to be analyzed can itself be labeled in the course of PCR by incorporation of labeled probes. Under conditions such as those described in Examples 6 and 7, a labeled target is annealed to probes. Matching probes are elongated using unlabeled dNTPs. Following completion of the elongation reaction, detection is performed by setting the temperature ($T_{det}$) to a value above the melting temperature ($T_{non-match}$) of the complex formed by target and non-matched probe, but below the melting temperature ($T_{match}$) of the complex formed by target and matched, and hence elongated, probe. The latter complex, displaying a long stretch of duplex region, will be significantly more stable than the former so that ($T_{non-match}$)<T<($T_{match}$). Typical values for T are in the range of 70° C. to 80° C. Under these conditions, only the complex formed by target and elongated probe will stable, while the complex formed by target and non-matching probe, and hence the fluorescence signal from the corresponding solid phase carrier, will be lost. That is, in contrast to other designs, it is the decrease of signal intensity associated with the non-matching probe which is detected, rather than the increase in intensity associated the matching probe. FIG. 21 illustrates the design which eliminates the need for labeled dNTPs or ddNTPs. This is useful in the preferred embodiments of this invention, where labeled dNTPs or ddNTPs can absorb non-specifically to encoded particles, thereby increasing the background of the signal and decreasing the discriminatory power of the assays. In addition, by using a labeled target, this protocol is directly compatible with methods of polymorphism analysis by hybridization of sequence-specific oligonucleotides.

Example 23: Real-Time On-Chip Signal Amplification

Figure 22:
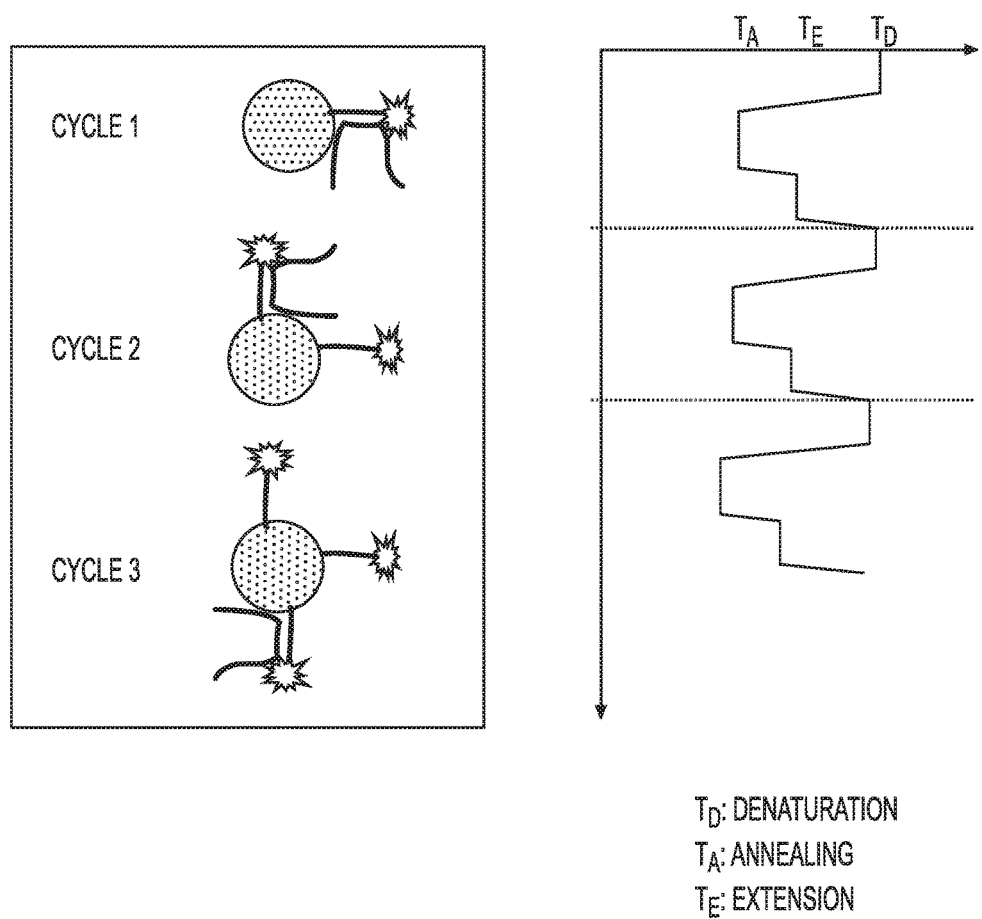
FIG. 22 is an illustration of linear amplification where sequence specific probes are immobilized.

A standard temperature control apparatus used with a planar geometry such as that illustrated in FIG. 22 permits the application of programmed temperature profiles to a multiplexed extension of SSPs. Under conditions of Examples 6 and 7, a given template mediates the elongation of one probe in each of multiple repeated "denature-anneal-extend" cycles. In the first cycle, a target molecule binds to a probe and the probe is elongated or extended. In the next cycle, the target molecule disassociates from the first probe in the "denature" phase (at a typical temperature of 95° C.), then anneals with another probe molecule in the "anneal" phase (at a typical temperature of 55° C.) and mediates the extension of the probe in the "extend" phase (at a typical temperature of 72° C.). In N cycles, each template mediates the extension of N probes, a protocol corresponding to linear amplification (FIG. 30). In a preferred embodiment of this invention, in which planar arrays of encoded beads are used to display probes in a multiplexed extension reaction, a series of temperature cycles is applied to the reaction mixture contained between two planar, parallel substrates. One substrate permits direct optical access and direct imaging of an entire array of encoded beads. The preferred embodiment provides for real-time amplification by permitting images of the entire bead array to be recorded instantly at the completion of each cycle.

Genomic, mitochondrial or other enriched DNA can be used for direct detection using on-chip linear amplification without sequence specific amplification. This is possible when an amount of DNA sufficient for detection is provided in the sample. In the bead array format, if $10^4$ fluorophores are required for detection of signal from each bead, 30 cycles of linear amplification will reduce the requisite number to ~300. Assuming the use of 100 beads of the requisite type within the array, the requisite total number of fluorophores would be ~$10^5$, a number typically available in clinical samples. For example, typical PCR reactions for clinical molecular typing of HLA are performed with 0.1 to 1 μg of genomic DNA. One μg of human genomic DNA corresponds to approximately $10^{18}$ moles, thus, $6 \times 10^5$ copies of the gene of interest. This small amount of sample required by the miniaturized bead array platform and on-chip amplification makes the direct use of pre-PCR samples possible. This not only simplifies sample preparation but, more importantly, eliminates the complexity of multiplexed PCR, frequently a rate limiting step in the development of multiplexed genetic analysis.

Example 24: Construction of a Probe Library for Designated and Unselected Polymorphisms for CF Mutation Analysis To increase the specificity of elongation probes and avoid false positives, elongation probes were designed to accommodate all known polymorphisms present in a target sequence. In addition, PCR primers were designed taking into consideration designated and non-designated polymorphisms.

The G/C mutation at position 1172 of R347P on Exon 7 within the CFTR gene, one of 25 mutations within the standard population carrier screening panel for cystic fibrosis, was selected as a designated polymorphism. There are 3 CF mutations with Exon 7 included in the mutation panel for general population carrier screening (see Federation of American Societies of Experimental Biology website (domain name .org) at resource ID genetics/acmg). A polymorphism G/T/A at the same site has been reported (see website having server name genet.sickkids.on with domain name ca, at resource ID cftr), and in addition, non-designated polymorphisms have been reported at positions 1175, 1178, 1186, 1187 and 1189. All of these polymorphisms can interfere with desired probe elongation.

The construction of a set of degenerate probes for eMAP is illustrated below for R347P (indicated by the bold-faced G) which is surrounded by numerous non-designated polymorphisms, indicated by capital letters:

| Normal Target Sequence for Elongation: | 5' 3'<br>Gca Tgg Cgg tea<br>ctC GgC a | SEQ. ID NO.: 166 |
|---|---|---|
| Degenerate Elongation Probe Set: | Ngt Ycc Ycc agt<br>gaY RcY t<br>3' 5' | | where N = a, c, g or t; R (puRines) = a or g and Y (pYrimidines) = c or t, implying a degeneracy of 128 for the set.

Primer Pooling for Mutation Analysis—

The principal objective in the construction of a degenerate set is to provide at least one probe sequence to match the target sequence sufficiently closely to ensure probe annealing and elongation. While this is always attainable in principle by providing the entire set of possible probe sequences associated with the designated polymorphism, as in the preferred mode of constructing covering sets, the degree of degeneracy of that set, 128 in the example, would lead to a corresponding reduction in assay signal intensity by two orders of magnitude if all probes were to be placed onto a single bead type for complete probe pooling. Splitting pools would improve the situation by distributing the probe set over multiple bead types, but only at the expense of increasing array complexity.

First, the probe pool was split into a minimum of two or more pools, each pool providing the complementary composition, at probe position M (i.e., the probe's 3' terminus), for each of the possible compositions of the designated polymorphic site. In the example, four such pools are required for a positive identification of the designated target composition. Next, non-designated polymorphic sites were examined successively in the order of distance from the designated site. Among these, positions within the TEI region are of special importance to ensure elongation. That is, each pool is constructed to contain all possible probe compositions for those non-designated sites that fall within the TEI region. Finally, as with the construction of degenerate probes for cloning and sequencing of variable genes, the degeneracy of the set is minimized by placing neutral bases such as inosine into those probe positions which are located outside the TEI region provided these are known never to be juxtaposed to G in the target. In the example, non-designated polymorphisms in probe positions M–16 and M–18 qualify. That is, the minimal degeneracy of each of the four pools would increase to four, producing a corresponding reduction in signal intensity. As an empirical guideline, signal reduction preferably will be limited to a factor of eight.

In total, four pools, each uniquely assigned to one bead type and containing eight degenerate probe sequences, will cover the target sequence. These sequences are analogous to those shown below for pools variable at M:

| Probe pool for CF mutation R347P | | | | |
|---|---|---|---|---|
| R347P | Cgt | Acc | Gcc | agt | gaG GgC |
| | 3' | | | | 5' |
| POOL 1 | Cgt | Acc | Gcc | agt | gaG IgI SEQ. ID NO.: 169 |
| | Cgt | Acc | Gcc | agt | gaC IgI SEQ. ID NO.: 170 |
| | Cgt | Acc | Ccc | agt | gaG IgI SEQ. ID NO.: 171 |
| | Cgt | Acc | Ccc | agt | gaC IgI SEQ. ID NO.: 172 |
| | Cgt | Tcc | Gcc | agt | gaG IgI SEQ. ID NO.: 173 |
| | Cgt | Tcc | Gcc | agt | gaC IgI SEQ. ID NO.: 174 |
| | Cgt | Tcc | Ccc | agt | gaG IgI SEQ. ID NO.: 175 |
| | Cgt | Tcc | Ccc | agt | gaC IgI SEQ. ID NO.: 176 |
| POOL 2 | Ggt | Acc | Gcc | agt | gaG IgI SEQ. ID NO.: 177 |
| | Ggt | Acc | Gcc | agt | gaC IgI SEQ. ID NO.: 178 |
| | Ggt | Acc | Ccc | agt | gaG IgI SEQ. ID NO.: 179 |
| | Ggt | Acc | Ccc | agt | gaC IgI SEQ. ID NO.: 170 |
| | Ggt | Tcc | Gcc | agt | gaG IgI SEQ. ID NO.: 181 |
| | Ggt | Tcc | Gcc | agt | gaC IgI SEQ. ID NO.: 182 |
| | Ggt | Tcc | Ccc | agt | gaG IgI SEQ. ID NO.: 183 |
| | Ggt | Tcc | Ccc | agt | gaC IgI SEQ. ID NO.: 184 |
| POOL 3 | Agt | Acc | Gcc | agt | gaG IgI SEQ. ID NO.: 185 |
| | Agt | Acc | Gcc | agt | gaC IgI SEQ. ID NO.: 186 |
| | Agt | Acc | Ccc | agt | gaG IgI SEQ. ID NO.: 187 |
| | Agt | Acc | Ccc | agt | gaC IgI SEQ. ID NO.: 188 |
| | Agt | Tcc | Gcc | agt | gaG IgI SEQ. ID NO.: 189 |
| | Agt | Tcc | Gcc | agt | gaC IgI SEQ. ID NO.: 190 |
| | Agt | Tcc | Ccc | agt | gaG IgI SEQ. ID NO.: 191 |
| | Agt | Tcc | Ccc | agt | gaC IgI SEQ. ID NO.: 192 |
| POOL 4 | Tgt | Acc | Gcc | agt | gaG IgI SEQ. ID NO.: 193 |
| | Tgt | Acc | Gcc | agt | gaC IgI SEQ. ID NO.: 194 |
| | Tgt | Acc | Ccc | agt | gaG IgI SEQ. ID NO.: 195 |
| | Tgt | Acc | Ccc | agt | gaC IgI SEQ. ID NO.: 196 |
| | Tgt | Tcc | Gcc | agt | gaG IgI SEQ. ID NO.: 197 |
| | Tgt | Tcc | Gcc | agt | gaC IgI SEQ. ID NO.: 198 |
| | Tgt | Tcc | Ccc | agt | gaG IgI SEQ. ID NO.: 199 |
| | Tgt | Tcc | Ccc | agt | gaC IgI SEQ. ID NO.: 200 |

In general, the type of non-designated polymorphisms on the antisense strand may differ from that on the sense strand, and it may then be advantageous to construct degenerate probe sets for the antisense strand. As with the construction of degenerate elongation probes, degenerate hybridization probe sets may be constructed by analogous rules to minimize the degeneracy.

Example 25: "Single Tube" CF Mutation Analysis by eMAP

This example is concerned with methods and compositions for performing an eMAP assay, wherein the annealing and elongation steps occur in the reactor. This embodiment is useful because it obviates the need for sample transfer between reactors as well as purification or extraction procedures, thus simplifying the assay and reducing the possibility of error. A non-limiting exemplary protocol follows.

Genomic DNA extracted from several patients was amplified with corresponding primers in a multiplex PCR (mPCR) reaction. The PCR conditions and reagent compositions were as follows.

PRIMER DESIGN: Sense primers were synthesized without any modification and antisense primers with "Phosphate" at the 5' end. Multiplex PCR was performed in two groups.

Group one amplification includes exon 5, 7, 9, 12, 13, 14B, 16, 18 and 19. Amplifications for group 2 includes primers for exon 3, 4, 10, 11, 20, 21 and intron 19. The 5' phosphate group modification on exon 5, 7, and 11 was included on forward primer to use antisense target for probe elongation. While sense target was used for all other amplicons by placing phosphate group on reverse primer.

PCR Master Mix Composition
For 10 ul reaction/sample:

| Components | Volume (μl) |
|---|---|
| 10X PCR buffer | 1.0 |
| 25 mM MgCl$_2$ | 0.7 |
| dNTPs (2.5 mM) | 2.0 |
| Primer mix (Multiplex 10x) | 1.5 |
| Taq DNA polymerase | 0.3 |
| ddH2O | 1.5 |
| DNA | 3.0 |
| Total | 10 |

PCR Cycling

| 94° C. 5 min, | 94° C. 10 sec., | 60° C. 10 sec., | 72° C. 40 sec |
|---|---|---|---|
| 72° C. 5 min., | Number of cycles: | 28-35 | |

The reaction volume can be adjusted according to experimental need. Amplifications are performed using a Perkin Elmer 9600 thermal cycler. Optimal primer concentrations were determined for each primer pair. Following amplifications, 5 ul of the product was removed for gel electrophoresis. Single stranded DNA targets were generated as follows: Two microliters of exonuclease was added to 50 of PCR product, incubated at 37° C. for 15 minutes and enzyme was denatured at 80° C. for 15 minutes. After denaturation, 1 μl of 10× exonuclease buffer was added with 1 ml of λ exonuclease (5 U/μl) and incubated at 37° C. for 20 minutes and the reaction was stopped by heating at 75° C. for 10 minutes.

On Chip Elongation

Wild type and mutant probes for 26 CF mutations were coupled on the bead surface and assembled on the chip array. The probes were also divided into two groups. A third group was assembled for reflex test including 5T/7T/9T polymorphisms.

Elongation Group 1, total 31 groups on the chip surface.

| Bead cluster # | Mutation |
|---|---|
| 1 | G85E-WT |
| 2 | G85E-M |
| 3 | 621+1G>T-WT |
| 4 | 621+1G>T-M |
| 5 | R117H-WT |
| 6 | R117H-M |
| 7 | β Actin |
| 8 | 1148T-WT |
| 9 | 1148T-M |
| 10 | 508-WT |
| 11 | F508 |
| 12 | 1507 |
| 13 | G542X-WT |
| 14 | G542X-M |
| 15 | G551D-WT |
| 16 | G551D-M |
| 17 | R553X-WT |
| 18 | R553X-M |
| 19 | BIOTIN |
| 20 | 1717-1G>A-WT |
| 21 | 1717-1G>A-M |
| 22 | R560T-WT |
| 23 | R560T-M |
| 24 | 3849+10kbT-WT |

| Bead cluster # | Mutation |
| --- | --- |
| 25 | 3849+10kbT-M |
| 26 | W1282X-WT |
| 27 | W1282X-M |
| 28 | N1303K-WT |
| 29 | N1303K-M |
| 30 | OLIGO-C |

Elongation Group 2, total 28 groups on the chip surface.

| Cluster # | Mutation |
| --- | --- |
| 1 | 711+1G>T-WT |
| 2 | 711+1G>T-M |
| 3 | R334W-WT |
| 4 | R334W-M |
| 5 | 1078delT-WT |
| 6 | 1078delT-M |
| 7 | β Actin |
| 8 | R347P-WT |
| 9 | R347P-M |
| 10 | A455E-WT |
| 11 | A455E-M |
| 12 | 1898+1G>A-WT |
| 13 | 1898+1G>A-WT |
| 14 | 2184delA-WJ |
| 15 | 2184delA-M |
| 16 | 2789+5G-WT |
| 17 | 2789+5G-M |
| 18 | BIOTIN |
| 19 | 3120+1G>A-WT |
| 20 | 3120+1G>A-WT |
| 21 | R1162X-WT |
| 22 | R1162X-M |
| 23 | 3659delC-WT |
| 24 | 3659delC-M |
| 25 | D1152-WT |
| 26 | D1152-M |
| 27 | OLIGO-C | mPCR group 2:

Elongation Group 3, total 6 groups

| Cluster # | Mutation |
| --- | --- |
| 1 | β Actin |
| 1 | Oligo C |
| 2 | 5T |
| 3 | 7T |
| 4 | 9T |
| 5 | Biotin |

Elongation reaction buffer has been optimized for use in uniplex and/or multiplex target elongation assays and composed of, Tris-HCL (pH 8.5) 1.2 mM, EDTA 1 uM, DTT 10 KCl 1 μM, MgCl$_2$ 13 μM, 2-Mercaptoethanol 10 μM, Glycerol 0.5%, Tween-20 0.05%, and Nonidet 0.05%. Ten microliters of elongation reaction mixture was added on each chip containing 1× Reaction buffer 0.1 μM of Labeled dNTP, 1.0 μM of dNTPs mix, 3 U of DNA polymerase and 5 μl (~5 ng) of target DNA (patient sample). The reaction mix was added on the chip surface and incubated at 53° C. for 15 min and then at 60° C. for 3 min. The chip was washed with wash buffer containing 0.01% SDS, covered with a clean cover slip and analyzed using a Bioarray Solutions imaging system. Images are analyzed to determine the identity of each of the elongated probes.

Example 26: CF Mutation Analysis—Single Tube Single Chip-One Step Elongation

Probes for 26 CF mutations and controls were coupled on the surface of 51 types of beads. Probe coupled beads were assembled on the surface of a single chip. Genomic DNA was extracted from several patients and was amplified with corresponding primers in a multiplexed PCR (mPCR) reaction, as described in the previous example Following amplification, single stranded DNA products were produced using 2 exonuclease. Single or pooled PCR products (~5 ng) were added to a reaction mixture containing reaction buffer, deoxynucleotide (dNTP) analogs (NEN Life Sciences), each type of unlabeled dNTP, and DNA polymerase (Amersham Pharmacia Biotech, NJ). The annealing/elongation reaction was allowed to proceed in a temperature controlled cycler. The temperature steps were as follows: 20 minutes at 53° C., and 3 minutes at 60° C. The bead array was then washed with dsH$_2$O containing 0.01% SDS for 5 to 15 minutes. An image containing the fluorescent signal form each bead within the array was recorded using a fluorescence microscope and a CCD camera. Images were analyzed to determine the identity of each of the elongated probes.

The composition of bead chip containing 26 CF mutations is provided below.

Elongation Group 4, total 51 groups

| Cluster # | Mutation |
| --- | --- |
| 1 | β Actin |
| 2 | G85E-WT |
| 3 | G85E-M |
| 4 | 621+1G>T-WT |
| 5 | 621+1G>T-M |
| 6 | R117H-WT |
| 7 | R117H-M |
| 8 | I148T-WT |
| 9 | I148T-M |
| 10 | 711+1G>T-WT |
| 11 | 711+1G>T-M |
| 12 | A455E-WT |
| 13 | A455E-M |
| 14 | 508-WT |
| 15 | F508 |
| 16 | 1507 |
| 17 | R533-WT |
| 18 | R533-M |
| 19 | G542-WT |
| 20 | G542-M |
| 21 | G551D-WT |
| 22 | G551D-M |
| 23 | R560-WT |
| 24 | R560-M |
| 25 | 1898+IG-WT |
| 26 | 1898+1G-M |
| 27 | 2184delA-WT |
| 28 | 2184delA-M |
| 29 | 2789+5G>A-WT |
| 30 | 2789+5G>A-M |
| 31 | 3120+1G-WT |
| 32 | 3120+1G-WT |
| 33 | D1152-WT |
| 34 | D1152-M |
| 35 | R1162-WT |
| 36 | R1162-M |
| 37 | OLIGO-C |
| 38 | W1282X-WT |
| 39 | W1282-M |
| 40 | N1303K-WT |
| 41 | N1303-M |
| 42 | R334-WT |
| 43 | R334-M |
| 44 | 1078delT-WT |
| 45 | 1078delT-M |

-continued

| Cluster # | Mutation |
|---|---|
| 46 | 3849-10kb-WT |
| 47 | 3849-10kb-M |
| 49 | 1717-1G>A-WT |
| 50 | 1717-1G>A-WT |
| 51 | Biotin |

Example 27: Identification of Three or More Base Deletions and/or Insertions by eMAP Elongation was used to analyze mutations with more than 3 base deletions or insertions. Probes were designed by placing mutant bases 3-5 base before 3' end. The wild type probes were designed to either include or exclude mutant bases (terminating before mutations). The following is an example of mutations caused by a deletion of ATCTC and/or insertion of AGGTA. The probe designs are as follows:
1. WT1— ----------------- ATCTCgca
2. WT2— -----------------
3. M1— -------------------- gca (deletion only)
4. M2— -------------------- AGGTAgca (deletion and insertion)

Wild type probes were either coupled on the surface of differentially encoded beads or pooled as described in this invention. Probes for mutation 1 (M1: deletion) and 2 (M2: insertion) were coupled on different beads. Both wild type probes provide similar information, while the mutant probes can show the type of mutation identified in a specific sample.

Example 28: Hairpin Probes

Figure 23:
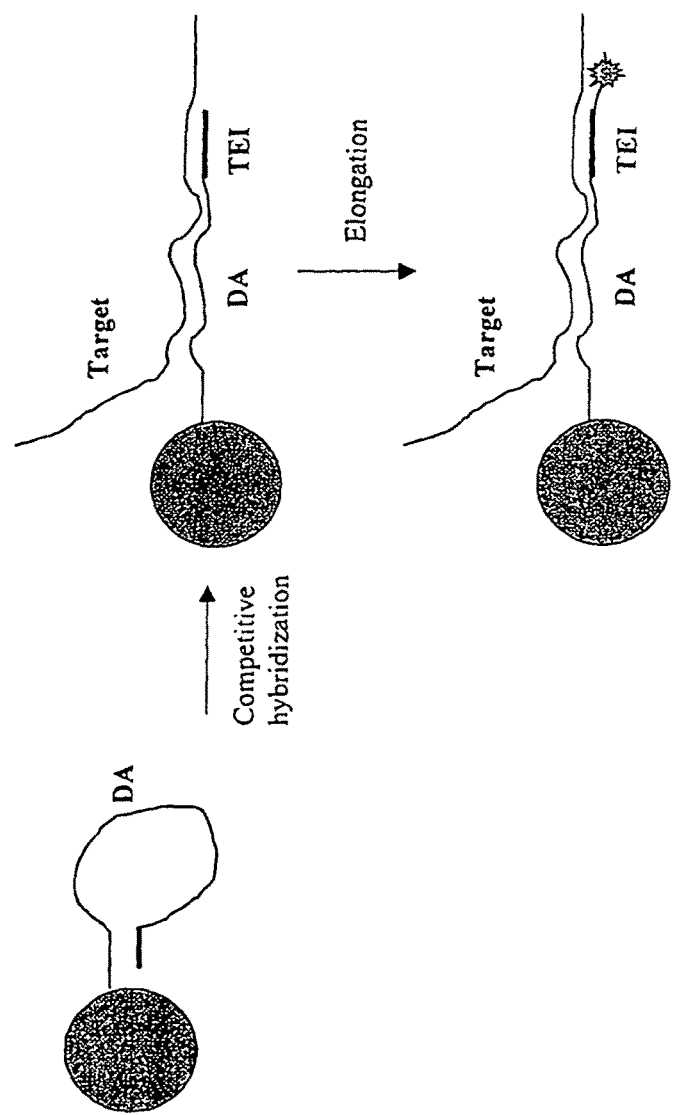
FIG. 23 is an illustration of the utilization of hairpin probes.

In certain embodiments of this invention, bead-displayed priming probes form hairpin structures. A hairpin structure may include a sequence fragment at the 5' end that is complementary to the TEI region and the DA sequence, as shown in FIG. 23. During a competitive hybridization reaction, the hairpin structure opens whenever the DA region preferentially hybridizes with the target sequence. Under this condition, the TEI region will align with the designated polymorphic site and the elongation reaction will occur. The competitive nature of the reaction can be used to control tolerance level of probes.

Example 29: Analysis of Cystic Fibrosis and Ashkenazi Jewish Disease Mutations by Multiplexed Elongation of Allele Specific Oligonucleotides Displayed on Custom Bead Arrays A novel assay for the high throughput multiplexed analysis of mutations has been evaluated for ACMG+ panel of Cystic Fibrosis mutations. In addition, an Ashkenazi Jewish disease panel also has been developed to detect common mutations known to cause Tay-Sachs, Canavan, Gaucher, Niemann-Pick, Bloom Syndrome, Fancomi Anemia, Familial Dysautonomia, and mucolipodosis IV.

In elongated-mediated multiplexed analysis of polymorphisms (eMAP), allele specific oligonucleotides (ASO) containing variable 3' terminal sequences are attached to color-encoded beads which are in turn arrayed on silicon chips. Elongation products for normal and mutant sequences are simultaneously detected by instant imaging of fluorescence signals from the entire array.

Figure 24:
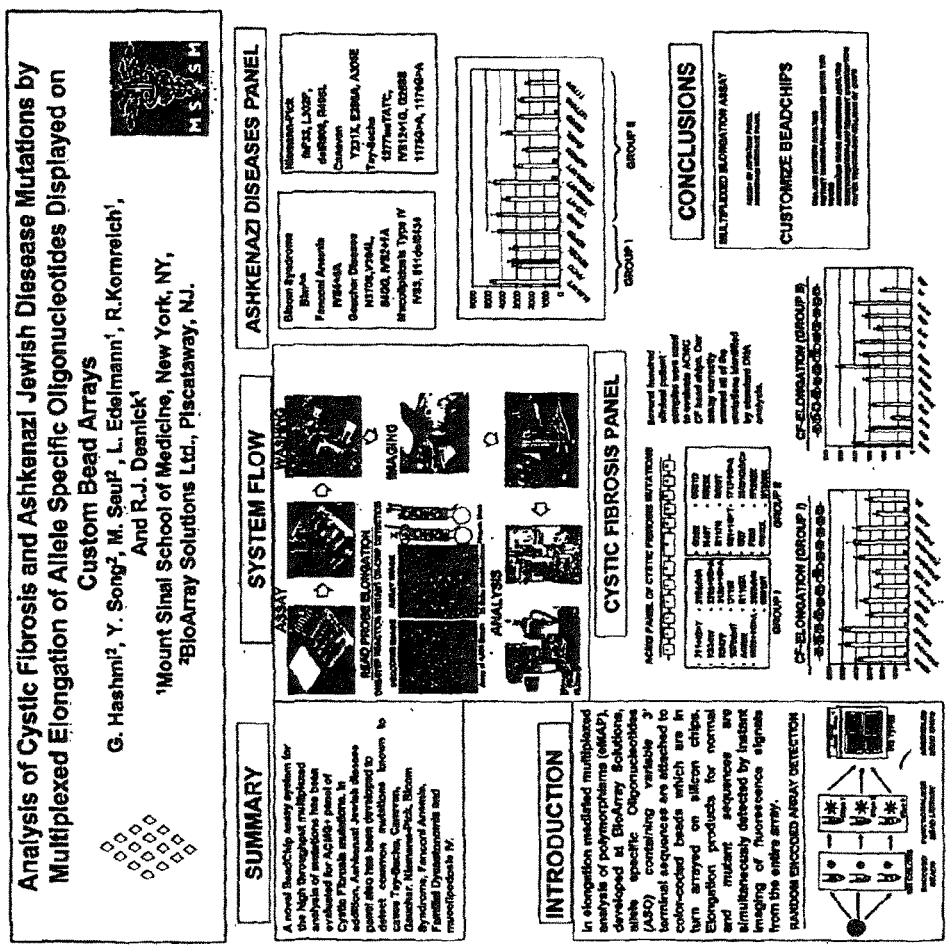
FIG. 24 is an illustration of applying this invention to the analysis of cystic fibrosis and Ashkenazi Jewish disease mutations.

In this example, several hundred clinical patient samples were used to evaluate ACMG CF bead chips. As shown in FIG. 24, the assay correctly scored all of the mutations identified by standard DNA analysis.

In summary, a multiplexed elongation assay comprising customized beads was used to study mutations corresponding to ACMG+ and Ashkenazi disease panels. The customized beads can be used for DNA and protein analysis. The use of these customized beads are advantageous for several reasons including (1) instant imaging—the turnaround time for the assay is within two hours (2) automated image acquisition and analysis (3) miniaturization, which means low reagent consumption, and (4) the beadchips are synthesized using wafer technology, so that millions of chips can be mass-produced, if desired.

We claim:

1. A method of concurrent determination of nucleotide composition at designated polymorphic sites located within one or more target nucleotide sequences, said method comprising the following steps:
   a. Providing one or more sets of probes, wherein each set of probes comprises two or more member probes, wherein each of the two or more member probes comprises a terminal elongation initiation (TEI) region and a duplex anchoring (DA) region, wherein the TEI region and the DA region are linked by a neutral linker, wherein the TEI region and the DA region align with separate regions of a target nucleic acid sequence and the neutral linker does not align with the target nucleic acid sequence, and
   wherein the TEI region aligns with a subsequence of a target nucleic acid sequence comprising a first designated polymorphic site;
   wherein the TEI region comprises each of the two or more member probes' three or four 3' terminal nucleotide positions and an interrogation site at its 3'-most terminal nucleotide position, wherein the interrogation site is perfectly complementary to the first designated polymorphic site, and
   wherein the two or more member probes differ in sequence in the TEI region in at least the interrogation site;
   wherein the difference in sequence in the TEI region in at least the interrogation site results in each set of probes comprising the two or more member probes required for perfect complementarity to variations in nucleotide sequence at the first polymorphic site; and
   wherein each of the two or more member probes is immobilized on an encoded microparticle, said encoded microparticle comprising a distinguishable characteristic that uniquely identifies its immobilized probe;
   b. Contacting the one or more sets of probes with one or more target nucleotide sequences in a single multiplexed reaction so as to permit formation of hybridization complexes by placing each of the two or more member probes' interrogation site in direct alignment with the first designated polymorphic site, wherein the TEI region initiates an elongation reaction to form an elongation product when sequence of the TEI region is complementary to its corresponding subsequence of the target nucleotide at the first designated polymorphic site;
   c. Subjecting the hybridization complexes to a polymerase-catalyzed elongation reaction, wherein for each hybridization complex, formation of the elongation product indicates a match or absence of the elongation product indicates a mismatch between the interrogation site and the first designated polymorphic site, and formation of the elongation product results in a change in the distinguishable characteristic; and
   d. Determining a change in the distinguishable characteristic for each encoded microparticle to determine the composition of the first designated polymorphic site.

2. The method of claim 1, wherein the polymerase-catalyzed elongation reaction comprises adding one or more deoxynucleotide triphosphates and a polymerase capable of extending or elongating probes, wherein the polymerase lacks 3' to 5' exonuclease activity.

3. The method of claim 2, wherein at least one of the deoxynucleotide triphosphates is labeled so as to generate an optically detectable signature associated with the elongation product.

4. The method of claim 1, wherein the one or more target nucleotide sequences are products of at least one polymerase chain reaction.

5. The method of claim 1, wherein the microparticles are encoded by staining with a fluorophore dye.

6. The method of claim 1, wherein the microparticles are encoded by staining with a chromophore dye.

7. The method of claim 1, wherein the microparticles are immobilized on a solid support.

8. The method of claim 1, further comprising determination of a second polymorphic site, wherein the first polymorphic site and the second polymorphic site are correlated, wherein the second polymorphic site is determined by:
   contacting the elongation product formed at (c) with a second probe designed to hybridize to the second polymorphic site;
   determining hybridization of the second probe to the second designated polymorphic site for each elongation product; and determining composition of the second designated polymorphic site.

9. The method of claim 1, wherein the subsequence of the target nucleic acid further comprises a non-designated polymorphic site, wherein the two or more member probes further differ in sequence in the TEI region at nucleotide position corresponding to a non-designated polymorphic site, and wherein each set of probes comprises the two or more member probes required for perfect complementarity to each nucleotide sequence combination at the non-designated site and the first polymorphic site.

10. The method of claim 1, wherein the one or more deoxynucleotide triphosphates are not labeled.

11. The method of claim 1, wherein the step of determining is performed in solution.

12. The method of claim 11, wherein the step of determining is performed by flow cytometry.

13. The method of claim 7, wherein the encoded microparticles are randomly immobilized on the solid support.

* * * * *